US010781230B2

(12) United States Patent
Minagawa et al.

(10) Patent No.: US 10,781,230 B2
(45) Date of Patent: Sep. 22, 2020

(54) NUCLEOSIDE DERIVATIVE OR SALT THEREOF, POLYNUCLEOTIDE SYNTHESIS REAGENT, METHOD FOR PRODUCING POLYNUCLEOTIDE, POLYNUCLEOTIDE, AND METHOD FOR PRODUCING BINDING NUCLEIC ACID MOLECULE

(71) Applicants: NEC Solution Innovators, Ltd., Tokyo (JP); NATIONAL UNIVERSITY CORPORATION GUNMA UNIVERSITY, Maebashi-shi, Gunma (JP)

(72) Inventors: Hirotaka Minagawa, Tokyo (JP); Katsunori Horii, Tokyo (JP); Jou Akitomi, Tokyo (JP); Naoto Kaneko, Tokyo (JP); Iwao Waga, Tokyo (JP); Masayasu Kuwahara, Maebashi (JP)

(73) Assignees: NEC Solution Innovators, Ltd., Koto-ku, Tokyo (JP); NATIONAL UNIVERSITY CORPORATION GUNMA UNIVERSITY, Maebashi-shi, Gunma (JP)

( * ) Notice: Subject to any disclaimer, the term of this patent is extended or adjusted under 35 U.S.C. 154(b) by 0 days.

(21) Appl. No.: 16/333,333

(22) PCT Filed: Sep. 14, 2017

(86) PCT No.: PCT/JP2017/033211
§ 371 (c)(1),
(2) Date: Mar. 14, 2019

(87) PCT Pub. No.: WO2018/052064
PCT Pub. Date: Mar. 22, 2018

(65) Prior Publication Data
US 2019/0211048 A1    Jul. 11, 2019

(30) Foreign Application Priority Data

Sep. 15, 2016 (JP) .................................. 2016-180894
May 30, 2017 (JP) ..................... PCT/JP2017/020065

(51) Int. Cl.
*C07H 19/02* (2006.01)
*C07H 19/04* (2006.01)
(Continued)

(52) U.S. Cl.
CPC ............. *C07H 19/20* (2013.01); *C07H 19/14* (2013.01); *C07H 21/02* (2013.01); *C07H 21/04* (2013.01);
(Continued)

(58) Field of Classification Search
None
See application file for complete search history.

(56) References Cited

U.S. PATENT DOCUMENTS 8,853,373 B2    10/2014 Kuwahara et al.
2005/0130195 A1    6/2005 Fujihara et al.
2016/0311845 A1    10/2016 Kuwahara

FOREIGN PATENT DOCUMENTS

CN    105738633 A    7/2016
JP    10239312 A    9/1998
(Continued)

OTHER PUBLICATIONS

Communication dated May 13, 2019 from the European Patent Office in application No. 17850965.9.
Yuri Imaizumi et al., "Efficacy of Base-Modification on Target Binding of Small Molecule DNA Aptamers," Journal of the American Chemical Society, 2013, pp. 9412-9419, vol. 135, No. 25.
International Search Report of PCT/JP2017/033211 dated Oct. 24, 2017.
Extended European Search Report dated Sep. 26, 2019 issued by the European Patent Office in application No. 17874515.4.
(Continued)

Primary Examiner — Traviss C McIntosh, III
(74) Attorney, Agent, or Firm — Sughrue Mion, PLLC

(57) ABSTRACT

The present invention provides a novel nucleoside derivative or a salt thereof, a polynucleotide synthesis reagent, a method for producing a polynucleotide, a polynucleotide, and a method for producing a binding nucleic acid molecule. The nucleoside derivative or a salt thereof of the present invention is represented by the following chemical formula (1):

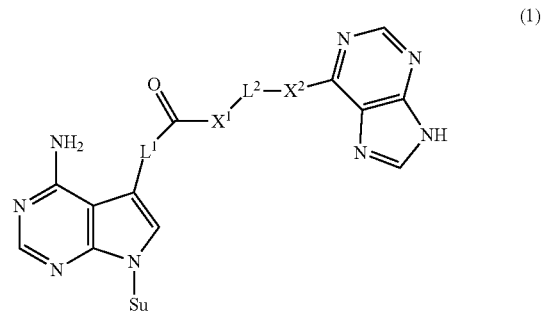

where in the chemical formula (1), Su is an atomic group having a sugar skeleton at a nucleoside residue or an atomic group having a sugar phosphate skeleton at a nucleotide residue, and may or may not have a protecting group, $L^1$ and $L^2$ are each independently a straight-chain or branched, saturated or unsaturated hydrocarbon group having 2 to 10 carbon atoms, $X^1$ and $X^2$ are each independently an imino group (—$NR^1$—), an ether group (—O—), or a thioether group (—S—), and the $R^1$ is a hydrogen atom or a straight-chain or branched, saturated or unsaturated hydrocarbon group having 2 to 10 carbon atoms.

10 Claims, 11 Drawing Sheets

Specification includes a Sequence Listing.

(51) Int. Cl.
*C07H 19/14* (2006.01)
*C07H 19/20* (2006.01)
*C07H 21/02* (2006.01)
*C07H 21/04* (2006.01)
*C12N 15/115* (2010.01)
*C07K 16/00* (2006.01)

(52) U.S. Cl.
CPC ............ *C07K 16/00* (2013.01); *C12N 15/115* (2013.01); *Y02P 20/55* (2015.11)

(56) References Cited

FOREIGN PATENT DOCUMENTS

| | | | |
|---|---|---|---|
| JP | 10274654 A | 10/1998 | |
| JP | 2007-056001 A | 3/2007 | |
| JP | 2012-200204 A | 10/2012 | |
| JP | 2013-040118 A | 2/2013 | |
| JP | 2016-056136 A | 4/2016 | |
| WO | 2011/019031 A1 | 2/2011 | |
| WO | 2015/064223 A1 | 5/2015 | |
| WO | WO-2015064223 A1 * | 5/2015 | ........... C07H 19/073 |
| WO | 2018051569 A1 | 3/2018 | |

OTHER PUBLICATIONS

Notice of Reasons for Refusal dated Jan. 30, 2020 from the Japanese Patent Office in application No. 2018-539512.
Communication dated Mar. 23, 2020, issued by the European Patent Office in couterpart European Application No. 17850476.7 (14 pages total).
Yuuya Kasahara, "Development of the Convenient Method for Artificial Nucleic Acid Aptamer Preparations Using CE-SELEX", The Graduate School of Engineering (Doctor Course), Gunma University, XP55674545, pp. 1-111 (2014) (117 pages total).
Vorobyeva et al., "Aptamers Against Immunologic Targets: Diagnostic and Therapeutic Prospects", Nucleic Acid Therapeutics, vol. 26, No. 1, pp. 52-65 (2016) (14 pages total).
Oorwijn et al., "A pathogenic role for secretory IgA in IgA nephropathy", Kidney International, vol. 69, No. 7, pp. 1131-1138 (2006) (8 pages total).
Kasahara et al., "Artificial Specific Binders Directly Recovered from Chemically Modified Nucleic Acid Libraries", Journal of Nucleic Acids, vol. 2012, pp. 1-13 (2012) (14 pages total).
Minigawa et al., "Fluorescence Polarization-Based Rapid Detection System for Salivary Biomarkers Using Modified DNA Aptamers Containing Base-Appended Bases", Analytical Chemistry, vol. 92, No. 2, pp. 1780-1787 (2019) (8 pages total).
Communication dated Apr. 28, 2020, issued by the Japanese Patent Office in Japanese Application No. 2018-552458.
Kuwahara, Polymers, vol. 63, No. 10, pp. 730-731, 2014 (5 total pages).
Kasahara et al., "Capillary Electrophoresis-Systematic Evolution of Ligands by Exponential Enrichment Selection of Base- and Sugar-Modified DNA Aptamers: Target Binding Dominated by 2'-O,4'-C-Methylene-Bridged/Locked Nucleic Acid Primer", Analytical Chemistry, vol. 85, No. 10, pp. 4961-4967, 2013 (7 pages total).
Extended European Search Report dated Jul. 10, 2020 for related European Patent Application No. 17850476.7.

* cited by examiner

NUCLEOSIDE DERIVATIVE OR SALT THEREOF, POLYNUCLEOTIDE SYNTHESIS REAGENT, METHOD FOR PRODUCING POLYNUCLEOTIDE, POLYNUCLEOTIDE, AND METHOD FOR PRODUCING BINDING NUCLEIC ACID MOLECULE

CROSS REFERENCE TO RELATED APPLICATIONS

This application is a National Stage of International Application No. PCT/JP2017/033211 filed Sep. 14, 2017, claiming priority based on Japanese Patent Application No. 2016-180894 filed Sep. 15, 2016 and International Application No. PCT/JP2017/020065 filed May 30, 2017, the entire disclosures of which are incorporated herein in their entirety by reference.

TECHNICAL FIELD

The present invention relates to a nucleoside derivative or a salt thereof, a polynucleotide synthesis reagent, a method for producing a polynucleotide, a polynucleotide, and a method for producing a binding nucleic acid molecule.

BACKGROUND ART

In order to analyze a target in a specimen, a binding molecule that binds to a target is used. In addition to an antibody, a binding nucleic acid molecule that binds to a target such as an aptamer is also used as a binding molecule that binds to the target (Patent Literature 1).

As a method for obtaining the binding nucleic acid molecule, a SELEX (Systematic Evolution of Ligands by Exponential Enrichment) method in which a target is caused to come into contact with a large number of candidate polynucleotides and a polynucleotide that binds to the target among the candidate polynucleotides is selected as the binding nucleic acid molecule is known. When a binding nucleic acid molecule is obtained by the SELEX method, a modified nucleoside molecule obtained by modifying a natural nucleoside molecule is also used in addition to a natural nucleoside molecule that constitutes the binding nucleic acid molecule.

However, with known natural nucleosides and derivatives thereof, there are targets for which binding nucleic acid molecules with sufficient binding ability cannot be obtained. Therefore, there is a need for modified nucleoside derivatives that can be used, for example, in the production of aptamers.

CITATION LIST

Patent Literature

Patent Literature 1: JP 2012-200204 A

SUMMARY OF INVENTION

Technical Problem

Hence, the present invention is intended to provide a novel nucleoside derivative or a salt thereof, a polynucleotide synthesis reagent, a method for producing a polynucleotide, a polynucleotide, and a method for producing a binding nucleic acid molecule.

Solution to Problem

The nucleoside derivative or a salt thereof of the present invention is represented by the following chemical formula (1).

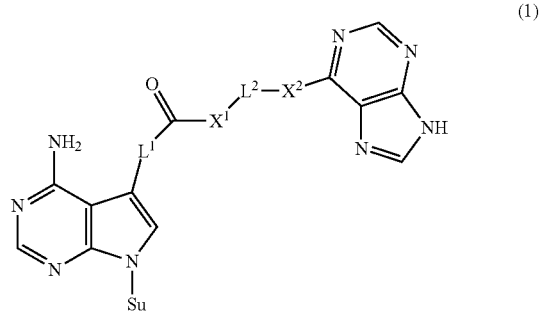

in the chemical formula (1), Su is an atomic group having a sugar skeleton at a nucleoside residue or an atomic group having a sugar phosphate skeleton at a nucleotide residue, and may or may not have a protecting group, $L^1$ and $L^2$ are each independently a straight-chain or branched, saturated or unsaturated hydrocarbon group having 2 to 10 carbon atoms, $X^1$ and $X^2$ are each independently an imino group ($-NR^1-$), an ether group ($-O-$), or a thioether group ($-S-$), and the $R^1$ is a hydrogen atom or a straight-chain or branched, saturated or unsaturated hydrocarbon group having 2 to 10 carbon atoms.

The polynucleotide synthesis reagent of the present invention includes a nucleotide derivative or a salt thereof including the nucleoside derivative or a salt thereof of the present invention.

The method for producing a polynucleotide of the present invention includes the step of synthesizing a polynucleotide using a nucleotide derivative or a salt thereof including the nucleoside derivative or a salt thereof of the present invention.

The polynucleotide of the present invention includes, as a building block, a nucleotide derivative or a salt thereof including the nucleoside derivative or a salt thereof of the present invention.

The method for producing a binding nucleic acid molecule of the present invention includes the steps of: causing a candidate polynucleotide and a target to come into contact with each other; and selecting the candidate polynucleotide bound to the target as a binding nucleic acid molecule that binds to the target, and the candidate polynucleotide is the polynucleotide of the present invention.

Advantageous Effects of Invention

The present invention can provide a novel nucleoside derivative or a salt thereof.

Figure 1:
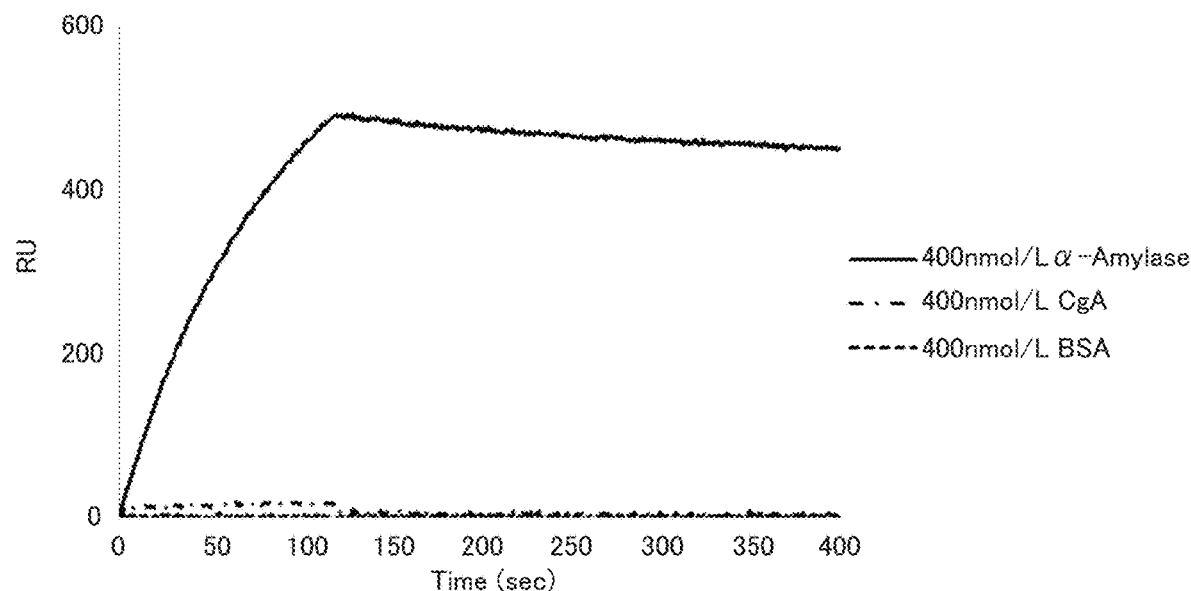
FIG. 1 is a graph showing the binding ability of an α-amylase-binding nucleic acid molecule to α-amylase in Example 2.

DESCRIPTION OF EMBODIMENTS (Nucleoside Derivative or Salt Thereof)

The nucleoside derivative or a salt thereof of the present invention is represented by the following chemical formula (1), as mentioned above.

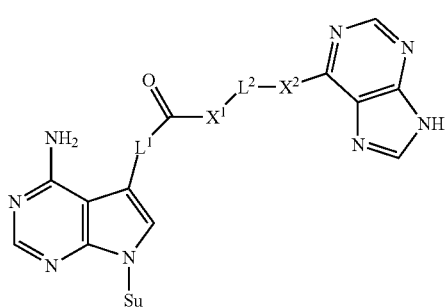

(1)

In the chemical formula (1), Su is an atomic group having a sugar skeleton at a nucleoside residue or an atomic group having a sugar phosphate skeleton at a nucleotide residue, and may or may not have a protecting group, $L^1$ and $L^2$ are each independently a straight-chain or branched, saturated or unsaturated hydrocarbon group having 2 to 10 carbon atoms, $X^1$ and $X^2$ are each independently an imino group (—$NR^1$—), an ether group (—O—), or a thioether group (—S—), and the $R^1$ is a hydrogen atom or a straight-chain or branched, saturated or unsaturated hydrocarbon group having 2 to 10 carbon atoms.

The nucleoside derivative of the present invention has two purine ring-like structures. The nucleoside derivative of the present invention thus has, for example, a relatively larger number of atoms capable of interacting within or between molecules than a nucleoside derivative having one purine ring-like structure. The binding nucleic acid molecule including the nucleoside derivative of the present invention therefore has an improved binding ability to a target, for example, compared to a nucleoside derivative having one purine ring-like structure. Thus, with the nucleoside derivative of the present invention, a binding nucleic acid molecule that exhibits excellent binding ability to a target can be produced, for example.

In the chemical formula (1), $L^1$ and $L^2$ are each independently a straight-chain or branched, saturated or unsaturated hydrocarbon group having 2 to 10 carbon atoms. The lower limit of the number of carbon atoms of $L^1$ is 2, the upper limit of the same is 10, preferably 8 or 6, and the range of the same is, for example, 2 to 8, 2 to 6. The number of carbon atoms of $L^1$ is preferably 2. The lower limit of the number of carbon atoms of $L^2$ is 2, the upper limit of the same is 10, preferably 8 or 6, and the range of the same is, for example, 2 to 8, 2 to 6. The number of carbon atoms of $L^2$ is preferably 2. Specific examples of $L^1$ and $L^2$ include an ethylene group (—$CH_2$—$CH_2$—), a vinylene group (—CH=CH—), a propylene group (—$CH_2$—$CH_2$—$CH_2$—), an isopropylene group (—$CH_2$—CH($CH_3$)-), a butylene group (—$CH_2$—$CH_2$—$CH_2$—$CH_2$—), a methylbutylene group (—$CH_2$—CH($CH_3$)—$CH_2$—$CH_2$—), a dimethylbutylene group (—$CH_2$—CH($CH_3$)—CH($CH_3$)—$CH_2$—), an ethylbutylene group (—$CH_2$—CH($C_2H_5$)—$CH_2$—$CH_2$—), a pentylene group (—$CH_2$—$CH_2$—$CH_2$—$CH_2$—$CH_2$—), a hexylene group (—$CH_2$—$CH_2$—$CH_2$—$CH_2$—$CH_2$—$CH_2$—), a heptylene group (—$CH_2$—$CH_2$—$CH_2$—$CH_2$—$CH_2$—$CH_2$—$CH_2$—), and an octylene group (—$CH_2$—$CH_2$—$CH_2$—$CH_2$—$CH_2$—$CH_2$—$CH_2$—$CH_2$—). $L^1$ is preferably a vinylene group (—CH=CH—). $L^2$ is preferably an ethylene group (—$CH_2$—$CH_2$—). $L^1$ and $L^2$ may be the same hydrocarbon group or different hydrocarbon groups. As a specific example of the latter, $L^1$ is preferably a vinylene group (—CH=CH—), and $L^2$ is preferably an ethylene group (—$CH_2$—$CH_2$—).

In the chemical formula (1), $X^1$ and $X^2$ are each independently an imino group (—$NR^1$—), an ether group (—O—), or a thioether group (—S—). In the imino group, the $R^1$ is a hydrogen atom or a straight-chain or branched, saturated or unsaturated hydrocarbon group having 2 to 10 carbon atoms and is preferably a hydrogen atom. The description of $L^1$ and $L^2$ can be incorporated in the description of the straight-chain or branched, saturated or unsaturated hydrocarbon group having 2 to 10 carbon atoms by reference. $X^1$ is preferably an imino group (—$NR^1$—). $X^2$ is preferably an imino group (—$NR^1$—). $X^1$ and $X^2$ may be the same substituent or different substituents. As a specific example of the former, $X^1$ and $X^2$ is preferably an imino group (—$NR^1$—) and more preferably an NH group.

In the chemical formula (1), the atomic group having a sugar skeleton at a nucleoside residue is not particularly limited, and examples thereof include atomic groups having sugar skeletons on known natural or artificial nucleoside residues. Examples of the atomic group having a sugar skeleton at a natural nucleoside residue include an atomic group having a ribose skeleton at a ribonucleoside residue and an atomic group having a deoxyribose skeleton on a deoxyribonucleoside. The atomic group having a sugar skeleton at an artificial nucleoside residue can be, for example, an atomic group having a bicyclic sugar skeleton at an artificial nucleoside residue, and specific examples thereof can be an atomic group having a ribose skeleton where an oxygen atom at 2'-position and a carbon atom at 4' position of ENA (2'-O,4'-C-Ethylene-bridged Nucleic Acids) or LNA (Locked Nucleic Acid) is crosslinked. The atomic group having a sugar phosphate skeleton at a nucleotide residue is not particularly limited, and examples thereof include atomic groups having sugar phosphate skeletons at known natural or artificial nucleotide residues. Examples of the atomic group having a sugar phosphate skeleton at a natural nucleotide residue include an atomic group having a ribose phosphate skeleton at a ribonucleotide residue and an atomic group having a deoxyribose phosphate skeleton on a deoxyribonucleotide. The atomic group having a sugar phosphate skeleton at an artificial nucleoside residue can be, for example, an atomic group having a bicyclic sugar phosphate skeleton at an artificial nucleoside residue, and specific examples thereof can be an atomic group having a ribose phosphate skeleton where an oxygen atom at 2'-position and a carbon atom at 4' position of 2'-O,4'-C-Ethylene-bridged Nucleic Acids (ENA) or Locked Nucleic Acid (LNA) is crosslinked.

In the chemical formula (1), an atomic group having a sugar skeleton at a nucleoside residue or an atomic group having a sugar phosphate skeleton at a nucleotide residue is represented by preferably the following chemical formula (2).

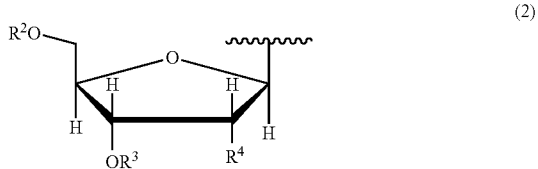

(2)

In the chemical formula (2), $R^2$ is a hydrogen atom, a protecting group, or a group represented by the following chemical formula (3), $R^3$ is a hydrogen atom, a protecting group, or a phosphoramidite group, $R^4$ is a hydrogen atom, a fluorine atom, a hydroxyl group, an amino group, or a mercapto group, and

(3)

in the chemical formula (3), Y is an oxygen atom or a sulfur atom, Z is a hydroxyl group or an imidazole group, and m is an integer of 1 to 10.

In the chemical formula (2), $R^2$ is a hydrogen atom, a protecting group, or a group represented by the following chemical formula (3). The protecting group is not particularly limited and can be, for example, a protecting group of a known hydroxyl group used in nucleic acid synthesis methods, and as a specific example, the protecting group can be an DMTr group (4,4'-dimethoxy(triphenylmethyl) group). When $R^2$ is a group represented by the chemical formula (3), the nucleoside derivative of the present invention can also be referred to as a nucleotide derivative, for example.

In the chemical formula (2), $R^3$ is a hydrogen atom, a protecting group, or a phosphoramidite group. The protecting group is not particularly limited, and, the description of $R^2$ can be incorporated in the description of the protecting group by reference, for example. The phosphoramidite group is represented by the chemical formula (5). When $R^3$ is a phosphoramidite group, the nucleoside derivative of the present invention can also be referred to as a phosphoramidite compound of the nucleoside derivative, for example. When $R^2$ is a group represented by the chemical formula (3), and $R^3$ is a phosphoramidite group, the nucleoside derivative of the present invention can also be referred to as, for example, a phosphoramidite compound of the nucleotide derivative.

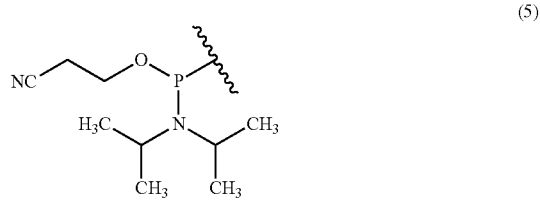 [SMILES: *P(OCCC#N)N(C(C)C)C(C)C]

(5)

In the chemical formula (2), $R^4$ is a hydrogen atom, a fluorine atom, a hydroxyl group, an amino group, or a mercapto group and is preferably a hydrogen atom or a hydroxyl group. When $R^4$ is a hydrogen atom, the nucleoside derivative of the present invention has a deoxyribose skeleton as a sugar skeleton and can be used for, for example, synthesis of DNAs. When $R^4$ is a hydroxyl group, the nucleoside derivative of the present invention has a ribose skeleton as a sugar skeleton and can be used for, for example, synthesis of RNAs.

In the chemical formula (3), Y is an oxygen atom or a sulfur atom. When Y is an oxygen atom, polynucleotide including, as a building block, the nucleoside derivative of the present invention can also be referred to as polynucleotide having a phosphodiester bond. When Y is a sulfur atom, polynucleotide including, as a building block, the nucleoside derivative of the present invention can also be referred to as polynucleotide having a phosphorothioate bond.

In the chemical formula (3), Z is a hydroxyl group or an imidazole group. In the imidazole group, imidazole is bound to a phosphate atom via a nitrogen atom at the 1-position, for example.

In the chemical formula (3), m is an integer of 1 to 10, preferably 1 to 3, 1 to 2, or 1.

The nucleoside derivative of the present invention is represented by preferably the following chemical formula (4), (6), (7), or (8). The respective nucleoside derivatives represented by the following chemical formulae (4), (6), (7), and (8) are also referred to as MK4, MK1, MK2, and MK3.

(4)
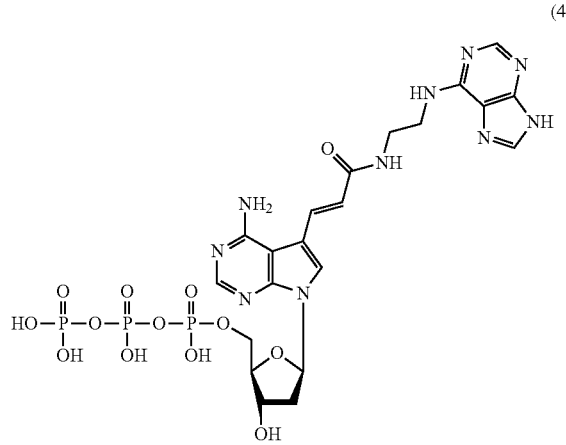

(6)
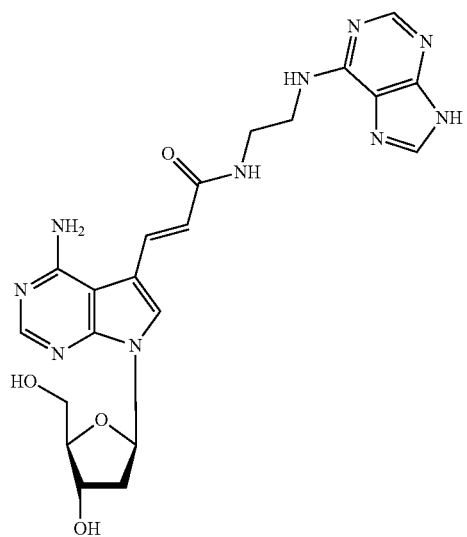

(7)
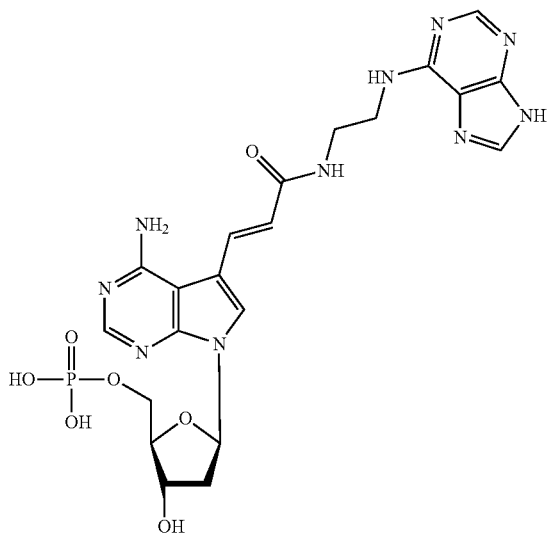

(8)
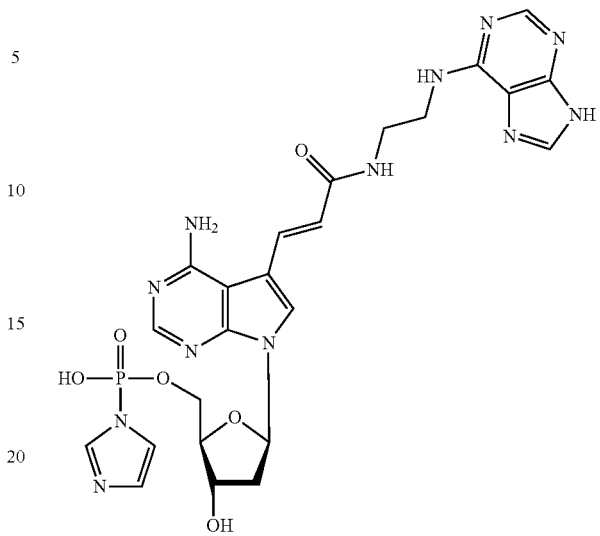

The nucleoside derivative or a salt thereof of the present invention may be a stereoisomer such as enantiomers, tautomers, geometric isomers, conformers, and optical isomers thereof, and salts thereof. Specifically, in the chemical formula (2) and chemical formulae described below, the sugar skeleton is D body, but the nucleoside derivative of the present invention is not limited thereto, and the sugar skeleton may be L body.

The salt of the nucleoside derivative of the present invention may be an acid addition salt or a base addition salt. Further, acid which forms the acid addition salt may be an inorganic acid or an organic acid, and base which forms the base addition salt may be an inorganic base or an organic base. The inorganic acid is not particularly limited, and examples thereof include sulfuric acid, phosphoric acid, hydrofluoric acid, hydrochloric acid, hydrobromic acid, hydroiodic acid, hypofluorous acid, hypochlorous acid, hypobromous acid, hypoiodous acid, fluorous acid, chlorous acid, bromous acid, iodous acid, fluorine acid, chloric acid, bromic acid, iodine acid, perfluoric acid, perchloric acid, perbromic acid, and periodic acid. The organic acid is not particularly limited, and examples thereof include p-toluenesulfonic acid, methanesulfonic acid, oxalic acid, p-bromobenzenesulfonic acid, carbonic acid, succinic acid, citric acid, benzoic acid, and acetic acid. The inorganic base is not particularly limited, and examples thereof include ammonium hydroxides, alkali metal hydroxides, alkaline earth metal hydroxides, carbonates, and bicarbonates. More specific examples thereof include sodium hydroxide, potassium hydroxide, potassium carbonate, sodium carbonate, sodium bicarbonate, potassium hydrogen carbonate, calcium hydroxide, and calcium carbonate. The organic base is not particularly limited, and examples thereof include ethanolamine, triethylamine, and tris(hydroxymethyl)aminomethane.

The method for producing the nucleoside derivative of the present invention is not particularly limited, and the nucleoside derivative of the present invention can be produced by combining known synthesis methods. As a specific example, the nucleoside derivative of the present invention can be synthesized by, for example, an amidation reaction between a nucleoside derivative into which an acrylic acid structure is introduced and an adenine in which a substituent having an amino group at a terminal thereof is substituted with a hydrogen atom of an amino group, as in the synthetic method of the example described below.

(Polynucleotide Synthesis Reagent)

The polynucleotide synthesis reagent (hereinafter also referred to as "synthesis reagent") of the present invention contains a nucleotide derivative or a salt thereof including the nucleoside derivative or a salt thereof of the present invention, as mentioned above. The synthesis reagent of the present invention is characterized by containing the nucleoside derivative of the present invention, and other composition and conditions are not particularly limited. The description of the nucleoside derivative or a salt thereof of the present invention can be incorporated in the description of the synthesis reagent of the present invention by reference, for example. The synthesis reagent of the present invention can be described with reference to the description of the polynucleotide of the present invention, for example.

In the synthesis reagent of the present invention, the nucleoside derivative preferably contains at least one of the phosphoramidite compound or the nucleotide derivative, for example.

The synthesis reagent of the present invention may further contain another reagent for use in synthesis of polynucleotide, for example.

(Method for Producing Polynucleotide)

The method for producing a polynucleotide of the present invention includes, as mentioned above, the step of synthesizing a polynucleotide using a nucleotide derivative or a salt thereof including the nucleoside derivative or a salt thereof of the present invention. The method for producing a polynucleotide of the present invention is characterized by using a nucleotide derivative or a salt thereof including the nucleoside derivative or a salt thereof of the present invention in the synthesis step, and other steps and conditions are not particularly limited. The descriptions of the nucleoside derivative or a salt thereof and the synthesis reagent of the present invention can be incorporated in the method for producing a polynucleotide of the present invention by reference, for example. By the method for producing a polynucleotide of the present invention, the polynucleotide of the present invention to be described below can be produced, for example.

In the method for producing a polynucleotide of the present invention, the synthesis reagent of the present invention may be used as the nucleotide derivative or a salt thereof including the nucleoside derivative or a salt thereof of the present invention.

In the synthesis step, the method for synthesizing the polynucleotide is not particularly limited, and the polynucleotide can be synthesized by a known polynucleotide synthesis method. When the phosphoramidite compound is used as the nucleotide derivative or a salt thereof, the polynucleotide can be synthesized by a phosphoramidite method in the synthesis step.

The method for producing the polynucleotide of the present invention may further include a step of purifying the polynucleotide obtained in the synthesis step, for example. The purification method in the purification step is not particularly limited, and the polynucleotide can be purified by a known purification method such as column chromatography.

(Polynucleotide)

As mentioned above, the polynucleotide of the present invention includes, as a building block, a nucleotide derivative or a salt thereof including the nucleoside derivative or a salt thereof of the present invention. The method for producing a polynucleotide of the present invention is characterized by using a nucleotide derivative or a salt thereof including the nucleoside derivative or a salt thereof of the present invention in the synthesis step, and other steps and conditions are not particularly limited. The descriptions of the nucleoside derivative or a salt thereof, the polynucleotide synthesis reagent, and the method for producing a polynucleotide of the present invention can be incorporated in the description of the polynucleotide of the present invention by reference, for example. With the polynucleotide of the present invention, a binding nucleic acid molecule that binds to a target can be produced, for example, as mentioned below. In the polynucleotide of the present invention, the building block means, for example, a part of the polynucleotide.

The polynucleotide of the present invention has a structure represented by the following chemical formula (9), for example. The description of each substituent can be incorporated in the description of each substituent in the chemical formula (9) by reference, for example.

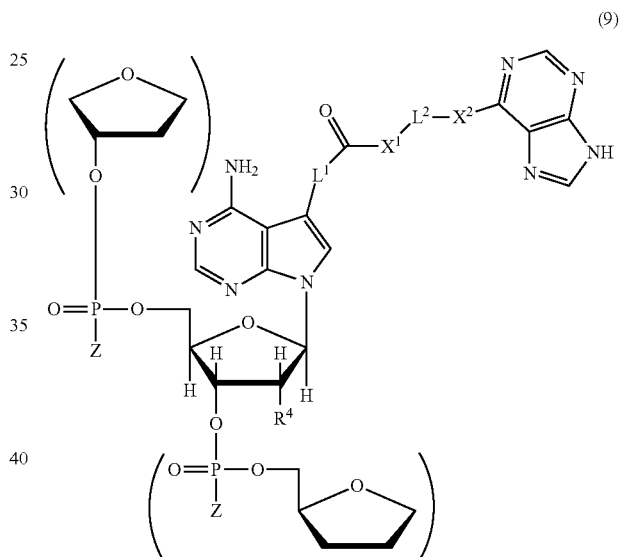

(9)

The polynucleotide of the present invention can be, for example, a binding nucleic acid molecule that binds to a target. The target is not particularly limited and can be any target, and as a specific example, the target can be a biomolecule. Examples of the biomolecule include secretory immunoglobulin A (sIgA), an amylase (e.g., α-amylase), chromogranin A, β-defensin (Defensin) 2, β-defensin 4A, kallikrein, C-reactive proteins (CRPs), calprotectin, Statherins, cortisol, melatonin, lysozyme, lactate dehydrogenase (LDH)5, and interleukin (IL)-6. The binding nucleic acid molecule can be produced by the method for producing a binding nucleic acid molecule of the present invention to be described below.

The polynucleotide of the present invention may further include, for example, other nucleotide in addition to the nucleotide derivative. Examples of the nucleotide include deoxyribonucleotide and ribonucleotide. Examples of the polynucleotide of the present invention include DNA consisting of deoxyribonucleotide only, DNA/RNA including deoxyribonucleotide and ribonucleotide, and RNA consisting of ribonucleotide only. Other nucleotide may be, for example, a modified nucleotide.

Examples of the modified nucleotide include modified deoxyribonucleotide and modified ribonucleotide. The modified nucleotide can be, for example, a nucleotide with a modified sugar. Examples of the sugar include deoxyribose and ribose. The modified site in the nucleotide is not particularly limited, and may be, for example, the 2'-position or the 4'-position of the sugar. Examples of the modification include methylation, fluorination, amination, and thiation. The modified nucleotide can be, for example, a modified nucleotide with a pyrimidine base (pyrimidine nucleus) as a base or a modified nucleotide with a purine base (purine nucleus) as a base and is preferably the former. Hereinafter, a nucleotide with a pyrimidine base is referred to as pyrimidine nucleotide, the pyrimidine nucleotide modified is referred to as modified pyrimidine nucleotide, a nucleotide with a purine base is referred to as purine nucleotide, and the purine nucleotide modified is referred to as modified purine nucleotide. Examples of the pyrimidine nucleotide include an uracil nucleotide with uracil, cytosine nucleotide with cytosine, and thymine nucleotide with thymine. When the base in the modified nucleotide is a pyrimidine base, it is preferable that the 2'-position and/or the 4'-position of the sugar is modified, for example. Specific examples of the modified nucleotide include modified nucleotides with the 2'-position of the ribose being modified, such as a 2'-methylated-uracil nucleotide, 2'-methylated-cytosine nucleotide, 2'-fluorinated-uracil nucleotide, 2'-fluorinated-cytosine nucleotide, 2'-aminated-uracil nucleotide, 2'-aminated-cytosine nucleotide, 2'-thiated-uracil nucleotide, and 2'-thiated-cytosine nucleotide.

The base in the other nucleotide may be, for example, a natural base (non-artificial base) such as adenine (A), cytosine (C), guanine (G), thymine (T), and uracil (U), or a non-natural base (artificial base). Examples of the artificial base include modified bases and altered bases. The artificial base preferably has the same function as the natural base (A, C, G, T, or U). Example of the artificial base having the same function as the natural base include artificial bases capable of binding to cytosine (C) instead of guanine (G), capable of binding to guanine (G) instead of cytosine (C), capable of binding to thymine (T) or uracil (U) instead of adenine (A), capable of binding to adenine (A) instead of thymine (T), and capable of binding to adenine (A) instead of uracil (U). The modified base is not particularly limited, and may be, for example, a methylated base, a fluorinated base, aminated base, and thiated base. Specific examples of the modified base include 2'-methyluracil, 2'-methylcytosine, 2'-fluorouracil, 2'-fluorocytosine, 2'-aminouracil, 2'-aminocytosine, 2'-thiouracil, and 2'-thiocytosine. In the present invention, for example, the bases represented by A, G, C, T, and U include the meaning of, in addition to the natural bases, the artificial bases having the same functions as the natural bases.

The polynucleotide of the present invention may further include, for example, an artificial nucleic acid monomer in addition to the nucleotide derivative. Examples of the artificial nucleic acid monomer include peptide nucleic acids (PNAs), LNAs, and ENAs. The base in the monomer residue is the same as described above, for example.

The length of the polynucleotide of the present invention is not particularly limited, and the lower limit thereof is, for example, 10-mer, 20-mer, or 25-mer, the upper limit thereof is, for example, 150-mer, 100-mer, or 70-mer, and the range thereof is, for example, 10- to 150-mer, 20- to 100-mer, or 25- to 70-mer.

The polynucleotide of the present invention may further include an additional sequence, for example. Preferably, the additional sequence is bound to at least one of the 5' end or the 3' end, more preferably to the 3' end of the polynucleotide, for example. The additional sequence is not particularly limited, and the length thereof is also not particularly limited.

The polynucleotide of the present invention may further include a labeling substance, for example. Preferably, the labeling substance is bound to at least one of the 5' end or the 3' end, more preferably to the 5' end of the polynucleotide, for example. The labeling substance is not particularly limited, and examples thereof include fluorescent substances, dyes, isotopes, and enzymes. Examples of the fluorescent substances include pyrenes, TAMRA, fluorescein, Cy®3 dyes, Cy®5 dyes, FAM dyes, rhodamine dyes, Texas Red dyes, fluorophores such as JOE, MAX, HEX, and TYE, and examples of the dyes include Alexa dyes such as Alexa®488 and Alexa®647.

The labeling substance may, for example, be linked directly to the nucleic acid molecule or linked indirectly via the additional sequence.

The polynucleotide of the present invention can be used in the state where it is immobilized on a carrier, for example. It is preferable to immobilize either the 5' end or the 3' end, more preferably the 3' end of the polynucleotide of the present invention, for example. When the polynucleotide of the present invention is immobilized, the polynucleotide may be immobilized either directly or indirectly on the carrier, for example. In the latter case, it is preferable to immobilize the nucleic acid molecule via the additional sequence, for example.

(Method for Producing Binding Nucleic Acid Molecule)

The method for producing a binding nucleic acid molecule of the present invention includes, as mentioned above, the steps of: causing a candidate polynucleotide and a target to come into contact with each other; and selecting the candidate polynucleotide bound to the target as a binding nucleic acid molecule that binds to the target, and the candidate polynucleotide is the polynucleotide of the present invention. The method for producing a binding nucleic acid molecule of the present invention is characterized in that the candidate polynucleotide is the polynucleotide of the present invention, for example, and other steps, conditions, etc. are not particularly limited. The descriptions of the nucleoside derivative or a salt thereof, the synthesis reagent, the method for producing polynucleotide, and the polynucleotide can be incorporated in the method for producing a binding nucleic acid of the present invention by reference, for example. In the method for producing a binding nucleic acid molecule of the present invention, the candidate polynucleotide includes, as a building block, a nucleotide derivative or a salt thereof including the nucleoside derivative or a salt thereof of the present invention. Thus, for example, a binding nucleic acid molecule that exhibits excellent binding ability to a target can be produced by the method for producing a binding nucleic acid molecule of the present invention.

As to the binding nucleic acid molecule of the present invention, the contact step and the selection step can be performed by the SELEX method, for example.

The number of candidate polynucleotides in the contact step is not particularly limited, and the number of candidate polynucleotides in the contact step is, for example, $4^{20}$ to $4^{120}$ types (about $10^{12}$ to $10^{72}$) and $4^{30}$ to $4^{60}$ types (about $10^{18}$ to $10^{36}$).

In the contact step, a candidate polynucleotide and a target are caused to come into contact with each other. Then, by the contact, the candidate polynucleotide and the target are reacted to form a complex between the candidate polynucleotide and the target. The target to be used in the contact step may be, for example, the target itself or a decomposition product thereof. The conditions under which the candidate polynucleotide and the target are bound are not particularly limited, and for example, the binding can be performed by incubating the both in a solvent for a certain period of time. The solvent is not particularly limited, and for example, a solvent in which the binding of the both is retained is preferable, and specific examples thereof include various buffer solutions.

Next, in the selecting step, a candidate polynucleotide bound to the target is selected as a binding nucleic acid molecule that binds to the target. Specifically, a candidate polynucleotide that forms a complex with the target is collected as the binding nucleic acid molecule. A mixture of the candidate polynucleotide and the target after the contact step contains, in addition to the complex, a candidate polynucleotide that is not involved in formation of the complex, for example. Thus, it is preferable that the complex and unreacted candidate polynucleotide are separated from each other from the mixture, for example. The separation method is not particularly limited and can be, for example, a method utilizing a difference in adsorbability between the target and the candidate polynucleotide or a difference in molecular weight between the complex and the candidate polynucleotide.

In addition to this method, the separation method can be, for example, a method using a target immobilized on a carrier in formation of the complex. That is, the target is immobilized on a carrier in advance to contact between the carrier and the candidate polynucleotide, thereby forming a complex the immobilized target and the candidate polynucleotide. An unreacted candidate polynucleotide that does not bind to the immobilized target is then removed, and the complex between the target and the candidate polynucleotide is dissociated from the carrier. The method for immobilizing the target on a carrier is not particularly limited and can be carried out by a known method. The carrier is not particularly limited, and, a known carrier can be used.

In the above-described manner, the binding nucleic acid molecule that binds to a target can be produced.

The method for producing a binding nucleic acid molecule of the present invention may further include, for example, the step of determining a base sequence of the selected binding nucleic acid molecule. The method for determining the base sequence is not particularly limited, and the base sequence can be determined by a known base sequence determination method.

In the method for producing a binding nucleic acid molecule of the present invention, for example, one set of the contact step and the selection step may be performed for two or more cycles in total, and a specific example thereof is 3 to 15 cycles.

(α-amylase-Binding Nucleic Acid Molecule)

The α-amylase-binding nucleic acid molecule (hereinafter also referred to as "α-amylase nucleic acid molecule") of the present invention includes the following polynucleotide (a):

(a) a polynucleotide (a1):

(a1) a polynucleotide consisting of any of base sequences of SEQ ID NOs: 1 and 11 to 16.

The α-amylase nucleic acid molecule of the present invention can bind to α-amylase, as mentioned above. The α-amylase is not particularly limited, and the α-amylase may be derived from a human or a non-human animal, for example. Examples of the non-human animal include mice, rats, monkeys, rabbits, dogs, cats, horses, cows, and pigs.

Amino acid sequence information on human α-amylase is registered under Accession No. P04745 in UniProt (http://www.uniprot.org/), for example.

In the present invention, the expression "binds to α-amylase" (and grammatical variations thereof) is also referred to as "has binding ability to α-amylase" or "has binding activity to α-amylase", for example. The binding between the nucleic acid molecule of the present invention and the α-amylase can be determined by surface plasmon resonance (SPR) analysis or the like, for example. The analysis can be performed using ProteON (trade name, BioRad), for example. Since the α-amylase nucleic acid molecule of the present invention binds to α-amylase, it can be used for detection of the α-amylase, for example.

As mentioned above, the α-amylase nucleic acid molecule of the present invention comprises the following polynucleotide (a):

(a) a polynucleotide (a1):

(a1) a polynucleotide consisting of any of base sequences of SEQ ID NOs: 1 and 11 to 16.

α-amylase-binding nucleic acid molecule 1
(SEQ ID NO: 1)
5'-GGTTTGGACGCAATCTCCCTAATCTAGTGACGAAAATGTACGAG
GGGGTCATTTGAAACTACAATGGGCGGGCTTATC-3'

α-amylase-binding nucleic acid molecule 2
(SEQ ID NO: 11)
5'-GGTTTGGACGCAATCTCCCTAATCTAGTGACGAAAATGTACGAG
GGGGTCATTTGAAACTA-3'

α-amylase-binding nucleic acid molecule 3
(SEQ ID NO: 12)
5'-GCAATCTCCCTAATCTAGTGACGAAAATGTACGAGGGGGTCATT
TGAAACTA-3'

α-amylase-binding nucleic acid molecule 4
(SEQ ID NO: 13)
55'-GGTTTGGACGCAATCTCCCTAATCAGACTATTATTTCAAGTAC
GTGGGGGTCTTGAAACTACAATGGGCGGGCTTATC-3'

α-amylase-binding nucleic acid molecule 5
(SEQ ID NO: 14)
5'-GGTTTGGACGCAATCTCCCTAATCTAAAGTTTCTAAACGATGTG
GCGGCATTCAGAAACTACAATGGGCGGGCTTATC-3'

α-amylase-binding nucleic acid molecule 6
(SEQ ID NO: 15)
5'-GGTTTGGACGCAATCTCCCTAATCTAAAGTTTCTAAACGATGTG
GCGGCATTCAGAAACT-3'

α-amylase-binding nucleic acid molecule 7
(SEQ ID NO: 16)
5'-GCAATCTCCCTAATCTAAAGTTTCTAAACGATGTGGCGGCATTC
AGAAACT-3''

The polynucleotide (a) above also includes, for example, the meaning of the polynucleotide of (a2), (a3), or (a4) below:

(a2) a polynucleotide consisting of a base sequence obtained by deletion, substitution, insertion, and/or addition of one or more bases in any of the base sequences of the polynucleotide (a1) and binds to the α-amylase;

(a3) a polynucleotide consisting of a base sequence having at least 80% sequence identity to any of the base sequences of the polynucleotide (a1) and binds to the α-amylase; and (a4) a polynucleotide consisting of a base sequence complementary to a polynucleotide hybridizing to any of the base sequences of the polynucleotide (a1) under stringent conditions and binds to the α-amylase.

Regarding the polynucleotide (a2), the term "one or more" is not limited as long as, for example, it is in the range where the polynucleotide (a2) binds to α-amylase. The number of the "one or more" bases is, for example, 1 to 15, 1 to 10, 1 to 7, 1 to 5, 1 to 3, 1 or 2, or 1. In the present invention, the numerical range regarding the number of bases, sequences, or the like discloses, for example, all the positive integers falling within that range. That is, for example, the description "one to five bases" discloses all of "one, two, three, four, and five bases" (the same applies hereinafter).

Regarding the polynucleotide (a3), the "sequence identity" is not limited as long as, for example, it is in the range where the polynucleotide (a3) binds to α-amylase. The sequence identity is, for example, at least 80%, at least 85%, at least 90%, at least 95%, at least 96%, at least 97%, at least 98%, or at least 99%. The sequence identity can be calculated with analysis software such as BLAST or FASTA using default parameters, for example (the same applies hereinafter).

Regarding the polynucleotide (a4), the "polynucleotide hybridizing to" may be, for example, a polynucleotide that is perfectly or partially complementary to the polynucleotide (a1) and binds to the α-amylase. The hybridization can be detected by various types of hybridization assay, for example. The hybridization assay is not particularly limited, and for example, a method described in "Molecular Cloning: A Laboratory Manual $2^{nd}$ Ed." edited by Sambrook et al. (Cold Spring Harbor Laboratory Press (1989)) or the like can be employed.

Regarding the polynucleotide (a4), the "stringent conditions" may be any of low stringency conditions, medium stringency conditions, and high stringency conditions, for example. The "low stringency conditions" are, for example, conditions where 5×SSC, 5×Denhardt's solution, 0.5% SDS, and 50% formamide are used at 32° C. The "medium stringency conditions" are, for example, conditions where 5×SSC, 5×Denhardt's solution, 0.5% SDS, and 50% formamide are used at 42° C. The "high stringency conditions" are, for example, conditions where 5×SSC, 5×Denhardt's solution, 0.5% SDS, and 50% formamide, are used at 50° C. Those skilled in the art can set the degree of stringency by, for example, setting the conditions such as the temperature, the salt concentration, the concentration and length of a probe, the ionic strength, the time, etc. as appropriate. As the "stringent conditions", it is also possible to employ conditions described in the above-described "Molecular Cloning: A Laboratory Manual $2^{nd}$ Ed." edited by Sambrook et al. (Cold Spring Harbor Laboratory Press (1989)) or the like, for example.

In the α-amylase nucleic acid molecule of the present invention, the building blocks of the polynucleotide are, for example, nucleotide residues, examples of which include deoxyribonucleotide residues and ribonucleotide residues. The polynucleotide is, for example, a DNA consisting of deoxyribonucleotide residues or a DNA including a deoxyribonucleotide residue(s) and a ribonucleotide residue(s), and the polynucleotide may further include a non-nucleotide residue(s), as mentioned below. The α-amylase-binding nucleic acid molecule of the present invention may be also referred to as "α-amylase aptamer" hereinafter, for example.

The α-amylase nucleic acid molecule of the present invention may consist of any of the above-described polynucleotides, or may include any of the above-described polynucleotides, for example. In the latter case, the α-amylase nucleic acid molecule of the present invention may include, for example, two or more polynucleotides selected from the above-described polynucleotides, as mentioned below. The two or more polynucleotides may be the polynucleotides with the same sequence or different sequences.

Also, in the latter case, the α-amylase nucleic acid molecule of the present invention may further include a linker(s) and/or an additional sequence(s), for example. The linker is a sequence present between polynucleotides, for example. The additional sequence is a sequence added to an end, for example.

When the α-amylase nucleic acid molecule of the present invention includes, for example, a plurality of polynucleotides selected from the above-described polynucleotides, it is preferable that the plurality of polynucleotide sequences are linked to each other to form a single-stranded polynucleotide. The plurality of polynucleotide sequences may be linked to each other directly, or may be linked to each other indirectly with a linker, for example. It is preferable that the polynucleotide sequences are linked to each other directly or indirectly at their ends. When the α-amylase nucleic acid molecule of the present invention includes the plurality of polynucleotide sequences, the number of the sequences is not particularly limited, and is, for example, 2 or more, 2 to 20, 2 to 10, or 2 or 3.

The length of the linker is not particularly limited, and is, for example, 1- to 200-mer, 1- to 20-mer, 3- to 12-mer, or 5- to 9-mer. The building blocks of the linker are, for example, nucleotide residues, examples of which include deoxyribonucleotide residues and ribonucleotide residues. The linker is not particularly limited, and examples thereof include polynucleotides such as a DNA consisting of deoxyribonucleotide residues and a DNA including a ribonucleotide residue(s). Specific examples of the linker include polydeoxythymine (poly[dT]), polydeoxyadenine (poly[dA]), and poly(dA-dT) having a repetitive sequence composed of A and T. Preferably, the linker is poly(dT) or poly(dA-dT).

In the α-amylase nucleic acid molecule of the present invention, the polynucleotide is preferably a single-stranded polynucleotide. It is preferable that the single-stranded polynucleotide can form a stem structure and a loop structure by self-annealing, for example. It is preferable that the polynucleotide can form a stem-loop structure, an internal loop structure, and/or a bulge structure, for example.

The α-amylase nucleic acid molecule of the present invention may be a double strand, for example. When the α-amylase nucleic acid molecule is a double strand, for example, one of single-stranded polynucleotides includes the polynucleotide (a), and the other single-stranded polynucleotide is not limited. The other single-stranded polynucleotide may be, for example, a polynucleotide including a base sequence complementary to the polynucleotide (a). When the α-amylase nucleic acid molecule of the present invention is a double strand, it is preferable to dissociate the double strand to single-stranded polynucleotides by denaturation or the like before use, for example. Also, it is preferable that the dissociated single-stranded polynucleotide including the polynucleotide (a) is forming a stem structure and a loop structure as mentioned above, for example.

In the present invention, the expression "can form a stem structure and a loop structure" encompasses that, for example, a stem structure and a loop structure are formed actually, and also, even if a stem structure and a loop structure are not formed, they can be formed depending on conditions. The expression "can form a stem structure and a loop structure (and grammatical variations thereof)" encompasses, for example, both the cases where the formation thereof has been confirmed through an experiment and where the formation thereof is predicted through simulation using a computer or the like.

The building blocks of the α-amylase nucleic acid molecule of the present invention are, for example, nucleotide residues. Examples of the nucleotide residues include deoxyribonucleotide residues and ribonucleotide residues. The α-amylase nucleic acid molecule of the present invention may be, for example, a DNA consisting of deoxyribonucleotide residues only or a DNA including one or more ribonucleotide residues. In the latter case, "one or more" is not particularly limited. For example, the number of the ribonucleotide residues in the polynucleotide is, for example, 1 to 91, 1 to 30, 1 to 15, 1 to 7, 1 to 3, or 1 or 2.

The polynucleotide may include, as a base in a nucleotide residue, a natural base or a modified base. The natural base (non-artificial base) is not particularly limited, and may be, for example, a purine base with a purine skeleton or a pyrimidine base with a pyrimidine skeleton. The purine base is not particularly limited, and examples thereof include adenine (A) and guanine (G). The pyrimidine base is not particularly limited, and examples thereof include cytosine (C), thymine (T), and uracil (U). Among them, cytosine (C) and thymine (T) are preferable.

When the polynucleotide includes the modified base(s), the site and the number of the modified bases are not particularly limited. When the polynucleotide (a) has the modified base(s), some or all of the underlined adenines in the polynucleotide consisting of any of base sequences of SEQ ID NOs: 1 and 11 to 16 are modified bases, for example. When the underlined adenine is the modified base, the modified base is a modified purine base, which is a purine base modified with a modifying group.

The modified base is a base modified with a modifying group, for example. The base to be modified with the modifying group (also referred to simply as the "base to be modified" hereinafter) is the natural base, for example. The natural base is not particularly limited, and may be, for example, a purine base or a pyrimidine base. The modified base is not particularly limited, and may be, for example, a modified adenine, a modified guanine, a modified cytosine, a modified thymine, or a modified uracil.

In the modified base, the base to be modified may be modified with the modifying group either directly or indirectly, for example. In the latter case, the base to be modified may be modified with the modifying group via a linker, for example. The linker is not particularly limited.

In the base to be modified, a site to be modified with the modifying group is not particularly limited. When the base is a purine base, the modified site in the purine base may be, for example, the 7-position or the 8-position, preferably the 7-position of the purine skeleton. When the modified site in the purine base is the 7-position of the purine skeleton, the nitrogen atom at the 7-position is preferably substituted with a carbon atom. When the base is a pyrimidine base, the modified site in the pyrimidine base may be, for example, the 5-position or the 6-position, preferably the 5-position of the pyrimidine skeleton. Thymine has a methyl group bound to carbon at the 5-position. Thus, when the 5-position of the pyrimidine base is modified, for example, the modifying group may be bound to the carbon at the 5-position either directly or indirectly, or the modifying group may be bound to carbon in the methyl group bound to the carbon at the 5-position either directly or indirectly. When the pyrimidine skeleton has "=O" bound to carbon at the 4-position and a group that is not "—CH$_3$" or "—H" bound to carbon at the 5-position, the modified base can be referred to as a modified uracil or a modified thymine.

When the modified base is a modified purine base, the modifying group is preferably an adenine residue. That is, the modified purine base is a base modified with an adenine residue, for example. In the base to be modified, a site to be modified with the adenine residue (binding site of the adenine residue to the base to be modified) is not particularly limited, and can be, for example, an amino group that binds to carbon at the 6-position of the adenine residue. The base to be modified with the adenine residue is not particularly limited, and is preferably purine base, for example, and it is preferable that atom at the 7-position of the purine base is modified with the adenine residue. When the modified base is a modified thymine base, the modifying group is preferably an adenine residue or a guanine base. That is, the modified base is, for example, a base modified with an adenine residue or a guanine residue. In the base to be modified, a site to be modified with the adenine residue is not particularly limited, and can be, for example, an amino group that binds to carbon at the 6-position of the adenine residue. In the base to be modified, a site to be modified with the guanine residue is not particularly limited, and can be, for example, an amino group that binds to carbon at the 2-position of the guanine residue. The base to be modified with the adenine residue or the guanine residue is not particularly limited, and is preferably a thymine, for example, and it is preferable that carbon in a methyl group bound to the carbon at the 5-position of the thymine is modified with the adenine residue or the guanine residue.

When the modifying group is the adenine residue or the guanine residue, it is preferable that, for example, the base to be modified is modified with the modifying group via the linker, as shown below.

[nucleotide residue]-[linker]-[adenine residue]

[nucleotide residue]-[linker]-[guanine residue]

The linker is not particularly limited, and can be represented by, for example, each formula present between the nucleotide residue and the adenine residue/guanine residue, as shown below. It is to be noted, however, that the linker is not limited thereto. In each formula, the numerical value "n" in (CH$_2$)$_n$ is 1 to 10, 2 to 10, or 2, for example.

[nucleotide residue]=C—C(=O)—NH—(CH$_2$)$_n$-[adenine residue]

[nucleotide residue]=C—C(=O)—NH—(CH$_2$)$_n$-[guanine residue]

[nucleotide residue]C=C—C(=O)—NH—(CH$_2$)$_n$-[adenine residue]

[nucleotide residue]=C—C(=O)—NH—CH$_2$—CH$_2$-[adenine residue]

[nucleotide residue]=C—C(=O)—NH—CH$_2$—CH$_2$-[guanine residue]

[nucleotide residue]-C=C—C(=O)—NH—CH$_2$—CH$_2$-[adenine residue]

In each formula, one ends of the linker [=C] and [—C] form a double bond and a single bond with carbon of the base to be modified in the nucleotide residue, respectively, for example, and the other end of the linker [CH$_2$—] is bound to amine (—NH) in the guanine residue or the adenine residue, for example.

Specific examples of an adenosine nucleotide residue modified with the adenine residue in the polynucleotide include a residue represented by the following chemical formula (10) (also referred to as "nucleotide residue of MK4" hereinafter). It is to be noted, however, that the present invention is not limited thereto.

(10)

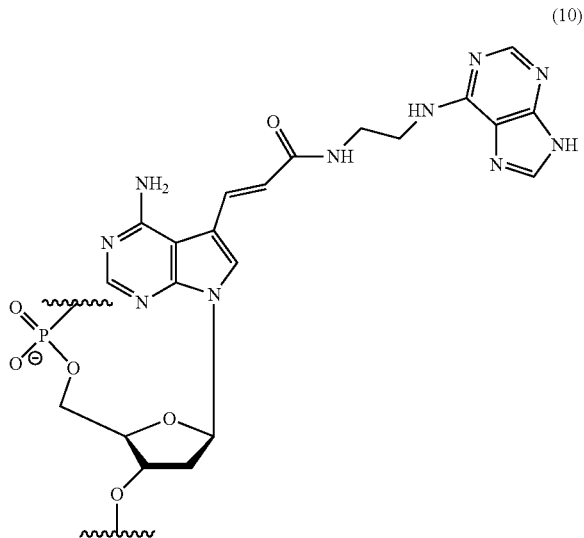 [SMILES: *O[C@@H]1C[C@H](n2cc(/C=C/C(=O)NCCNc3ncnc4[nH]cnc34)c3c(N)ncnc32)O[C@@H]1COP(*)(=O)[O-]]

In the polynucleotide consisting of any of base sequences of SEQ ID NOs: 1 and 11 to 16, it is more preferable that the underlined adenine is a nucleotide residue of the MK4.

When the α-amylase nucleic acid molecule of the present invention includes the nucleotide residues of the MK4, the polynucleotide can be synthesized using, as a monomer molecule, a nucleotide triphosphate represented by the following chemical formula (4) (hereinafter also referred to as "MK4 monomer" hereinafter), for example. In the synthesis of the polynucleotide, for example, the monomer molecule binds to another nucleotide triphosphate via a phosphodiester bond. A method for producing the MK4 monomer is described below.

Other examples of the modifying group include a methyl group, a fluoro group, an amino group, a thio group, a benzylaminocarbonyl group, a tryptaminocarbonyl group, and an isobutylaminocarbonyl group.

Specific examples of the modified adenine include 7'-deazaadenine. Specific examples of the modified guanine include 7'-deazaguanine. Specific examples of the modified cytosine include 5'-methylcytosine (5-Me-dC). Specific examples of the modified thymine include 5'-benzylaminocarbonyl thymine, 5'-tryptaminocarbonyl thymine, and 5'-isobutylaminocarbonyl thymine. Specific examples of the modified uracil include 5'-benzylaminocarbonyl uracil (BndU), 5'-tryptaminocarbonyl uracil (TrpdU), and 5'-isobutylaminocarbonyl uracil. The modified uracils given above as examples can be also referred to as modified thymines.

The polynucleotide may include only one type or two or more types of the modified bases, for example.

The α-amylase nucleic acid molecule of the present invention may include a modified nucleotide, for example. The modified nucleotide may be a nucleotide having the above-described modified base, a nucleotide having a modified sugar obtained through modification of a sugar residue, or a nucleotide having the modified base and the modified sugar.

The sugar residue is not particularly limited, and may be a deoxyribose residue or a ribose residue, for example. The modified site in the sugar residue is not particularly limited, and may be, for example, the 2'-position or the 4'-position of the sugar residue. Either one or both of the 2'-position and the 4'-position may be modified. Examples of a modifying group in the modified sugar include a methyl group, a fluoro group, an amino group, a thio group.

When the base in the modified nucleotide residue is a pyrimidine base, it is preferable that the 2'-position and/or the 4'-position of the sugar residue is modified, for example. Specific examples of the modified nucleotide residue include modified nucleotide residues with the 2'-position of the deoxyribose residue or ribose residue being modified, such as a 2'-methylated-uracil nucleotide residue, 2'-methylated-cytosine nucleotide residue, 2'-fluorinated-uracil nucleotide residue, 2'-fluorinated-cytosine nucleotide residue, 2'-aminated-uracil nucleotide residue, 2'-aminated-cytosine nucleotide residue, 2'-thiated-uracil nucleotide residue, and 2'-thiated-cytosine nucleotide residue.

The number of the modified nucleotides is not particularly limited. For example, the number of the modified nucleotides in the polynucleotide is, for example, 1 to 100, 1 to 90, 1 to 80, or 1 to 70. Also, the number of the modified nucleotides in the full-length nucleic acid molecule including the polynucleotide is not particularly limited, and is, for example, 1 to 91, 1 to 78, or in the numerical ranges given above as examples of the number of the modified nucleotides in the polynucleotide.

The α-amylase nucleic acid molecule of the present invention may include, for example, one or more artificial nucleic acid monomer residues. The term "one or more" is not particularly limited, and may be, for example, 1 to 100, 1 to 50, 1 to 30, or 1 to 10 in the polynucleotide, for example. Examples of the artificial nucleic acid monomer residue include peptide nucleic acids (PNAs), locked nucleic acids (LNAs), and 2'-O,4'-C-ethylenebridged nucleic acids (ENAs). The nucleic acid in the monomer residue is the same as described above, for example.

It is preferable that the α-amylase nucleic acid molecule of the present invention is resistant to nuclease, for example. In order to allow the α-amylase nucleic acid molecule of the present invention to have nuclease resistance, it is preferable that the nucleic acid molecule of the present invention includes the modified nucleotide residue(s) and/or the artificial nucleic acid monomer residue(s), for example. Also, in order to allow the α-amylase nucleic acid molecule of the present invention to have nuclease resistance, the nucleic acid molecule of the present invention may have polyethylene glycol (PEG) of several tens of kDa, deoxythymidine, or the like bound to, e.g., the 5' end or the 3' end thereof.

The α-amylase nucleic acid molecule of the present invention may further include an additional sequence, for example. Preferably, the additional sequence is bound to at least one of the 5' end and the 3' end, more preferably to the 3' end of the nucleic acid molecule, for example. The additional sequence is not particularly limited. The length of the additional sequence is not particularly limited, and is, for example, 1- to 200-mer, 1- to 50-mer, 1- to 25-mer, or 18- to 24-mer. The building blocks of the additional sequence are, for example, nucleotide residues, examples of which include deoxyribonucleotide residues and ribonucleotide residues. The additional sequence is not particularly limited, and examples thereof include polynucleotides such as a DNA consisting of deoxyribonucleotide residues and a DNA including a ribonucleotide residue(s). Specific examples of the additional sequence include poly(dT) and poly(dA).

The α-amylase nucleic acid molecule of the present invention can be used in the state where it is immobilized on a carrier, for example. It is preferable to immobilize either the 5' end or the 3' end, more preferably the 3' end of the α-amylase nucleic acid molecule of the present invention, for example. When the α-amylase nucleic acid molecule of the present invention is immobilized, the α-amylase nucleic acid molecule may be immobilized either directly or indirectly on the carrier, for example. In the latter case, it is preferable to immobilize the α-amylase nucleic acid molecule via the additional sequence, for example.

The method for producing the α-amylase nucleic acid molecule of the present invention is not particularly limited. For example, the α-amylase nucleic acid molecule of the present invention can be synthesized by known methods such as: nucleic acid synthesis methods utilizing chemical synthesis; and genetic engineering procedures.

The α-amylase nucleic acid molecule of the present invention exhibits binding properties to the α-amylase, as mentioned above. Thus, use of the α-amylase nucleic acid molecule of the present invention is not particularly limited, as long as it is the use utilizing the binding properties of the α-amylase nucleic acid molecule to the α-amylase. The α-amylase nucleic acid molecule of the present invention can be used in various methods as an alternative to, e.g., an antibody against the α-amylase.

(α-amylase Analysis Sensor)

The α-amylase analysis sensor of the present invention is a sensor for analyzing α-amylase and includes the α-amylase-binding nucleic acid molecule of the present invention. It is only required that the α-amylase analysis sensor of the present invention includes the α-amylase-binding nucleic acid molecule of the present invention, and other configurations, conditions, etc. are not particularly limited. By using the α-amylase analysis sensor of the present invention, the α-amylase can be detected by, for example, causing the α-amylase nucleic acid molecule to bind to the α-amylase. The description of the α-amylase-binding nucleic acid molecule of the present invention can be incorporated in the description of the α-amylase analysis sensor of the present invention by reference, for example.

The α-amylase analysis sensor of the present invention may be configured so that, for example, it further includes a carrier, and the α-amylase-binding nucleic acid molecule is disposed on the carrier. Preferably, the α-amylase-binding nucleic acid molecule is immobilized on the carrier. The immobilization of the α-amylase-binding nucleic acid molecule on the carrier is as described above, for example. The method for using the α-amylase analysis sensor of the present invention is not particularly limited, and the description of the α-amylase nucleic acid molecule of the present invention and the following description of the method for analyzing α-amylase of the present invention can be incorporated in the description of the α-amylase analysis sensor of the present invention by reference.

(Method for Analyzing α-amylase)

The method for analyzing α-amylase of the present invention includes the step of causing a specimen and a nucleic acid molecule to come into contact with each other to detect α-amylase in the specimen, the nucleic acid molecule is the α-amylase-binding nucleic acid molecule of the present invention, and in the detection step, the nucleic acid molecule is caused to bind to the α-amylase in the specimen, and the α-amylase in the specimen is detected by detecting the binding. The method for analyzing α-amylase of the present invention is characterized in that it uses the α-amylase nucleic acid molecule of the present invention, and other steps, conditions, etc. are not particularly limited. In the method for analyzing α-amylase of the present invention, the α-amylase analysis sensor of the present invention may be used as the α-amylase nucleic acid molecule of the present invention. The descriptions of the α-amylase-binding nucleic acid molecule and the α-amylase analysis sensor of the present invention can be incorporated in the description of the method for analyzing α-amylase of the present invention by reference, for example.

The nucleic acid molecule of the present invention specifically binds to α-amylase. Thus, according to the present invention, it is possible to specifically detect α-amylase in a specimen by detecting the binding between the α-amylase and the nucleic acid molecule, for example. Specifically, since the present invention can analyze the presence or absence or the amount of α-amylase in a specimen, for example, it can be said that the present invention can also perform qualitative or quantitative analysis of the α-amylase.

In the present invention, the specimen is not particularly limited. Examples of the specimen include saliva, urine, plasma, and serum.

The specimen may be a liquid specimen or a solid specimen, for example. The specimen is preferably a liquid specimen from the viewpoint of ease of handling because the liquid specimen can be caused to come into contact with the nucleic acid molecule more easily, for example. In the case of the solid specimen, a liquid mixture, a liquid extract, a solution, or the like of the solid specimen prepared using a solvent may be used, for example. The solvent is not particularly limited, and may be water, physiological saline, or a buffer solution, for example.

The above-described detection step includes, for example: a contact step of causing the specimen and the nucleic acid molecule to come into contact with each other to cause the nucleic acid molecule to bind to the α-amylase in the specimen; and a binding detection step of detecting the binding between the α-amylase and the nucleic acid molecule. The detection step may further include, for example, the step of analyzing the presence or absence or the amount of the α-amylase in the specimen on the basis of the result obtained in the binding detection step.

In the contact step, the method for causing the specimen and the nucleic acid molecule to come into contact with each other is not particularly limited. The contact between the specimen and the nucleic acid molecule preferably is achieved in a liquid, for example. The liquid is not particularly limited, and may be, for example, water, physiological saline, or a buffer solution.

In the contact step, the conditions under which the contact between the specimen and the nucleic acid molecule is caused are not particularly limited. The contact temperature is, for example, 4° C. to 37° C., or 18° C. to 25° C., and the contact time is, for example, 10 to 120 minutes or 30 to 60 minutes.

In the contact step, the nucleic acid molecule may be an immobilized nucleic acid molecule immobilized on a carrier or an unimmobilized nucleic acid molecule in a free state, for example. In the latter case, the nucleic acid molecule is caused to come into contact with the specimen in a container, for example. The nucleic acid molecule is preferably the immobilized nucleic acid molecule from the viewpoint of favorable handleability, for example. The carrier is not particularly limited, and may be, for example, a substrate, beads, or a container. The container may be a microplate or a tube, for example. The immobilization of the nucleic acid molecule is as described above, for example.

The binding detection step is the step of detecting the binding between the α-amylase in the specimen and the nucleic acid molecule, as mentioned above. By detecting the presence or absence of the binding between the α-amylase and the nucleic acid molecule, it is possible to analyze the presence or absence of the α-amylase in the specimen (qualitative analysis), for example. Also, by detecting the degree of the binding (the binding amount) of the α-amylase to the nucleic acid molecule, it is possible to analyze the amount of the α-amylase in the specimen (quantitative analysis), for example.

In the case where the binding between the α-amylase and the nucleic acid molecule cannot be detected, it can be determined that no α-amylase is present in the specimen. In the case where the binding is detected, it can be determined that the α-amylase is present in the specimen.

The method for analyzing the binding between the α-amylase and the nucleic acid molecule is not particularly limited. A conventionally known method for detecting the binding between substances may be employed as the method, for example, and specific examples of the method include the above-described SPR. Detection of the binding may be detection of a complex of the α-amylase and the nucleic acid molecule, for example.

(α-amylase Detection Kit)

A α-amylase detection kit of the present invention includes the α-amylase-binding nucleic acid molecule of the present invention. It is only required that the α-amylase detection kit of the present invention includes the α-amylase-binding nucleic acid molecule of the present invention, and other configurations, conditions, etc. are not particularly limited. By using the α-amylase detection kit of the present invention, it is possible to perform the detection and the like of the α-amylase as mentioned above, for example. The descriptions of the α-amylase-binding nucleic acid molecule, the α-amylase analysis sensor, and the method for analyzing α-amylase of the present invention can be incorporated in the description of the α-amylase detection kit by reference, for example.

The α-amylase detection kit of the present invention may include the α-amylase analysis sensor of the present invention as the α-amylase nucleic acid molecule of the present invention, for example. The α-amylase detection kit of the present invention may further include any component(s) in addition to the α-amylase nucleic acid molecule of the present invention, for example. Examples of the component include the above-described carrier, a buffer solution, and instructions for use.

(BDN4A-binding Nucleic Acid Molecule)

The β-defensin (BDN)4A-binding nucleic acid molecule (hereinafter also referred to as "BDN4A nucleic acid molecule") of the present invention includes the following polynucleotide (b):
(b) a polynucleotide (b1):
(b1) a polynucleotide consisting of any of base sequences of SEQ ID NOs: 4 to 6.

The descriptions of the α-amylase-binding nucleic acid molecule, the α-amylase analysis sensor, the method for analyzing α-amylase, and the α-amylase detection kit can be incorporated in the description of the BDN4A-binding nucleic acid molecule of the present invention by reference, by, for example, reading "α-amylase" as "BDN4A", reading "(a)" as "(b)", reading "(a1)" as "(b1)", reading "(a2)" as "(b2)", reading "(a3)" as "(b3)", reading "(a4)" as "(b4)", and reading "SEQ ID NOs: 1 and 11 to 16" as "SEQ ID NOs: 4 to 6", unless otherwise specifically stated. The same applies to the descriptions of the BDN4A analysis sensor, the method for analyzing BDN4A, and the BDN4A detection kit, to be described below.

The BDN4A nucleic acid molecule of the present invention can bind to BDN4A, as mentioned above. The BDN4A is not particularly limited, and the BDN4A may be derived from a human or a non-human animal, for example. Examples of the non-human animal include mice, rats, monkeys, rabbits, dogs, cats, horses, cows, and pigs. Amino acid sequence information on human BDN4A is registered under Accession No. 015263 in UniProt (http://www.uniprot.org/), for example.

In the present invention, the expression "binds to BDN4A" (and grammatical variations thereof) is also referred to as "has binding ability to BDN4A" or "has binding activity to BDN4A", for example. The binding between the BDN4A-binding nucleic acid molecule of the present invention and the BDN4A can be determined by surface plasmon resonance (SPR) analysis or the like, for example. The analysis can be performed using ProteON (trade name, BioRad), for example. Since the BDN4A nucleic acid molecule of the present invention binds to BDN4A, it can be used for detection of the BDN4A, for example.

As mentioned above, the BDN4A nucleic acid molecule of the present invention includes the following polynucleotide (b):
(b) a polynucleotide (1):
(b1) a polynucleotide consisting of any of base sequences of SEQ ID NOs: 4 to 6.

```
BDN4A-binding nucleic acid molecule 1
                                      (SEQ ID NO: 4)
5'-GGTTACACGAGCCGCACATTTCTATTTTTACGGGGTATAGTTCT
CTGAGGAGGAGTTCCCAGGCGAAGTTGTTATC-3'

BDN4A-binding nucleic acid molecule 2
                                      (SEQ ID NO: 5)
5'-CGAGCCGCACATTTCTATTTTTACGGGGTATAGTTCTCTGAGGA
GGAGTTCCCAGGCGAAGTTGTTATC-3'

BDN4A-binding nucleic acid molecule 3
                                      (SEQ ID NO: 6)
5'-GGTTACACGAGCCGCACATTTCACCGTGATAGTTCTCTGAGGAG
GACTTCTAGAGTTCCCAGGCGAAGTTGTTATC-3'
```

The polynucleotide (b) above also includes, for example, the meaning of the polynucleotide of (b2), (b3), or (b4) below:
(b2) a polynucleotide consisting of a base sequence obtained by deletion, substitution, insertion, and/or addition of one or more bases in any of the base sequences of the polynucleotide (b1) and binds to the BDN4A.
(b3) a polynucleotide consisting of a base sequence having at least 80% sequence identity to any of the base sequences of the polynucleotide (b1) and binds to the BDN4A.
(b4) a polynucleotide consisting of a base sequence complementary to a polynucleotide hybridizing to any of the base sequences of the polynucleotide (b1) under stringent conditions and binds to the BDN4A.

(BDN4A Analysis Sensor)

The β-defensin (BDH)4A analysis sensor of the present invention is a sensor for analyzing β-defensin (BDN)4A and includes the BDN4A-binding nucleic acid molecule of the present invention. It is only required that the BDN4A analysis sensor of the present invention includes the BDN4A-binding nucleic acid molecule of the present invention, and other configurations, conditions, etc. are not particularly limited. By using the BDN4A analysis sensor of the present invention, the BDN4A can be detected by, for example, causing the BDN4A nucleic acid molecule to bind to the BDN4A. The description of the BDN4A-binding nucleic acid molecule of the present invention can be incorporated in the description of the BDN4A analysis sensor of the present invention by reference, for example. The method for using the BDN4A analysis sensor of the present invention is not particularly limited, and the description of the BDN4A-binding nucleic acid molecule of the present invention and the following description of the method for analyzing BDN4A of the present invention can be incorporated in the description of the BDN4A analysis sensor of the present invention by reference.

(Method for Analyzing BDN4A)

The method for analyzing β-defensin (BDH)4A of the present invention includes the step of causing a specimen and a nucleic acid molecule to come into contact with each other to detect β-defensin (BDN)4A in the specimen, the nucleic acid molecule is the BDN4A-binding nucleic acid molecule of the present invention, and in the detection step, the nucleic acid molecule is caused to bind to the BDN4A in the specimen, and the BDN4A in the specimen is detected by detecting the binding. The method for analyzing BDN4A of the present invention is characterized in that it uses the BDN4A-binding nucleic acid molecule of the present invention, and other steps, conditions, etc. are not particularly limited. In the method for analyzing BDN4A of the present invention, the BDN4A analysis sensor of the present invention may be used as the BDN4A nucleic acid molecule of the present invention. The descriptions of the BDN4A-binding nucleic acid molecule and the BDN4A analysis sensor of the present invention can be incorporated in the description of the method for analyzing BDN4A of the present invention by reference, for example.

(BDN4A Detection Kit)

The β-defensin (BDN)4A detection kit of the present invention includes the BDN4A-binding nucleic acid molecule of the present invention. It is only required that the BDN4A detection kit of the present invention includes the BDN4A-binding nucleic acid molecule of the present invention, and other configurations, conditions, etc. are not particularly limited. By using the BDN4A detection kit of the present invention, it is possible to perform the detection and the like of the BDN4A as mentioned above, for example. The descriptions of the BDN4A-binding nucleic acid molecule, the BDN4A analysis sensor, and the method for analyzing BDN4 of the present invention can be incorporated in the description of the BDN4A detection kit of the present invention by reference.

(Lysozyme-binding Nucleic Acid Molecule)

The lysozyme binding nucleic acid molecule (hereinafter also referred to as a "lysozyme nucleic acid molecule") of the present invention includes the following polynucleotide (1):
(1) a polynucleotide (11):
(11) a polynucleotide consisting of any of base sequences of SEQ ID NOs: 7 to 9.

The descriptions of the α-amylase-binding nucleic acid molecule, the α-amylase analysis sensor, the method for analyzing α-amylase, and the α-amylase detection kit can be incorporated in the description of the lysozyme-binding nucleic acid molecule of the present invention by reference, by, for example, reading "α-amylase" as "lysozyme", reading "(a)" as "(1)", reading "(a1)" as "(11)", reading "(a2)" as "(12)", reading "(a3)" as "(13)", reading "(a4)" as "(14)", and reading "SEQ ID NOs: 1 and 11 to 16" as "SEQ ID NOs: 7 to 9", unless otherwise specifically stated. The same applies to the descriptions of the lysozyme analysis sensor, the method for analyzing lysozyme, and the lysozyme detection kit, to be described below.

The lysozyme nucleic acid molecule of the present invention can bind to lysozyme, as mentioned above. The lysozyme is not particularly limited, and the lysozyme may be derived from a human or a non-human animal, for example. Examples of the non-human animal include mice, rats, monkeys, rabbits, dogs, cats, horses, cows, and pigs. Amino acid sequence information on human lysozyme is registered under Accession No. P61626 in UniProt (http://www.uniprot.org/), for example.

In the present invention, the expression "binds to lysozyme" (and grammatical variations thereof) is also referred to as "has binding ability to lysozyme" or "has binding activity to lysozyme", for example. The binding between the lysozyme nucleic acid molecule of the present invention and the lysozyme can be determined by surface plasmon resonance (SPR) analysis or the like, for example. The analysis can be performed using ProteON (trade name, BioRad), for example. Since the lysozyme nucleic acid molecule of the present invention binds to lysozyme, it can be used for detection of the lysozyme, for example.

As mentioned above, the lysozyme nucleic acid molecule of the present invention includes the following polynucleotide (1):
(1) a polynucleotide (11):
(11) a polynucleotide consisting of any of base sequences of SEQ ID NOs: 7 to 9.

Lysozyme-binding nucleic acid molecule 1
(SEQ ID NO: 7)
5'-GGTTACACGAGCCGCACATTTCTAACGGGAACTTCAACCCATAC
AGTCTTTTGAGTTCCCAGGCGAAGTTGTTATC-3'

Lysozyme-binding nucleic acid molecule 2
(SEQ ID NO: 8)
5'-CGAGCCGCACATTTCTAACGGGAACTTCAACCCATACAGTCTTT
TGAGTTCCC-3'

Lysozyme-binding nucleic acid molecule 3
(SEQ ID NO: 9)
5'-GGTTACACGAGCCGCACATTTCTTTACTCCGGAACCCATACAGT
CTTTTCCGGAGTTCCCAGGCGAAGTTGTTATC-3'

The polynucleotide (1) above also includes, for example, the meaning of the polynucleotide of (12), (13), or (14) below:
(12) a polynucleotide consisting of a base sequence obtained by deletion, substitution, insertion, and/or addition of one or more bases in any of the base sequences of the polynucleotide (11) and binds to the lysozyme.
(13) a polynucleotide consisting of a base sequence having at least 80% sequence identity to any of the base sequences of the polynucleotide (11) and binds to the lysozyme.
(14) a polynucleotide consisting of a base sequence complementary to a polynucleotide hybridizing to any of the base sequences of the polynucleotide (11) under stringent conditions and binds to the lysozyme.

(Lysozyme Analysis Sensor)

The lysozyme analysis sensor of the present invention is a sensor for analyzing lysozyme and includes the lysozyme-binding nucleic acid molecule of the present invention. It is only required that the lysozyme analysis sensor of the present invention includes the lysozyme-binding nucleic acid molecule of the present invention, and other configurations, conditions, etc. are not particularly limited. By using the lysozyme analysis sensor of the present invention, the lysozyme can be detected by, for example, causing the lysozyme nucleic acid molecule to bind to the lysozyme. The description of the lysozyme-binding nucleic acid molecule of the present invention can be incorporated in the description of the lysozyme analysis sensor of the present invention by reference, for example. The method for using the lysozyme analysis sensor of the present invention is not particularly limited, and the description of the lysozyme-binding nucleic acid molecule of the present invention and the following description of the method for analyzing lysozyme of the present invention can be incorporated in the description of the lysozyme analysis sensor of the present invention by reference.

(Method for Analyzing Lysozyme)

The method for analyzing lysozyme of the present invention includes the step of causing a specimen and a nucleic acid molecule to come into contact with each other to detect lysozyme in the specimen, the nucleic acid molecule is the lysozyme-binding nucleic acid molecule of the present invention, and in the detection step, the nucleic acid molecule is caused to bind to the lysozyme in the specimen, and the lysozyme in the specimen is detected by detecting the binding. The method for analyzing lysozyme of the present invention is characterized in that it uses the lysozyme-binding nucleic acid molecule of the present invention, and other steps, conditions, etc. are not particularly limited. In the method for analyzing lysozyme of the present invention, the lysozyme analysis sensor of the present invention may be used as the lysozyme nucleic acid molecule of the present invention. The descriptions of the lysozyme-binding nucleic acid molecule and the lysozyme analysis sensor of the present invention can be incorporated in the description of the method for analyzing lysozyme of the present invention by reference, for example.

(Lysozyme Detection Kit)

The lysozyme detection kit of the present invention includes the lysozyme-binding nucleic acid molecule of the present invention. It is only required that the lysozyme detection kit of the present invention includes the lysozyme-binding nucleic acid molecule of the present invention, and other configurations, conditions, etc. are not particularly limited. By using the lysozyme detection kit of the present invention, it is possible to perform the detection and the like of the lysozyme as mentioned above, for example. The descriptions of the lysozyme-binding nucleic acid molecule, the lysozyme analysis sensor, and the method for analyzing lysozyme of the present invention can be incorporated in the description of the lysozyme detection kit by reference, for example.

(LDH5-binding Nucleic Acid Molecule)

The lactate dehydrogenase (LDH)5-binding nucleic acid molecule (hereinafter also referred to as a "LDH5 nucleic acid molecule") of the present invention includes the following polynucleotide (d):

(d) a polynucleotide (d1):
(d1) a polynucleotide consisting of any of base sequences of SEQ ID NOs: 17 to 20.

The descriptions of the α-amylase-binding nucleic acid molecule, the α-amylase analysis sensor, the method for analyzing α-amylase, and the α-amylase detection kit can be incorporated in the description of the LDH5-binding nucleic acid molecule of the present invention by reference, by, for example, reading "α-amylase" as "LDH5", reading "(a)" as "(d)", reading "(a1)" as "(d1)", reading "(a2)" as "(d2)", reading "(a3)" as "(d3)", reading "(a4)" as "(d4)", and reading "SEQ ID NOs: 1 and 11 to 16" as "SEQ ID NOs: 17 to 20", unless otherwise specifically stated. The same applies to the descriptions of the LDH5 analysis sensor, the method for analyzing LDH5, and the LDH5 detection kit, to be described below.

The LDH5 nucleic acid molecule of the present invention can bind to LDH5 as mentioned above. The LDH5 is not particularly limited, and the LDH5 may be derived from a human or a non-human animal, for example. Examples of the non-human animal include mice, rats, monkeys, rabbits, dogs, cats, horses, cows, and pigs. Amino acid sequence information on human LDH5 is registered under Accession No. P00338 in UniProt (http://www.uniprot.org/), for example.

In the present invention, the expression "binds to LDH5" (and grammatical variations thereof) is also referred to as "has binding ability to LDH5" or "has binding activity to LDH5", for example. The binding between the LDH5 nucleic acid molecule of the present invention and the LDH5 can be determined by surface plasmon resonance (SPR) analysis or the like, for example. The analysis can be performed using ProteON (trade name, BioRad), for example. Since the LDH5 nucleic acid molecule of the present invention binds to LDH5, it can be used for detection of the LDH5, for example.

As mentioned above, the LDH5 nucleic acid molecule of the present invention includes the following polynucleotide (d):

(d) a polynucleotide (d1):
(d1) a polynucleotide consisting of any of base sequences of SEQ ID NOs: 17 to 20.

```
LDH5-binding nucleic acid molecule 1
                                    (SEQ ID NO: 17)
5'-GGAATTGACACCTCGCCGTTTATGCTGCTGGCTCGTGAGACGGA
TATCAGGTCTCCTAAGGCTGGCTGGCTACTATAC-3'

LDH5-binding nucleic acid molecule 2
                                    (SEQ ID NO: 18)
5'-GGAATTGACACCTCGCCGTTTATGAGAGGGAGATCATCTCTCTG
GCGGACACAACCTAAGGCTGGCTGGCTACTATAC-3'

LDH5-binding nucleic acid molecule 3
                                    (SEQ ID NO: 19)
5'-ACCTCGCCGTTTATGCTGCTGGCTCGTGAGACGGATATCAGGTC
TCCTAAGGCTGGC-3'

LDH5-binding nucleic acid molecule 4
                                    (SEQ ID NO: 20)
5'-TGCTGCTGGCTCGTGAGACGGATATCAGGTCTCCTAAGGCTGG
C-3'
```

The polynucleotide (d) above also includes, for example, the meaning of the polynucleotide of (d2), (d3), or (d4) below:

(d2) a polynucleotide consisting of a base sequence obtained by deletion, substitution, insertion, and/or addition of one or more bases in any of the base sequences of the polynucleotide (d1) and binds to the LDH5.

(d3) a polynucleotide consisting of a base sequence having at least 80% sequence identity to any of the base sequences of the polynucleotide (d1) and binds to the LDH5.

(d4) a polynucleotide consisting of a base sequence complementary to a polynucleotide hybridizing to any of the base sequences of the polynucleotide (d1) under stringent conditions and binds to the LDH5.

(LDH5 Analysis Sensor)

The LDH5 analysis sensor of the present invention is a sensor for analyzing LDH5 and includes the LDH5-binding nucleic acid molecule of the present invention. It is only required that the LDH5 analysis sensor of the present invention includes the LDH5-binding nucleic acid molecule of the present invention, and other configurations, conditions, etc. are not particularly limited. By using the LDH5 analysis sensor of the present invention, the LDH5 can be detected by, for example, causing the LDH5 nucleic acid molecule to bind to the LDH5. The description of the LDH5-binding nucleic acid molecule of the present invention can be incorporated in the description of the LDH5 analysis sensor of the present invention by reference, for example. The method for using the LDH5 analysis sensor of the present invention is not particularly limited, and the description of the LDH5-binding nucleic acid molecule of the present invention and the following description of the method for analyzing LDH5 of the present invention can be incorporated in the description of the LDH5 analysis sensor of the present invention by reference.

(Method for Analyzing LDH5)

The method for analyzing LDH5 of the present invention includes the step of causing a specimen and a nucleic acid molecule to come into contact with each other to detect LDH5 in the specimen, the nucleic acid molecule is the LDH5-binding nucleic acid molecule of the present invention, and in the detection step, the nucleic acid molecule is caused to bind to the LDH5 in the specimen, and the LDH5 in the specimen is detected by detecting the binding. The method for analyzing LDH5 of the present invention is characterized in that it uses the LDH5-binding nucleic acid molecule of the present invention, and other steps, conditions, etc. are not particularly limited. In the method for analyzing LDH5 of the present invention, the LDH5 analysis sensor of the present invention may be used as the LDH5 nucleic acid molecule of the present invention. The descriptions of the LDH5-binding nucleic acid molecule and the LDH5 analysis sensor of the present invention can be incorporated in the description of the method for analyzing LDH5 of the present invention by reference, for example.

(LDH5 Detection Kit)

The LDH5 detection kit of the present invention includes the LDH5-binding nucleic acid molecule of the present invention. It is only required that the LDH5 detection kit of the present invention includes the LDH5-binding nucleic acid molecule of the present invention, and other configurations, conditions, etc. are not particularly limited. By using the LDH5 detection kit of the present invention, it is possible to perform the detection and the like of the LDH5 as mentioned above, for example. The descriptions of the LDH5-binding nucleic acid molecule, the LDH5 analysis sensor, and the method for analyzing LDH5 of the present invention can be incorporated in the description of the LDH5 detection kit of the present invention by reference.

(IL-6-binding nucleic acid molecule)

The interleukin (IL)-6-binding nucleic acid molecule (hereinafter also referred to as "IL-6 nucleic acid molecule") of the present invention includes the following polynucleotide (i):
(i) a polynucleotide (i1):
(i1) a polynucleotide consisting of any of base sequences of SEQ ID NOs: 21 and 22.

The descriptions of the α-amylase-binding nucleic acid molecule, the α-amylase analysis sensor, the method for analyzing α-amylase, and the α-amylase detection kit can be incorporated in the description of the IL-6-binding nucleic acid molecule of the present invention by reference, by, for example, reading "α-amylase" as "IL-6", reading "(a)" as "(i)", reading "(a1)" as "(i1)", reading "(a2)" as "(i2)", reading "(a3)" as "(i3)", reading "(a4)" as "(i4)", and reading "SEQ ID NOs: 1 and 11 to 16" as "SEQ ID NOs: 21 and 22", unless otherwise specifically stated. The same applies to the descriptions of the IL-6 analysis sensor, the method for analyzing IL-6, and the IL-6 detection kit, to be described below.

The IL-6 nucleic acid molecule of the present invention can bind to IL-6, as mentioned above. The IL-6 is not particularly limited, and the IL-6 may be derived from a human or a non-human animal, for example. Examples of the non-human animal include mice, rats, monkeys, rabbits, dogs, cats, horses, cows, and pigs. Amino acid sequence information on human IL-6 is registered under Accession No. P05231 in UniProt (http://www.uniprot.org/), for example.

In the present invention, the expression "binds to IL-6" (and grammatical variations thereof) is also referred to as "has binding ability to IL-6" or "has binding activity to IL-6", for example. The binding between the IL-6 nucleic acid molecule of the present invention and the IL-6 can be determined by surface plasmon resonance (SPR) analysis or the like, for example. The analysis can be performed using ProteON (trade name, BioRad), for example. Since the IL-6 nucleic acid molecule of the present invention binds to IL-6, it can be used for detection of the IL-6, for example.

As mentioned above, the IL-6 nucleic acid molecule of the present invention includes the following polynucleotide (i):
(i) a polynucleotide (i1):
(i1) a polynucleotide consisting of any of base sequences of SEQ ID NOs: 21 and 22.

```
IL-6-binding nucleic acid molecule 1
                                    (SEQ ID NO: 21)
5'-GGAATTGACACCTCGCCGTTTATGAGTTCAATGGTATTGTATCG
ACTCTTCTCGCCTAAGGCTGGCTGGCTACTATAC-3'

IL-6-binding nucleic acid molecule 2
                                    (SEQ ID NO: 22)
5'-ACCTCGCCGTTTATGAGTTCAATGGTATTGTATCGACTCTTCT
C-3'
```

The polynucleotide (i) above also includes, for example, the meaning of the polynucleotide of (i2), (i3), or (i4) below.
(i2) a polynucleotide consisting of a base sequence obtained by deletion, substitution, insertion, and/or addition of one or more bases in any of the base sequences of the polynucleotide (i1) and binds to the IL-6.
(i3) a polynucleotide comprising a base sequence having 80% or more identity to the base sequence of any one of the above (i1) and binds to IL-6.
(i4) a polynucleotide consisting of a base sequence complementary to a polynucleotide hybridizing to any of the base sequences of the polynucleotide (i1) under stringent conditions and binds to the IL-6.

(IL-6 Analysis Sensor)

The IL-6 analysis sensor of the present invention is a sensor for analyzing IL-6 and includes the IL-6-binding nucleic acid molecule of the present invention. It is only required that the IL-6 analysis sensor of the present invention includes the IL-6-binding nucleic acid molecule of the present invention, and other configurations, conditions, etc. are not particularly limited. By using the IL-6 analysis sensor of the present invention, the IL-6 can be detected by, for example, causing the IL-6 nucleic acid molecule to bind to the IL-6. The description of the IL-6-binding nucleic acid molecule of the present invention can be incorporated in the description of the IL-6 analysis sensor of the present invention by reference, for example. The method for using the IL-6 analysis sensor of the present invention is not particularly limited, and the description of the IL-6-binding nucleic acid molecule of the present invention and the following description of the method for analyzing IL-6 of the present invention can be incorporated in the description of the IL-6 analysis sensor of the present invention by reference.

(Method for Analyzing IL-6)

The method for analyzing IL-6 of the present invention includes the step of causing a specimen and a nucleic acid molecule to come into contact with each other to detect IL-6 in the specimen, the nucleic acid molecule is the IL-6- binding nucleic acid molecule of the present invention, and in the detection step, the nucleic acid molecule is caused to bind to the IL-6 in the specimen, and the IL-6 in the specimen is detected by detecting the binding. The method for analyzing IL-6 of the present invention is characterized in that it uses the IL-6-binding nucleic acid molecule of the present invention, and other steps, conditions, etc. are not particularly limited. In the method for analyzing IL-6 of the present invention, the IL-6 analysis sensor of the present invention may be used as the IL-6 nucleic acid molecule of the present invention. The descriptions of the IL-6-binding nucleic acid molecule and the IL-6 analysis sensor of the present invention can be incorporated in the description of the method for analyzing IL-6 of the present invention by reference, for example.

(IL-6 Detection Kit)

The IL-6 detection kit of the present invention includes the IL-6-binding nucleic acid molecule of the present invention. It is only required that the IL-6 detection kit of the present invention includes the IL-6-binding nucleic acid molecule of the present invention, and other configurations, conditions, etc. are not particularly limited. By using the IL-6 detection kit of the present invention, it is possible to perform the detection and the like of the IL-6 as mentioned above, for example. The descriptions of the IL-6-binding nucleic acid molecule, the IL-6 analysis sensor, and the method for analyzing IL-6 of the present invention can be incorporated in the description of the IL-6 detection kit of the present invention by reference.

EXAMPLES

The present invention is described more specifically below with reference to examples. It is to be noted, however, that the scope of the present invention is not limited by these examples. Commercially available reagents in the examples were used in accordance with their protocols, unless otherwise stated.

Example 1

MK1 to MK4 were prepared by the following synthesis examples.

Electrospray ionization mass spectrometry (ESI-MS) was performed using a mass spectrometer (API2000, vendor: Applied Biosystems) in positive or negative ion mode. $^1$H NMR spectra were obtained using a nuclear magnetic resonance instrument (JNM-ECS400, manufactured by JEOL). Chemical shifts are expressed as relative δ (ppm) to the internal standard, tetramethylsilane (Me$_4$Si). Ion-exchange chromatography was performed using a chromatographic system (ECONO system, manufactured by Bio-Rad). In the ion-exchange chromatography, a glass column (φ25×500 mm) packed with diethylaminoethyl (DEAE) A-25-Sephadex (manufactured by Amershambiosciences) was used.

Synthesis Example 1

Synthesis of MK1

Scheme 1

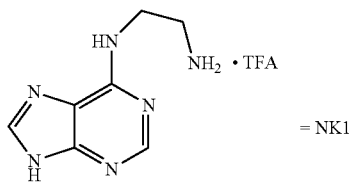

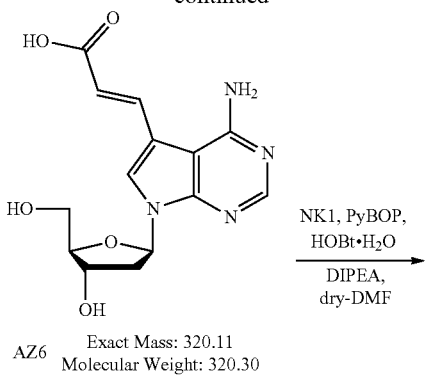

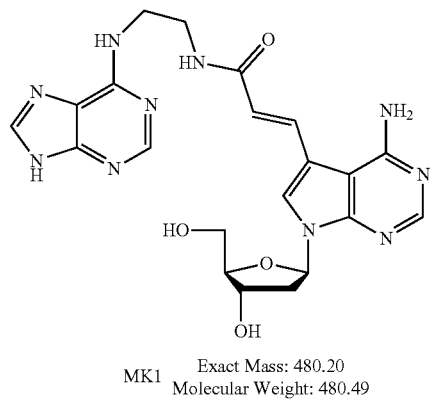

AZ6 (290 mg, 9.06×10$^{-4}$ mol) was dried in vacuo and dissolved in dry-DMF (N,N-dimethylformamide, 3 mL). To this solution, HOBt.H$_2$O (1-hydroxybenzotriazole monohydrate, 176 mg, 1.15×10$^{-5}$ mol, 1.2 eq.), PyBOP® (hexafluorophosphoric acid (benzotriazole-1-yloxy)tripyrrolidinophosphonium, 579 mg, 1.15×10$^{-5}$ mol, 1.2 eq.), and DIPEA (N,N-diisopropylethylamine, 4.6 mL, 2.72×10$^{-2}$ mol, 30 eq.) were added, and NK1 (493 mg, 9.48×10 mol, 1.1 eq.) dissolved in dry-DMF (1 mL) was further added and stirred. After 40 minutes from the initiation of the stirring, the solvent was distilled off under reduced pressure, and a residue was dissolved in water, and a precipitate was collected by suction filtration. The filtrate was roughly purified by reversed-phase column chromatography, to give MK1. Physical properties of MK1 are shown below.

Yield amount: 261 mg, Yield: 60%

ESI-MS (positive ion mode) m/z, found=481.2, calculated for [(M+H)+]=481.2 found=503.1, calculated for [(M+Na)+]=503.2.

$^1$HNMR (400 MHz, DMSO-d6) δ8.22 (1H, m), 8.11 (1H, s), 8.10 (1H, s), 7.87 (1H, s), 7.63 (1H, d), 6.52 (1H, q), 6.35 (1H, d), 5.27 (1H, s), 3.82 (1H, m), 2.18 (1H, m)

Synthesis Example 2

Synthesis of MK2

Scheme 2

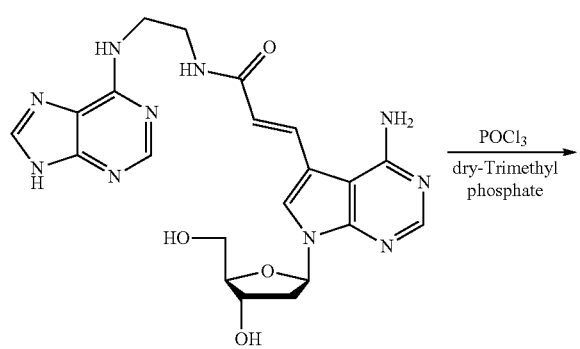

MK1  Exact Mass: 480.20
Molecular Weight: 480.49

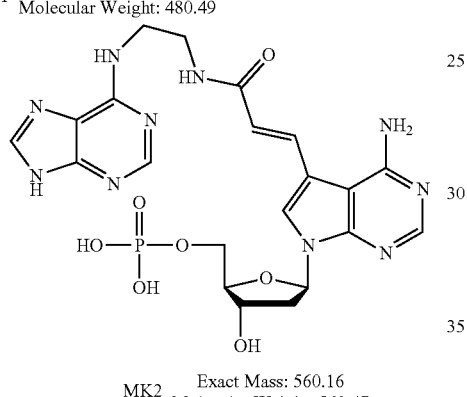

MK2  Exact Mass: 560.16
Molecular Weight: 560.47

MK1 (108 mg, 2.25×10⁴ mol) was dried in vacuo, and the atmosphere was replaced with Ar (Argon). Subsequently, azeotropy between the MK1 and dry-DMF was caused twice (the first time: 40 mL, the second time: 4 mL), and azeotropy between the MK1 and dry-MeCN (acetonitrile) was caused three times (the first time: 9 mL, the second time: 5 mL, the third time: 5 mL). The resultant azeotrope was suspended in dry-Trimethyl phosphate (6 mL), and thereafter, dry-Tributhyl amine (130 μL, 5.44×10⁴ mol, 2.5 eq.) was added thereto. Then, phosphoryl chloride (42 μL, 4.50×10⁴ mol, 2 eq.) was added and stirred under ice cooling. After 40 minutes from the initiation of the stirring, dry-Tributhyl amine (250 μL, 1.05×10⁻³ mol, 5 eq.) and Phosphoryl chloride (84 μL, 4.50×10⁴ mol, 4 eq.) were again added and stirred under ice cooling for 1 hour. After the stirring, a cooled 1 mol/L TEAB (Triethylammonium bicarbonate) buffer (5 mL) was added, stirred for 5 minutes, and quenched. Then, the solvent was distilled off under reduced pressure, crystallization was performed in Ether, and suction filtration was performed to obtain a yellow solid. The yellow solid was dissolved in water, purified by anion-exchange column chromatography, and freeze-dried, to give MK2. Physical properties of MK2 are shown below.

Yield: 30.0 μmol yield: 13.4%

ESI-MS (negative ion mode) m/z, found=559.1, calculated for [(M−H)−]=559.2

Synthesis Example 3

Synthesis of MK3

Scheme 3

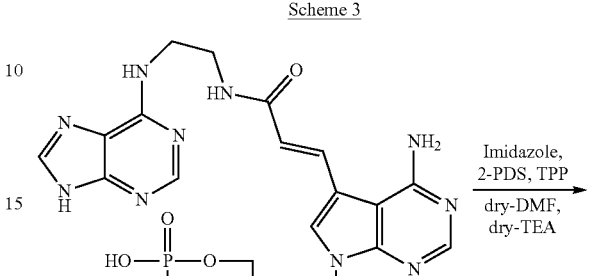

MK2  Exact Mass: 560.16
Molecular Weight: 560.47

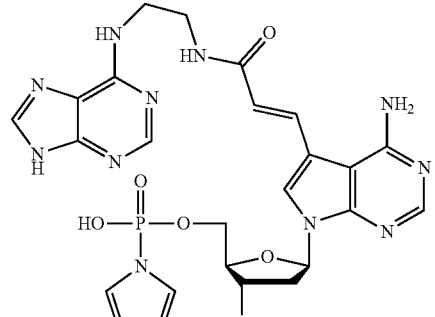

MK3  Exact Mass: 610.19
Molecular Weight: 610.53

MK2 (30.03 μmol) was dried in vacuo, and azeotropy between the MK2 and dry-Pyridine (10 mL) was performed three times, and the azeotrope was dried in vacuo overnight. After the drying, the atmosphere was replaced with Ar, and the MK2 was dissolved in dry-DMF (2 mL) and dry-TEA (triethylamine, 28 μL, 1.98×10⁴ mol, 6.6 eq.). Further, Imidazole (16 mg, 14.02×10⁴ mol, 4 eq.), 2,2'-Dithiodipyridine (17 mg, 7.72×10 mol, 1.6 eq.), and Triphenylphosphine (20 mg, 7.63×10⁴ mol, 1.6 eq.) were added and stirred at room temperature. After 6.5 hours from the initiation of the stirring, the resultant reaction solution was added to a solution of Sodium perchlorate (39 mg, 3.19×10⁴ mol, 10 eq.) in dry-Acetone (18 mL), dry Ether (27 mL), and dry-TEA (2 mL), and allowed to stand at 4° C. for 30 minutes. The precipitate was decanted 5 times with dry-Ether (12 mL) and was thereafter dried in vacuo, to give MK3 as a crude.

Theoretical yield amount: 30.03 μmol

Synthesis Example 4

Synthesis of MK4

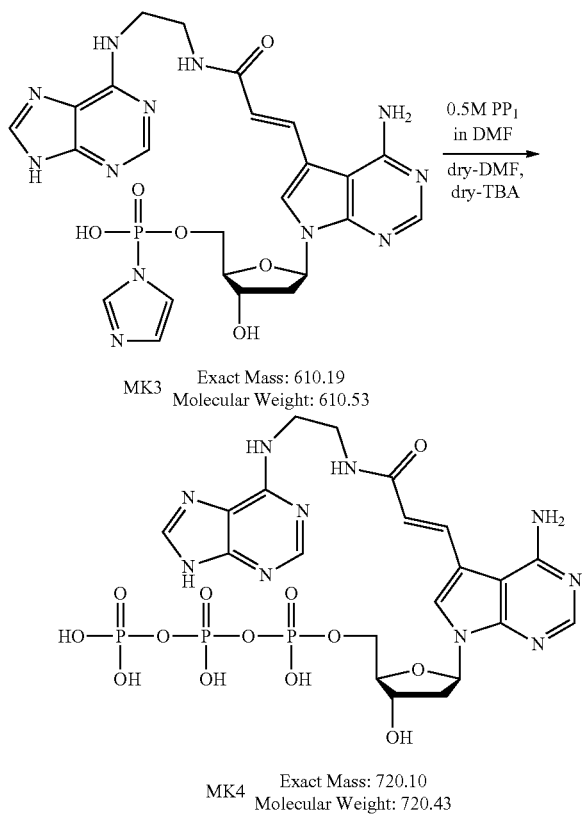

MK3 (30.03 µmol) was dried in vacuo, the atmosphere was replaced with Ar, and then, azeotropy between the MK3 and dry-Pyridine (5 mL) was caused twice, and the azeotrope was then suspended in dry-DMF (1 mL). Further, dry-n-Tributylamine (30 µL, 1.25×10$^4$ mol, 4 eq.) and 0.5 mol/L n-Tributylamine pyrophosphate in DMF (310 µL, 1.53×10$^4$ mol, 5 eq.) were added to the suspension and then stirred at room temperature. After 6.5 hours from the initiation of the stirring, a 1 mol/L TEAB buffer (5 mL) was added and stirred for 30 minutes, and then the solvent was distilled off under reduced pressure. Water was added, an aqueous layer was separated with Ether twice, purified by anion-exchange column chromatography, and freeze-dried, to give MK4. Physical properties of MK4 are shown below.
Yield: 3.33 µmol, Yield: 11.1%
ESI-MS (negative ion mode) m/z, found=719.0, calculated for [(M−H)−]=719.1

Example 2

The present example examined whether binding nucleic acid molecules that bind to sIgA and binding nucleic acid molecules that bind to α-amylase can be obtained using MK4.

(1) Binding Nucleic Acid Molecule

Binding nucleic acid molecules that bind to a target were obtained by the SELEX method, except that candidate polynucleotides prepared by using, in addition to deoxyribonucleotides containing thymine, guanine, and cytosine, respectively (dTTP, and dGTP, and dCTP, respectively), MK4 as deoxyribonucleotide were used. Specifically, the binding nucleic acid molecules were obtained in the following manner. sIgA (manufactured by MP Biomedicals, LLC-Cappel Products) or human salivary amylase (manufactured by Lee BioSolutions, Inc.) as the target was bound to beads (Dynabeads MyOne Carboxylic Acid, manufactured by Invitrogen) according to the protocols attached to the products. After binding the target, the beads were washed with a selection buffer (SB Buffer: 40 mmol/L HEPES, 125 mmol/L NaCl, 5 mmol/L KCl, 1 mmol/L MgCl$_2$, 0.01% Tween® 20, pH 7.5), whereby target beads were prepared. dsDNAs with MK4 inserted therein were prepared using complementary strands with their 5' ends modified with biotin (forward (Fw) primer region-N30 (30 bases)-reverse (Rv) primer region), forward primers and DNA polymerase (KOD Dash, manufactured by Toyobo Co., Ltd.), and dTTP, dGTP, dCTP and MK4. Subsequently, the dsDNAs were bound to the beads (Dynabeads MyOne Carboxylic Acid), and then, ss (single strand) DNAs were eluted with a 0.02 mol/L NaOH aqueous solution. Furthermore, the NaOH aqueous solution was neutralized with a 0.08 mol/L hydrochloric acid aqueous solution. Thus, an ssDNA library was prepared. 20 pmol of the library was mixed with 250 µg of the target beads at 25° C. for 15 minutes. Thereafter, the beads were washed with the SB buffer. Then, the ssDNAs bound to the beads were eluted with a 7 mol/L urea aqueous solution. The eluted ssDNAs were amplified by PCR using the forward primers and the biotin-modified reverse primers. In the PCR, dTTP, adenine-containing deoxyribonucleotide (dATP), dGTP, and dCTP were used as deoxyribonucleotides. The obtained dsDNAs were bound to magnetic beads (Dynabeads MyOne SA C1 magnetic beads, manufactured by Invitrogen). Thereafter, forward strands were eluted with a 0.02 mol/L NaOH aqueous solution and removed. After removing the forward strands, the magnetic beads were washed with the SB buffer. Using the magnetic beads with the complementary strands immobilized thereon, forward primers and DNA polymerase (KOD Dash, manufactured by Toyobo Co., Ltd.), dTTP, dGTP, dCTP, and MK4, dsDNAs with MK4 inserted therein were prepared in the above-described manner. Next, an ssDNA library was prepared by eluting forward strands with a 0.02 mol/L NaOH aqueous solution, and this library was used in a subsequent round. Nucleic acid molecules that bind to sIgA or α-amylase were selected by performing eight rounds of the same process. Thereafter, PCR was performed using forward primers and reverse primers without biotin modification. The obtained nucleic acid molecules were subjected to sequencing using a sequencer (GS junior sequencer, manufactured by Roche).

As a result, a binding nucleic acid molecule consisting of the base sequence of SEQ ID NO: 1 below was obtained as the binding nucleic acid molecule that binds to α-amylase, and a binding nucleic acid molecule consisting of the base sequence of SEQ ID NO: 2 below was obtained as the binding nucleic acid molecule that binds to sIgA. In the base sequences of SEQ ID NOs: 1 and 2, the underlined bases A are MK4.

α-amylase-binding nucleic acid molecule 1
(SEQ ID NO: 1)
5'-GGTTTGGACGCAATCTCCCTAATCTAGTGACGAAAATGTACGAG
GGGGTCATTTGAAACTACAATGGGCGGGCTTATC-3' sIgA-binding nucleic acid molecule
(SEQ ID NO: 2)
5'-GGTTTGGACGCAATCTCCCTAATCAAGCCACGGAGAGTCCGAGG
TGACCATTAAGCAGGAAACTACAATGGGCGGGCTTA-3'

(2) Examination of Binding by Surface Plasmon Resonance (SPR)

The binding between the α-amylase-binding nucleic acid molecule 1 and α-amylase and the binding between the sIgA-binding nucleic acid molecule and sIgA were measured under the following SPR conditions. The α-amylase-binding nucleic acid molecule 1 and sIgA-binding nucleic acid molecule adapted so that a 20-mer poly(dT) was added to the 3' ends were each used as the following ligand 2. Further, as control 1 and control 2, examination of the binding was performed in the same manner except that, in control 1, bovine serum albumin (BSA) was used as the following analyte, and in control 2, chromogranin A (CgA, manufactured by Creative BioMart) was used as the following analyte in a system for examining the binding of the α-amylase-binding nucleic acid molecules 1 and the α-amylase was used as the following analyte in a system for examining the binding of the sIgA-binding nucleic acid molecules.

(SPR Measurement Conditions)
Measurement device: ProteOn™ XPR36 (manufactured by BioRad)
Measurement chip: ProteOn™ NLC Sensor Chip (manufactured by BioRad)
Ligand 1: poly(dA) (20-mer) with the 5' end thereof being modified with biotin: 5 μmol/L
Buffer: 40 mmol/L HEPES, 125 mmol/L NaCl, 1 mmol/L MgCl$_2$, 5 mmol/L KCl, 0.01%
Tween® 20, pH 7.4
Ligand 2: buffer containing a binding nucleic acid molecule with poly(T) (20-mer) added to the 3' end at 200 nmol/L
Ligand flow rate: 25 μL/min, 80 sec
Analyte: buffer containing a target at 400 nmol/L
Analyte flow rate: 50 μL/min
Contact Time: 120 sec
Dissociation: 300 sec
  sIgA: IgA (Secretory), Human (manufactured by MP Biomedicals, LLC-Cappel Products, Catalogue number: #55905)
  Amylase: α-amylase (manufactured by Lee Biosolutions, Catalogue number: #120-10)
  CgA: recombinant full length Human Chromogranin A (manufactured by Creative BioMart, Catalog number: # CHGA 26904TH)
  BSA: Bovine Serum Albumin (manufactured by SIGMA, Catalogue number: # A7906)

Figure 2:
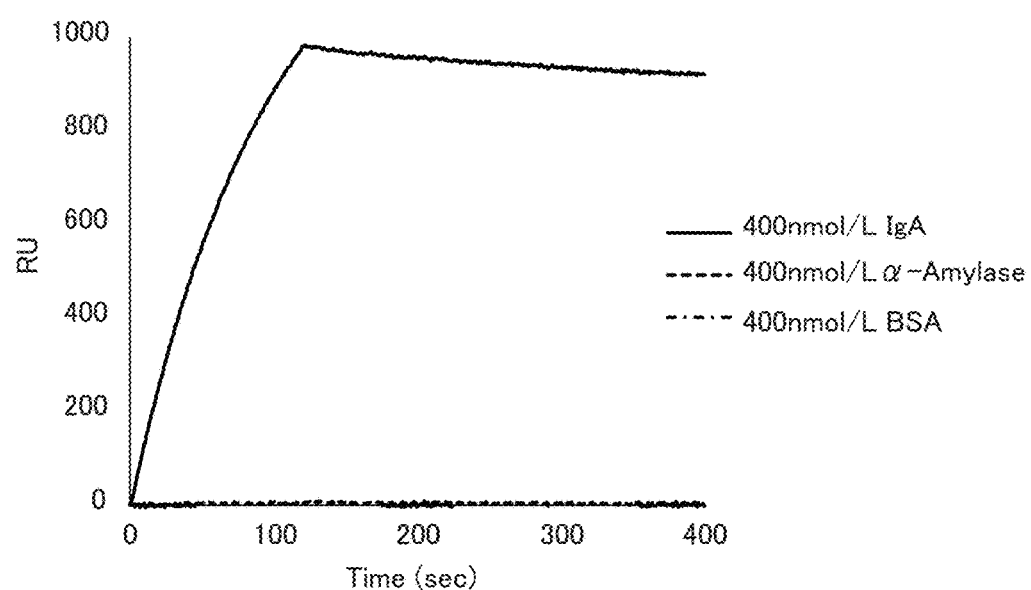
FIG. 2 is a graph showing the binding ability of the secretory immunoglobulin A (sIgA)-binding nucleic acid molecule to sIgA in Example 2.

The results of measuring the binding between the α-amylase-binding nucleic acid molecule 1 and the α-amylase are shown in FIG. 1, and the results of measuring the binding between the sIgA-binding nucleic acid molecule and sIgA are shown in FIG. 2. FIG. 1 is a graph showing the binding ability of the α-amylase-binding nucleic acid molecule 1 to the α-amylase. In FIG. 1, the horizontal axis indicates the time elapsed after the injection of the ligand, and the vertical axis indicates the relative value (RU) of the binding force. As can be seen in FIG. 1, the α-amylase-binding nucleic acid molecule 1 bound to the α-amylase, whereas they did not bind to CgA or BSA.

Next, FIG. 2 is a graph showing the binding ability of the sIgA-binding nucleic acid molecule to sIgA. In FIG. 2, the horizontal axis indicates the time elapsed after the injection of the ligand, and the vertical axis indicates the relative value (RU) of the binding force. As can be seen in FIG. 2, the sIgA-binding nucleic acid molecules bind sIgA, whereas they do not bind to the α-amylase or BSA.

From these results, it was found that a binding nucleic acid molecule that binds to α-amylase and a binding nucleic acid molecule that binds to sIgA can be obtained using MK4, which is the nucleoside derivative of the present invention.

(3) Examination of Binding Force

The relative value (RU) of the binding force was measured in the same manner as in the above item (2), except that the α-amylase-binding nucleic acid molecule 1 having a 20-mer poly(T) added to its 3' end was used as the ligand 2 and that the concentration of the α-amylase as the analyte was set to 5, 10, 20, 40, or 80 nmol/L. Also, the relative value (RU) of the binding force was measured in the same manner as in the above item (2), except that the sIgA-binding nucleic acid molecule having a 20-mer poly(T) added to its 3' end was used as the ligand 2 and that the concentration of sIgA as the analyte was 12.5, 25, 50, 100, or 200 nmol/L. Then, based on the relative values (RU) of the binding force measured in the above, the dissociation constant between the α-amylase-binding nucleic acid molecule 1 and the α-amylase and the dissociation constant between the sIgA-binding nucleic acid molecule and sIgA were calculated. As a result, the dissociation constant between the α-amylase-binding nucleic acid molecules 1 and the α-amylase was 8.14 nM, and the dissociation constant between the sIgA-binding nucleic acid molecules and sIgA was 7.63 nM. These results demonstrate that both the binding nucleic acid molecules have excellent binding ability to the targets.

(4) Examination of Binding by Capillary Electrophoresis

Binding between the α-amylase-binding nucleic acid molecule 1 and α-amylase was measured by capillary electrophoresis performed under the following conditions. The α-amylase-binding nucleic acid molecule adapted so that the 5' end thereof was labeled with a 20-mer TYE™ 665 was used as the following clone. As a control, the measurement was performed in the same manner except that α-amylase was not added as the target.

Figure 3:
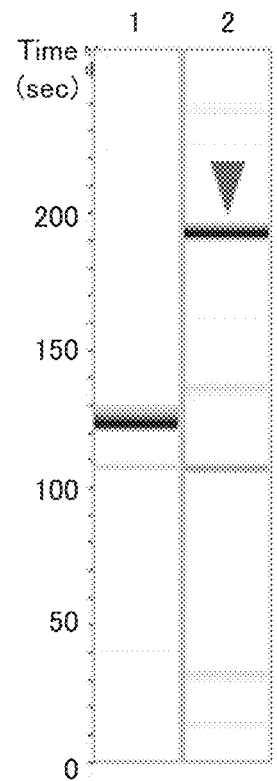
FIG. 3 is a photograph showing the results of capillary electrophoresis in Example 2.

(Conditions of Capillary Electrophoresis)
Measurement device: Cosmo-i SV1210 (Hitachi High-Technologies Corporation)
Measurement chip: i-chip 12 (Hitachi Chemical Company, Ltd.)
Electrophoresis gel: 0.6% (Hydroxypropyl)methyl cellulose, viscosity 2. 600-5, 600 (manufactured by SIGMA, Catalogue number: # H7509)
Gel dissolving buffer: 40 mmol/L HEPES (pH 7.5), 5 mmol/L KCl, 1 mmol/L MgCl$_2$
Clone: solution containing 200 nmol/L amylase-binding nucleic acid molecule with its 5' end labeled with TYE™ 665, 40 mmol/L HEPES (pH 7.5), 125 mmol/L NaCl, 5 mmol/L KCl, and 1 mmol/L MgCl$_2$
Target: solution containing 4 μmol/L amylase (α-Amylase-High Purity, Human, manufactured by Lee BioSolutions, Inc., Catalogue number: #120-10), 40 mmol/L HEPES (pH 7.5), 125 mmol/L
NaCl, 5 mmol/L KCl, and 1 mmol/L MgCl$_2$
Folding: 95° C., after 5 min, on ice 5 min
Mixing: after addition of target, room temperature (around 25° C.), 30 min, 1000 rpm Injection voltage: 600 V
Injection time: 120 sec
Separation voltage: 350 V
Separation Time: 260 sec The results obtained are shown in FIG. 3. FIG. 3 is a photograph showing the results of capillary electrophoresis. In FIG. 3, the electrophoresis time is shown on the left side of the photograph, and the respective lanes show, from the left, the result obtained regarding the control (without α-amylase) and the result obtained when the α-amylase was used. As can be seen in FIG. 3, the electrophoresis time in the presence of the α-amylase was longer than that in the control without α-amylase. From these results, it was found that the α-amylase-binding nucleic acid molecule 1 binds to α-amylase.

(5) Examination of Binding by Pull-Down Assay

Beads 1 carrying α-amylase-binding nucleic acid molecule bound thereto (hereinafter, also referred to as "bound beads A1") were prepared by bringing an α-amylase-binding nucleic acid molecule 1 with its 5' end modified with biotin into contact with streptavidin-modified beads (Dynabeads MyOne SA C1 magnetic beads, manufactured by Invitrogen). Next, the bound beads A1 were mixed with a saliva-containing SB buffer (saliva sample), and the resultant mixture was shaken at 1000 rpm for 60 minutes at room temperature (around 25° C.).

After the shaking, the bound beads A1 were washed three times with the SB buffer. Then, the bound beads A1 were treated at 95° C. for 10 minutes in the presence of the SDS buffer, whereby the α-amylase bound to the bound beads A1 was eluted. The composition of the SDS buffer was as follows: 62.5 mmol/L Tris, 2% SDS, 5% sucrose, 0.002% Bromophenol blue, and 1% 2-mercaptoethanol.

The thus-obtained eluate was loaded onto a gel (PAGEL C50L, manufactured by ATTO), and electrophoresis was performed in the presence of an electrophoresis buffer. The composition of the electrophoresis buffer was as follows: 25 mmol/L Tris, 192 mmol/L glycine, and 0.1% SDS. Next, the gel after the electrophoresis was stained with a staining agent (Gel Code, manufactured by Thermo SCIENTIFIC, Catalogue number: #24594), and imaged with ChemiDoc (manufactured by BioRad). Further, as control 1 and control 2, imaging was performed in the same manner except that, in control 1, nucleic acid molecules that do not bind to α-amylase with their 5' ends modified with biotin were used (control nucleic acid molecules 1) and, in control 2, only α-amylase was used.

```
Control nucleic acid molecule 1
                                         (SEQ ID NO: 3)
5'-GGATACCTTAACGCCGCCTATTG-3'
```

Figure 4:
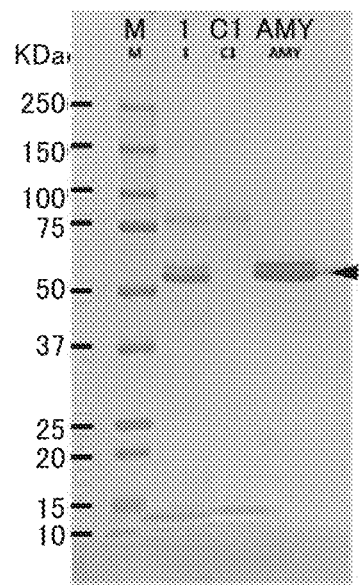
FIG. 4 is a photograph showing the results of the pull-down assay in Example 2.

The results obtained are shown in FIG. 4. FIG. 4 is a photograph showing the results of the pull-down assay. In FIG. 4, the numerical values on the left side of the photograph indicate molecular weights, and the respective lanes show, from the left, the results obtained regarding the molecular weight marker (M), the saliva sample (1), control 1 (C1), and control 2 (AMY). As can be seen in FIG. 4, in the lane showing the result of control 1, no band was observed at the same position (about 50 kDa) as in the lane showing the result of control 2, whereas, in the lane showing the result regarding the saliva sample, a band was observed at the same electrophoretic mobility position as in the lane showing the result of control 2. In other words, the binding of the α-amylase-binding nucleic acid molecules 1 to α-amylase was observed. From these results, it was found that the α-amylase-binding nucleic acid molecule 1 binds to α-amylase.

Example 3

The present example examined whether a binding nucleic acid molecule that binds to human β-defensin 4A and a binding nucleic acid molecule that binds to human lysozyme can be obtained using MK4.

(1) Binding Nucleic Acid Molecule

The binding nucleic acid molecule that binds to human β-defensin 4A and the binding nucleic acid molecule that binds to human lysozyme were obtained in the same manner as in the above item (1) in Example 2, except that, instead of sIgA as the target, human β-defensin 4A (manufactured by Novoprotein Scientific Inc., Catalog number: # C127) or human lysozyme (manufactured by Novoprotein Scientific Inc., Catalog number: # P61626) was used.

As a result, as the binding nucleic acid molecule that binds to β-defensin (BDN)4A, the binding nucleic acid molecules consisting of the base sequences of SEQ ID NOs: 4 to 6 shown below were obtained, and as the binding nucleic acid molecule that binds to lysozyme, binding nucleic acid molecules consisting of the base sequences of SEQ ID NOs: 7 to 9 shown below were obtained. In the base sequences of SEQ ID NOs: 4 to 9 below, each underlined A is MK4.

```
BDN4A-binding nucleic acid molecule 1
                                         (SEQ ID NO: 4)
5'-GGTTACACGAGCCGCACATTTCTATTTTTACGGGGTATAGTTCT
CTGAGGAGGAGTTCCCAGGCGAAGTTGTTATC-3'

BDN4A-binding nucleic acid molecule 2
                                         (SEQ ID NO: 5)
5'-CGAGCCGCACATTTCTATTTTTACGGGGTATAGTTCTCTGAGGA
GGAGTTCCCAGGCGAAGTTGTTATC-3'

BDN4A-binding nucleic acid molecule 3
                                         (SEQ ID NO: 6)
5'-GGTTACACGAGCCGCACATTTCACCGTGATAGTTCTCTGAGGAG
GACTTCTAGAGTTCCCAGGCGAAGTTGTTATC-3'

Lysozyme-binding nucleic acid molecule 1
                                         (SEQ ID NO: 7)
5'-GGTTACACGAGCCGCACATTTCTAACGGGAACTTCAACCCATAC
AGTCTTTTGAGTTCCCAGGCGAAGTTGTTATC-3'

Lysozyme-binding nucleic acid molecule 2
                                         (SEQ ID NO: 8)
5'-CGAGCCGCACATTTCTAACGGGAACTTCAACCCATACAGTCTTT
TGAGTTCCC-3'

Lysozyme-binding nucleic acid molecule 3
                                         (SEQ ID NO: 9)
5'-GGTTACACGAGCCGCACATTTCTTTACTCCGGAACCCATACAGT
CTTTTCCGGAGTTCCCAGGCGAAGTTGTTATC-3'
```

(2) Examination of Binding by SPR

The binding between each type of the BDN4A-binding nucleic acid molecules and BDN4A and the binding between each type of the lysozyme-binding nucleic acid molecules and lysozyme were measured in the same manner as in the above item (2) in Example 2, except that the BDN4A-binding nucleic acid molecules or lysozyme-binding nucleic acid molecules having a 20-mer poly(dT) added to their 3' ends were used as the ligand 2 and each of the following proteins was used as the analyte. As controls, the binding was examined in the same manner except that α-amylase and sIgA were used as the analytes.

β-defensin 4A: β-Defensin 4A, Human (manufactured by Novoprotein Scientific Inc., Catalog number: # C127)

Human lysozyme: Recombinant Human Lysozyme C (manufactured by Novoprotein Scientific Inc., Catalog number: # P61626)

Figure 5A:
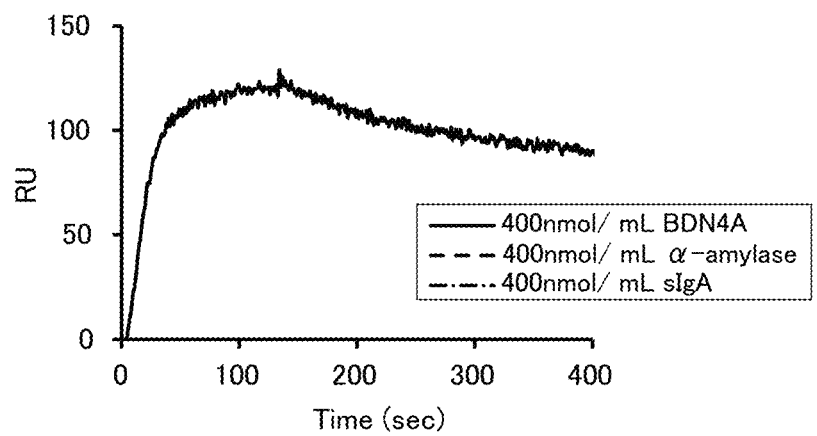
FIGS. 5A to 5C are graphs showing the binding ability of the respective types of β-defensin (BDN)4A-binding nucleic acid molecules to BDN4A in Example 3.
Figure 5B:
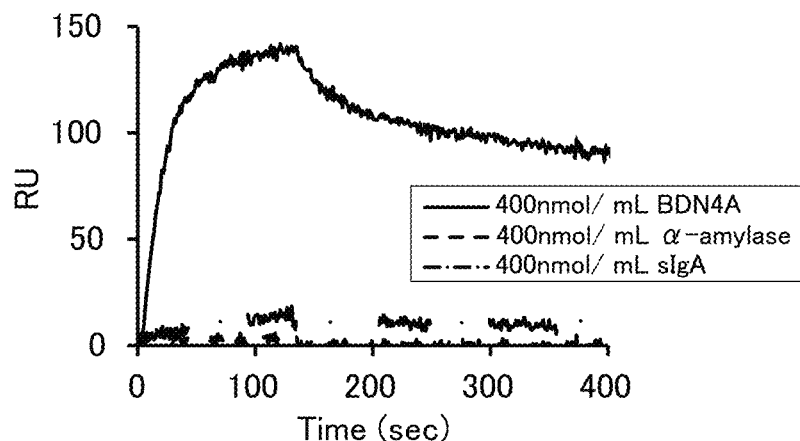
Figure 5C:
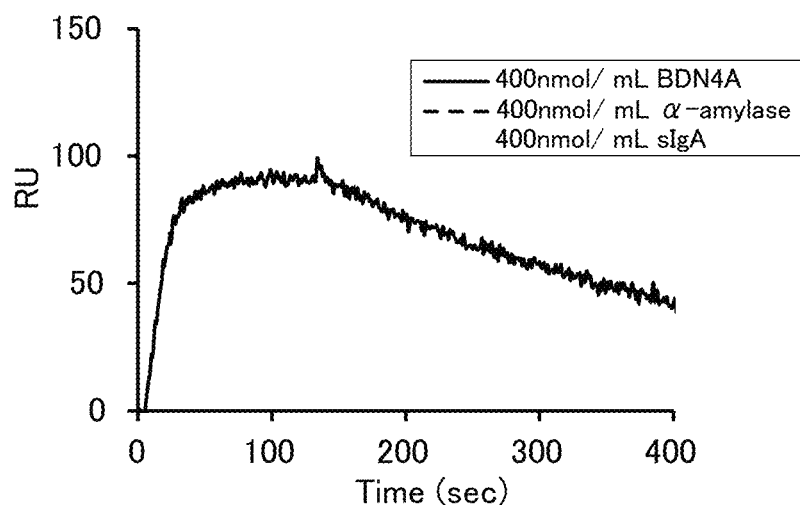

The results of measuring the binding between the respective types of the BDN4A-binding nucleic acid molecules and BDN4A are shown in FIGS. 5A to 5C. The results of measuring the binding between the respective types of the lysozyme-binding nucleic acid molecules and the lysozyme are shown in FIGS. 6A to 6C.

FIGS. 5A to 5C are graphs showing the binding ability of the respective types of the BDN4A-binding nucleic acid molecules to BDN4A. FIGS. 5A to 5C show the results obtained regarding the BDN4A-binding nucleic acid molecules 1 to 3, respectively. In each of FIGS. 5A to 5C, the horizontal axis indicates the time elapsed after the injection of the ligand, and the vertical axis indicates the relative value of the binding force (RU). As can be seen in FIGS. 5A to 5C, the respective types of the BDN4A-binding nucleic acid molecules did not bind to the amylase or sIgA and bound to BDN4A.

Figure 6A:
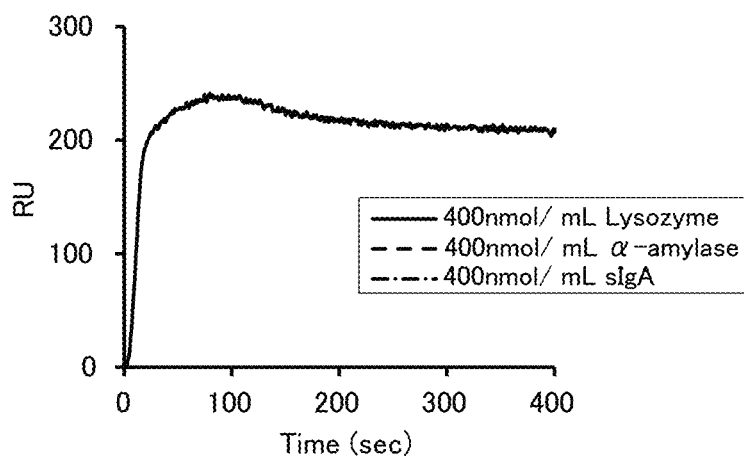
FIGS. 6A to 6C are graphs showing the binding ability of the respective types of lysozyme-binding nucleic acid molecules to lysozyme in Example 3.
Figure 6B:
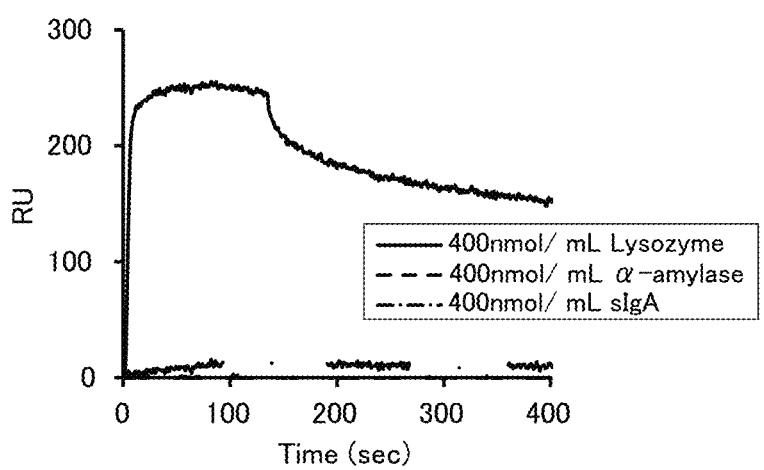
Figure 6C:
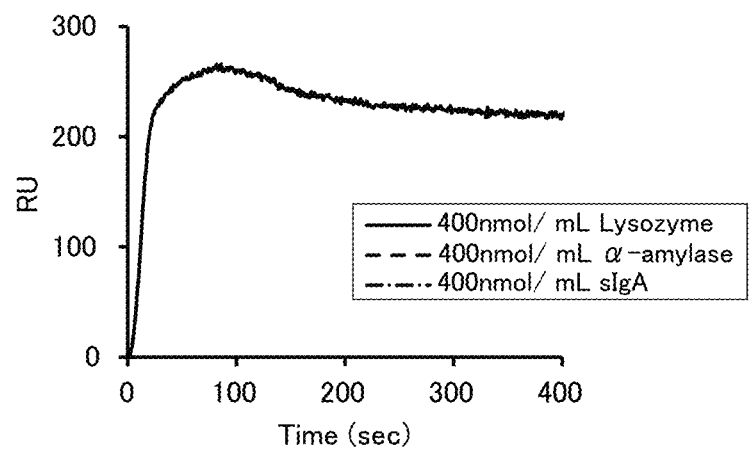

Next, FIGS. 6A to 6C are graphs showing the binding ability of the respective types of the lysozyme-binding nucleic acid molecules to the lysozyme. FIGS. 6A to 6C show the results obtained regarding the lysozyme-binding nucleic acid molecules 1 to 3, respectively. In each of FIGS. 6A to 6C, the horizontal axis indicates the time elapsed after the injection of the ligand, and the vertical axis indicates the relative value (RU) of the binding force. As can be seen in FIGS. 6A to 6C, the lysozyme-binding nucleic acid molecules did not bind to the amylase or sIgA and bound to the lysozyme.

From these results, it was found that a binding nucleic acid molecule that binds to BDN4A and a binding nucleic acid molecule that binds to lysozyme can be obtained using MK4, which is the nucleoside derivative of the present invention.

(3) Examination of Binding Force

The relative value (RU) of the binding force was measured in the same manner as in the above item (2) in Example 3, except that the BDN4A-binding nucleic acid molecules having a 20-mer poly(T) added to their 3' ends were used as the ligand 2 and that the concentration of BDN4A as the analyte was set to 25, 50, 100, 200, or 400 nmol/L. Also, the relative value (RU) of the binding force was measured in the same manner as in the item (2) in Example 3, except that each type of the lysozyme-binding nucleic acid molecules having a 20-mer poly(T) added to their 3' ends were used as the ligand 2 and that the concentration of the lysozyme as the analyte was set to 12.5, 25, 50, 100, or 200 nmol/L. Then, on the basis of the relative values (RU) of the binding force measured in the above, the dissociation constant between each type of the BDN4A-binding nucleic acid molecules and BDN4A and the dissociation constant between each type of the lysozyme-binding nucleic acid molecules and the lysozyme were calculated. The results obtained are shown in Table 1 below.

TABLE 1

| Nucleic acid molecule name | Dissociation constant (nM) |
| --- | --- |
| BDN4A-binding nucleic acid molecule 1 | 6.52 |
| BDN4A-binding nucleic acid molecule 2 | 8.07 |
| BDN4A-binding nucleic acid molecule 3 | 48.2 |

TABLE 1-continued

| Nucleic acid molecule name | Dissociation constant (nM) |
| --- | --- |
| Lysozyme-binding nucleic acid molecule 1 | 1.18 |
| Lysozyme-binding nucleic acid molecule 2 | 1.03 |
| Lysozyme-binding nucleic acid molecule 3 | 1.83 |

As can be seen in Table 1 above, it was found that these binding nucleic acid molecules all have excellent binding ability to the targets.

(4) Examination of Binding by Pull-Down Assay

Beads carrying BDN4A-binding nucleic acid molecules bound thereto (also referred to as "bound beads C" hereinafter) and beads carrying lysozyme-binding nucleic acid molecules bound thereto (also referred to as "bound beads D" hereinafter) were prepared by bringing BDN 4A-binding nucleic acid molecules 1 and lysozyme-binding nucleic acid molecules 1 with their 5' ends modified with biotin into contact with the above-described streptavidin-modified beads, respectively. Next, SDS-PAGE was performed, and gel was imaged in the same manner as in the item (5) in Example 2, except that the bound beads C and D were each mixed with a SB buffer containing 90 (v/v) % saliva (saliva sample) or a SB buffer containing BDN4A or lysozyme (target sample). Further, as control 1 and control 2, imaging was performed in the same manner except that, in control 1, the following control nucleic acid molecules 2 with their 5' ends modified with biotin were used and, in control 2, only BDN4A or only lysozyme was used.

```
Control nucleic acid molecule 2
                             (SEQ ID NO: 10)
     5'-GGTAACCGCCCTGTCTTGATAAC-3'
```

Figure 7:
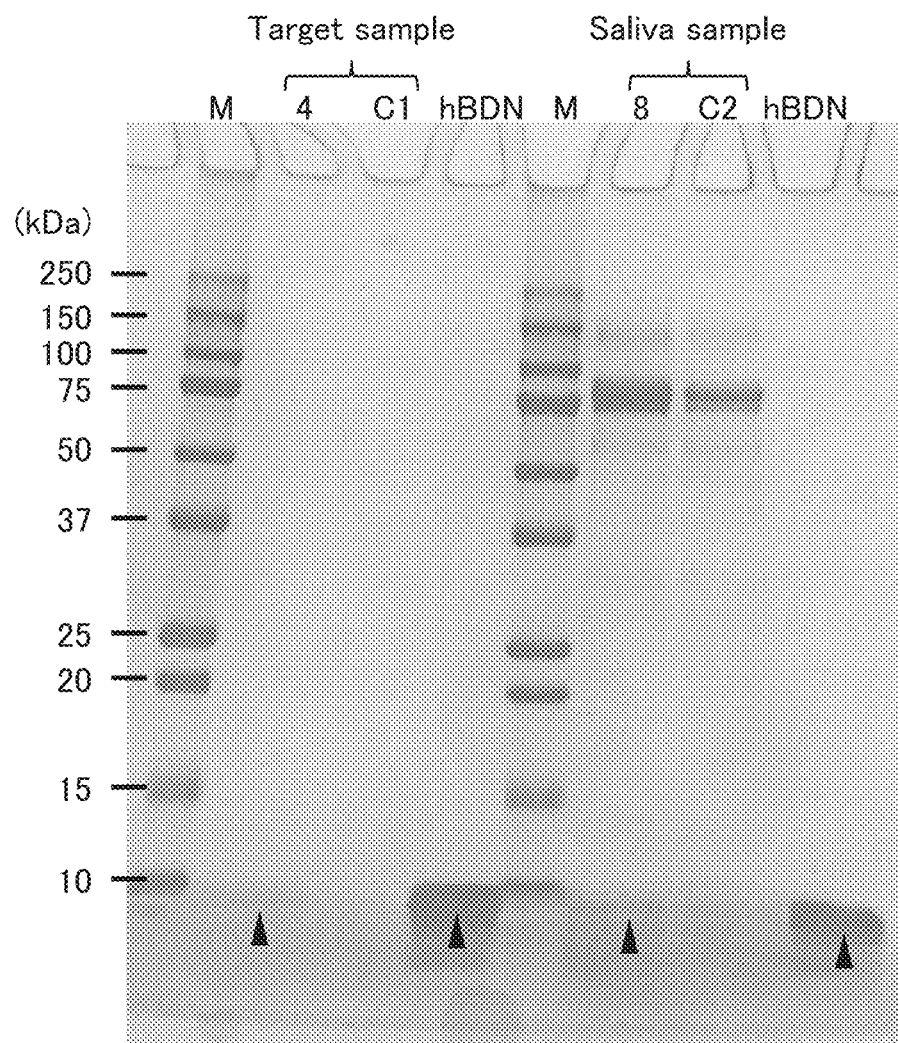
FIG. 7 is a photograph showing the results of the pull-down assay in Example 3.

Next, the results obtained when the bound beads C were used are shown in FIG. 7. FIG. 7 is a photograph showing the results of the pull-down assay using the bound beads C. In FIG. 7, the numerical values on the left side of the photograph indicate molecular weights, and the respective lanes are, from the left, lane M (marker), lane 4 (target sample), lane C1 (control 1), lane hBDN (control 2), lane M (marker), lane 8 (saliva sample), lane C2 (control 1), and lane hBDN (control 2). As can be seen in FIG. 7, in the lane showing the result of control 1, no band was observed at the same position (about 10 kDa) as in the lane showing the result of control 2, whereas, in the lanes showing the results obtained when the target sample and the saliva sample were used, bands were observed at the same electrophoretic mobility position as in the lane showing the result of control 2, as indicated with the arrows in FIG. 7. In other words, binding of the BDN4A-binding nucleic acid molecules 1 to BDN4A was observed. From these results, it was found that the BDN4A-binding nucleic acid molecules bind to BDN4A.

Figure 8A:
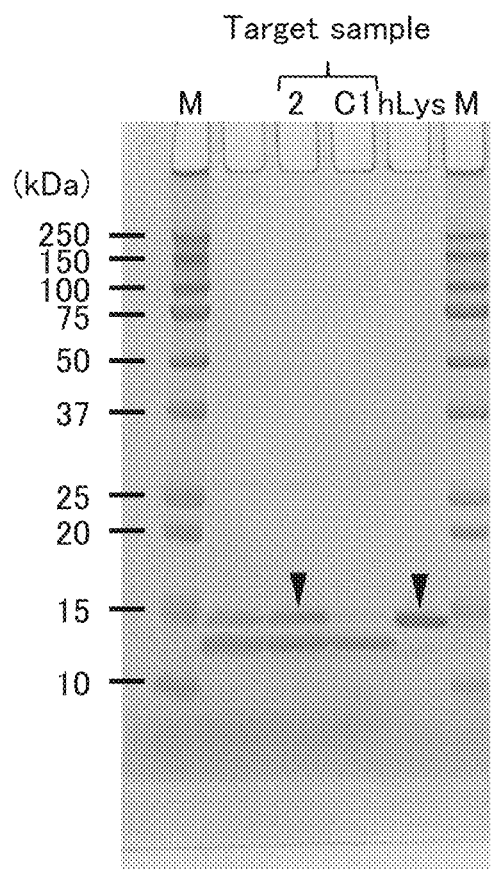
FIGS. 8A and 8B are photographs showing the results of the pull-down assay in Example 3.
Figure 8B:
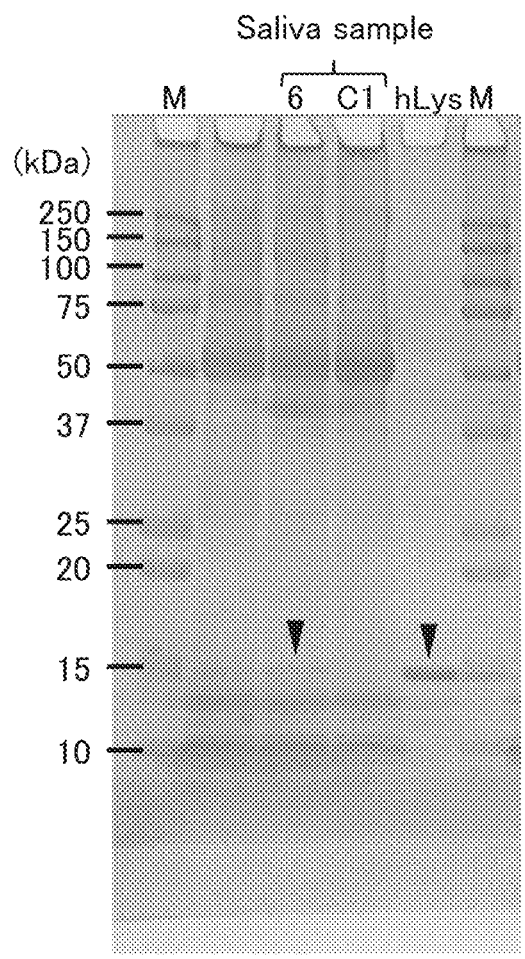
Figure 9A:
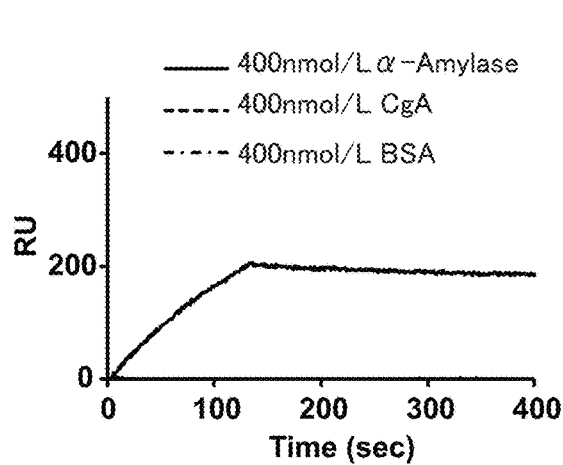
FIGS. 9A and 9F are graphs showing the binding ability of the respective types of α-amylase-binding nucleic acid molecules to α-amylase in Example 4.
Figure 9B:
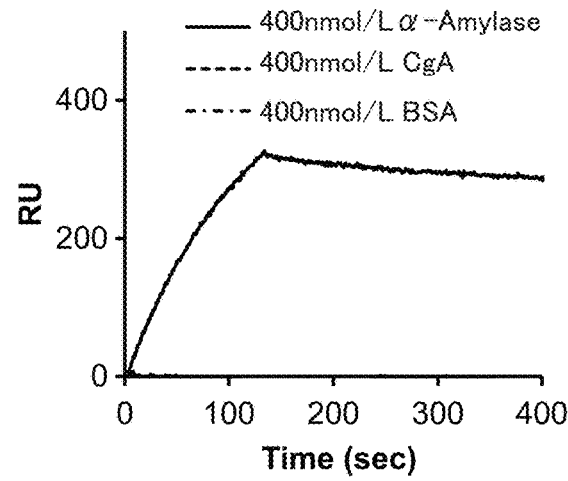
Figure 9C:
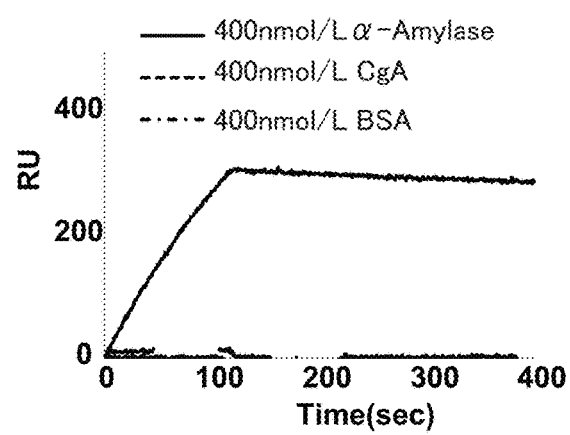
Figure 9D:
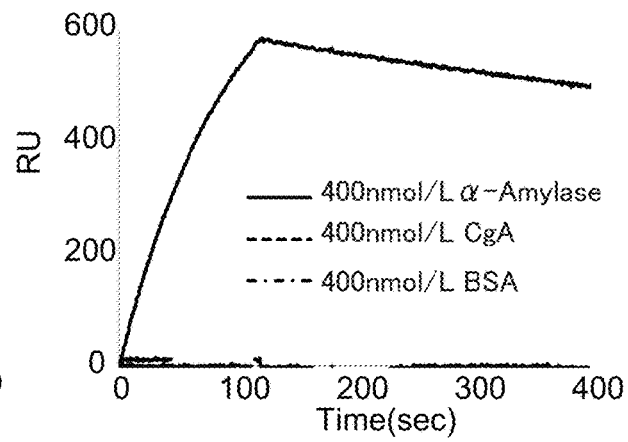
Figure 9E:
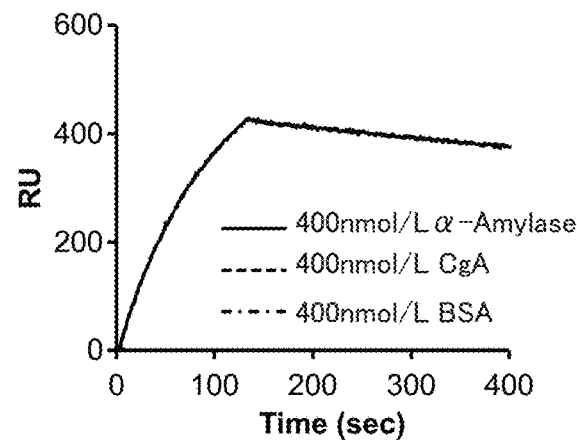
Figure 9F:
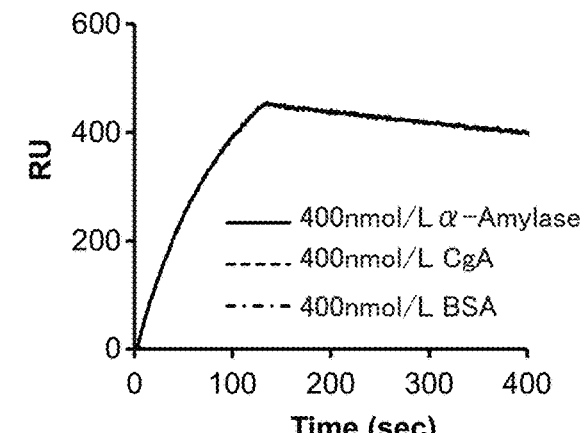

Next, the results obtained when the bound beads D were used are shown in FIGS. 8A and 8B. FIGS. 8A and 8B are photographs showing the results of the pull-down assay. FIG. 8A shows the result obtained when the target sample was used and FIG. 8B shows the result obtained when the saliva sample was used. In FIG. 8A, the numerical values on the left side of the photograph indicate molecular weights, and the respective lanes are, from the left, lane M (marker), lane 2 (target sample), lane C1 (control 1), lane hLys (control 2), and lane M (marker). In FIG. 8B, the respective lanes are, from the left, lane M (marker), lane 6 (saliva sample), lane C1 (control 1), lane hLys (control 2), and lane M (marker). As can be seen in FIG. 8, in the lane showing the result of control 1, no band was observed at the same position (about 15 kDa) as in the lane showing the result of control 2, whereas, in the lanes showing the results obtained when the target sample and the saliva sample were used, bands were observed at the same electrophoretic mobility position as in the lane showing the result of control 2, as indicated with the arrows in FIG. 8. In other words, binding of the lysozyme-binding nucleic acid molecules 1 to the lysozyme was observed. From these results, it was found that the lysozyme-binding nucleic acid molecules bind to lysozyme.

Example 4

The present example examined whether binding nucleic acid molecules that bind to human α-amylase can be obtained using MK4.

(1) Binding Nucleic Acid Molecule

Binding nucleic acid molecules that bind to human α-amylase were obtained in the same manner as in the item (1) in Example 2, except that, instead of sIgA as the target, the above-described human α-amylase was used.

As a result, as the binding nucleic acid molecules that bind to α-amylase, binding nucleic acid molecules consisting of the base sequences of SEQ ID NOs: 11 to 16 shown below were obtained. In the base sequences of SEQ ID NOs: 11 to 16 below, each underlined A is MK4.

```
α-amylase-binding nucleic acid molecule 2
                                   (SEQ ID NO: 11)
5'-GGTTTGGACGCAATCTCCCTAATCTAGTGACGAAAATGTACGAG
GGGGTCATTTGAAACTA-3'

α-amylase-binding nucleic acid molecule 3
                                   (SEQ ID NO: 12)
5'-GCAATCTCCCTAATCTAGTGACGAAAATGTACGAGGGGGTCATT
TGAAACTA-3'

α-amylase-binding nucleic acid molecule 4
                                   (SEQ ID NO: 13)
5'-GGTTTGGACGCAATCTCCCTAATCAGACTATTATTTCAAGTACG
TGGGGGTCTTGAAACTACAATGGGCGGGCTTATC-3'

α-amylase-binding nucleic acid molecule 5
                                   (SEQ ID NO: 14)
5'-GGTTTGGACGCAATCTCCCTAATCTAAAGTTTCTAAACGATGTG
GCGGCATTCAGAAACTACAATGGGCGGGCTTATC-3'

α-amylase-binding nucleic acid molecule 6
                                   (SEQ ID NO: 15)
5'-GGTTTGGACGCAATCTCCCTAATCTAAAGTTTCTAAACGATGTG
GCGGCATTCAGAAACT-3'

α-amylase-binding nucleic acid molecule 7
                                   (SEQ ID NO: 16)
5'-GCAATCTCCCTAATCTAAAGTTTCTAAACGATGTGGCGGCATTC
AGAAACT-3'
```

(2) Examination of Binding by SPR

The binding between each type of the α-amylase-binding nucleic acid molecules and the α-amylase was measured in the same manner as for measuring the binding of the α-amylase-binding nucleic acid molecules 1 in the above item (2) in Example 2. As controls, the binding was examined in the same manner except that CgA and BSA were used as the analytes. The results obtained are shown in FIGS. 9A to 9F.

FIGS. 9A to 9F are graphs showing the binding ability of the respective types of the α-amylase-binding nucleic acid molecules to the α-amylase. In FIGS. 9A to 9F show the results obtained regarding the α-amylase-binding nucleic acid molecules 2 to 7, respectively. In each of FIGS. 9A to 9F, the horizontal axis indicates the time elapsed after the injection of the ligand, and the vertical axis indicates the relative value (RU) of the binding force. As can be seen in FIGS. 9A to 9F, the respective types of the α-amylase-binding nucleic acid molecules did not bind to CgA or BSA and bound to the α-amylase.

(3) Examination of Binding Force

The relative value (RU) of the binding force was measured in the same manner as in the item (2) in Example 4, except that each type of the α-amylase-binding nucleic acid molecules having a 20-mer poly(T) added to their 3' ends were used as the ligand 2, and the concentration of the α-amylase as the analyte was set to 5, 10, 20, 40, or 80 nmol/L. Then, on the basis of the relative values (RU) of the binding force measured in the above, the dissociation constant between each type of the α-amylase-binding nucleic acid molecules and the α-amylase was calculated. As a result, the dissociation constants between the α-amylase-binding nucleic acid molecules 2 to 7 and the α-amylase were 6.91, 7.75, 5.18, 13.2, 11.5, and 11.1 nM, respectively. These results demonstrate that all of the binding nucleic acid molecules have excellent binding ability to the targets.

(4) Examination of Binding by Capillary Electrophoresis

The binding was measured in the same manner as in the item (4) in Example 2, except that, in addition to the α-amylase-binding nucleic acid molecules 1, the α-amylase-binding nucleic acid molecules 5 were used. As a control, the measurement was performed in the same manner, except that the α-amylase was not added as the target.

Figure 10:
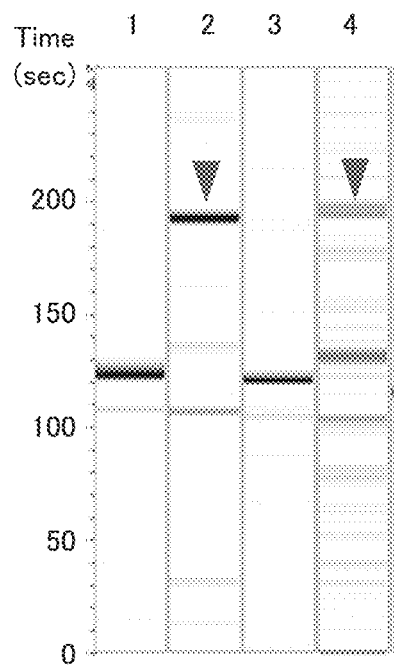
FIG. 10 is a photograph showing the results of capillary electrophoresis in Example 4.

The results obtained are shown in FIG. 10. FIG. 10 is a photograph showing the results of capillary electrophoresis. In FIG. 10, the electrophoresis time is shown on the left side of the photograph, and the respective lanes show, from the left, the results obtained regarding the α-amylase-binding nucleic acid molecules 1 in the control (without α-amylase) and in the presence of the α-amylase, and the results obtained regarding the α-amylase-binding nucleic acid molecules 5 in the control (without α-amylase) and in the presence of the α-amylase. As can be seen in FIG. 10, regarding the respective types of the α-amylase-binding nucleic acid molecules, the electrophoresis time in the presence of the α-amylase was longer than that in the control without α-amylase. From these results, it was found that the α-amylase-binding nucleic acid molecules 1 and 5 bind to α-amylase.

(5) Examination of Binding by Pull-Down Assay

Beads 5 carrying α-amylase-binding nucleic acid molecules bound thereto (also referred to as "bound beads A5" hereinafter) were prepared by bringing the α-amylase-binding nucleic acid molecules 5 with their 5' ends modified with biotin into contact with the above-described streptavidin-modified beads. Then, imaging was performed in the same manner as in the item (5) in Example 2, except that the bound beads A5 were used in addition to the bound beads A1 and that a target sample containing α-amylase was used as the sample. Further, as control 1 and control 2, imaging was performed in the same manner except that, in control 1, nucleic acid molecules that do not bind to α-amylase with their 5' ends modified with biotin were used (the control nucleic acid molecules 1) and, in control 2, only α-amylase was used.

Figure 11:
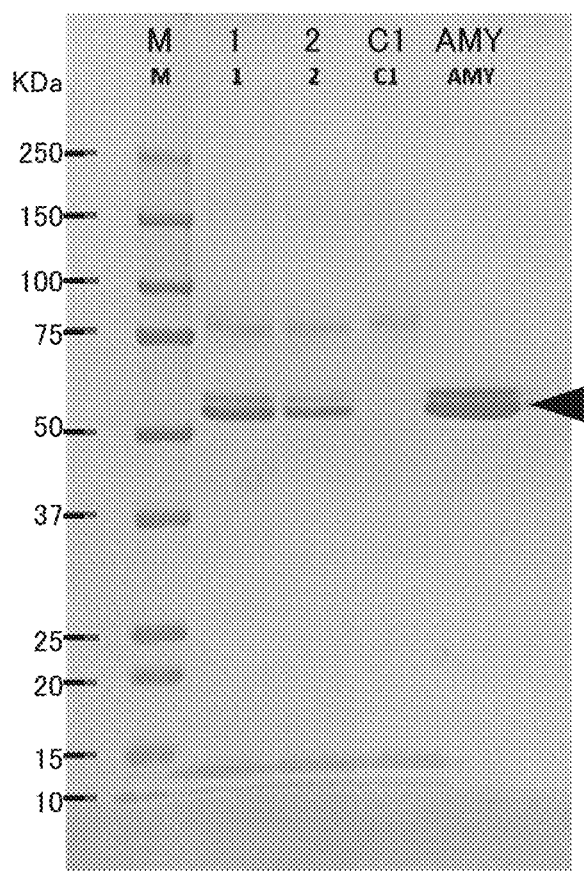
FIG. 11 is a photograph showing the results of the pull-down assay in Example 4.
Figure 12A:
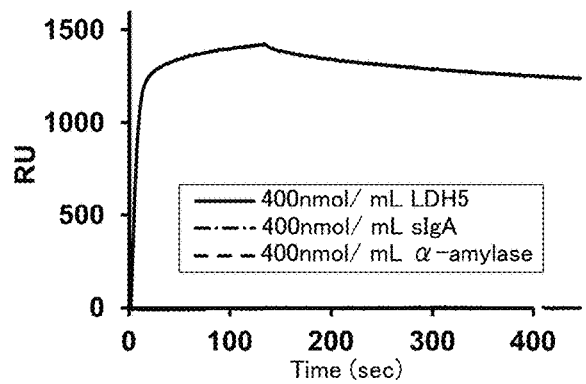
FIGS. 12A to 12D are graphs showing the binding ability of the respective types of lactate dehydrogenase (LDH) 5-binding nucleic acid molecules to LDH5 in Example 5.
Figure 12B:
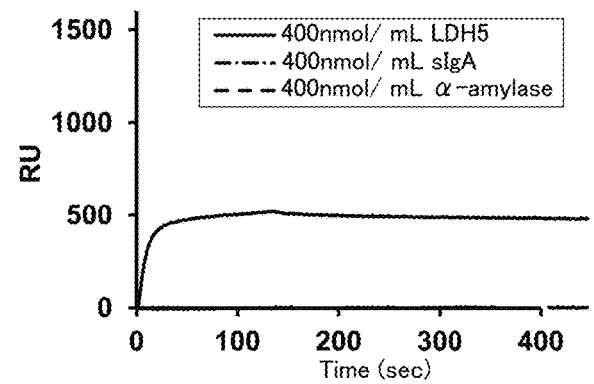
Figure 12C:
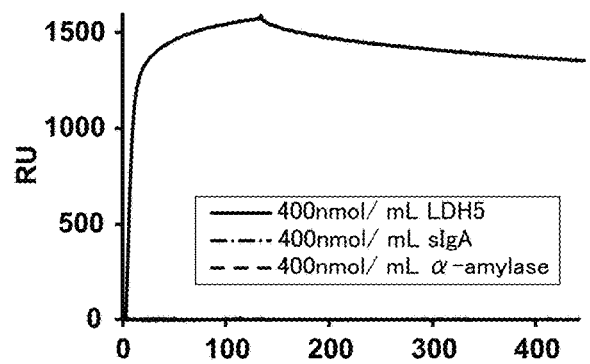
Figure 12D:
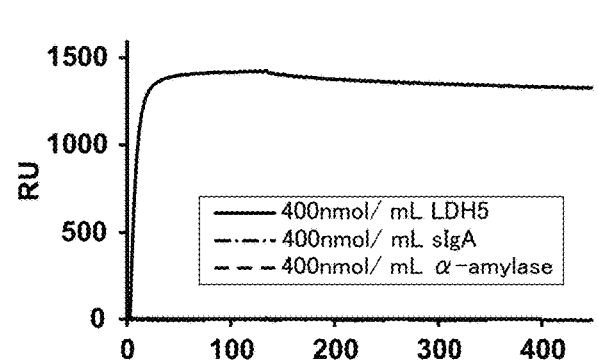

The results obtained are shown in FIG. 11. FIG. 11 is a photograph showing the results of the pull-down assay using the bound beads A1 and A5. In FIG. 11, the numerical values on the left side of the photograph indicate molecular weights, and the respective lanes show, from the left, the results obtained regarding the molecular weight marker (M), the bound beads A1 (1), the bound beads A5 (2), control 1 (C1), and control 2 (AMY). As can be seen in FIG. 11, in the lane showing the result of control 1, no band was observed at the same position (about 50 kDa) as in the lane showing the result of control 2, whereas, in the lanes showing the results regarding the bound beads A1 and A5, bands were observed at the same electrophoretic mobility position as in the lane showing the result of control 2. In other words, the binding of the α-amylase-binding nucleic acid molecules 1 and 5 to α-amylase was observed. From these results, it was found that the α-amylase-binding nucleic acid molecules 1 and 5 bind to α-amylase.

Example 5

The present example examined whether binding nucleic acid molecules that bind to human LDH5 and binding nucleic acid molecules that bind to human IL-6 can be obtained using MK4.

(1) Binding Nucleic Acid Molecule

Binding nucleic acid molecules that bind to human LDH5 and binding nucleic acid molecules that bind to human IL-6 were obtained in the same manner as in the item (1) in Example 2, except that, instead of sIgA as the target, human LDH5 (manufactured by Meridian Life Science, Inc., Catalog number: # A38558H-100) and human IL-6 (manufactured by MP Biomedicals, LLC-Cappel Products, Catalog number: #55905) were used, respectively.

As a result, as the binding nucleic acid molecules that bind to LDH5, binding nucleic acid molecules consisting of the base sequences of SEQ ID NOs: 17 to 20 shown below were obtained, and as the binding nucleic acid molecules that bind to IL-6, binding nucleic acid molecules consisting of the base sequences of SEQ ID NOs: 21 and 22 shown below were obtained. In the base sequences of SEQ ID NOs: 17 to 22 shown below, each underlined A is MK4.

```
LDH5-binding nucleic acid molecule 1
                                    (SEQ ID NO: 17)
5'-GGAATTGACACCTCGCCGTTTATGCTGCTGGCTCGTGAGACGGA
TATCAGGTCTCCTAAGGCTGGCTGGCTACTATAC-3'

LDH5-binding nucleic acid molecule 2
                                    (SEQ ID NO: 18)
5'-GGAATTGACACCTCGCCGTTTATGAGAGGGAGATCATCTCTCTG
GCGGACACAACCTAAGGCTGGCTGGCTACTATAC-3'

LDH5-binding nucleic acid molecule 3
                                    (SEQ ID NO: 19)
5'-ACCTCGCCGTTTATGCTGCTGGCTCGTGAGACGGATATCAGGTC
TCCTAAGGCTGGC-3'

LDH5-binding nucleic acid molecule 4
                                    (SEQ ID NO: 20)
5'-TGCTGCTGGCTCGTGAGACGGATATCAGGTCTCCTAAGGCTGG
C-3'

IL-6-binding nucleic acid molecule 1
                                    (SEQ ID NO: 21)
5'-GGAATTGACACCTCGCCGTTTATGAGTTCAATGGTATTGTATC
GACTCTTCTCGCCTAAGGCTGGCTGGCTACTATAC-3'

IL-6-binding nucleic acid molecule 2
                                    (SEQ ID NO: 22)
5'-ACCTCGCCGTTTATGAGTTCAATGGTATTGTATCGACTCTTCT
C-3'
```

(2) Examination of binding by SPR

The binding between the LDH5-binding nucleic acid molecules and LDH5 and the binding between the IL-6-binding nucleic acid molecules and IL-6 were measured in the same manner as in the item (2) in Example 2, except that the LDH5-binding nucleic acid molecules or the IL-6-binding nucleic acid molecules having a 20-mer poly(dT) added to their 3' ends were used as the ligand 2 and each of the following proteins was used as the analyte. As controls, the binding was examined in the same manner except that α-amylase and sIgA were used as the analytes.

LDH5: Lactate Dehydrogenase 5, Human (manufactured by Meridian Life Science, Inc., Catalogue number: # A38558H-100)

CgA: Recombinant full length Human Chromogranin A (manufactured by Creative BioMart, Catalogue number: # CHGA 26904TH)

IL-6: IL-6, manufactured by Human, Recombinant (manufactured by PeproTech, Catalogue number: #200-06)

Amylase: α-amylase (manufactured by Lee Biosolutions, Catalogue number: #120-10)

sIgA: IgA (Secretory), Human (manufactured by MP Biomedicals, LLC-Cappel Products, Catalogue number: #55905)

The results of measuring the binding between the respective types of the LDH5-binding nucleic acid molecule and LDH5 are shown in FIG. 12, and the results of measuring the binding between the respective types of IL-6-binding nucleic acid molecules and IL-6 are shown in FIG. 13.

FIGS. 12A to 12D are graphs showing the binding ability of the respective types of the LDH5-binding nucleic acid molecules to LDH5. FIGS. 12A to 12D show the results obtained regarding the LDH5-binding nucleic acid molecules 1 to 4, respectively. In each of FIGS. 12A to 12D, the horizontal axis indicates the time elapsed after the injection of the ligand, and the vertical axis indicates the relative value (RU) of the binding force. As can be seen in FIGS. 12A to 12D, the respective types of the LDH5-binding nucleic acid molecules did not bind to the amylase or sIgA and bound to LDH5.

Figure 13A:
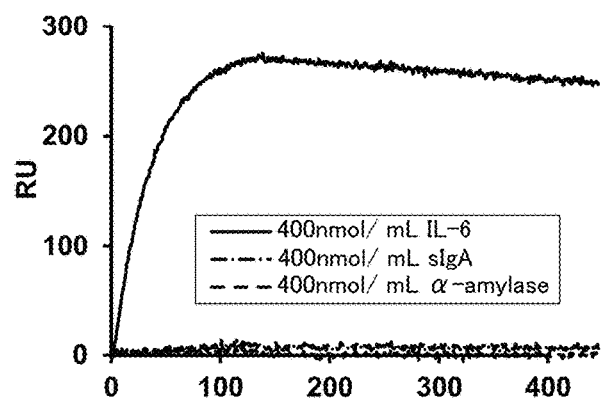
FIGS. 13A and 13B are graphs showing the binding ability of the respective types of interleukin (IL) 6-binding nucleic acid molecules to IL-6 in Example 5.
Figure 13B:
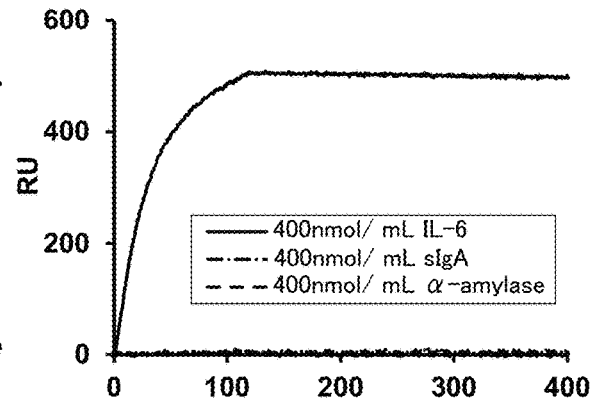

FIGS. 13A and 13B are graphs showing the binding ability of the respective types of IL-6-binding nucleic acid molecules to IL-6. FIGS. 13A and 13B show the results obtained regarding the IL-6-binding nucleic acid molecules 1 and 2, respectively. In each of FIGS. 13A and 13B, the horizontal axis indicates the time elapsed after the injection of the ligand, and the vertical axis indicates the relative value (RU) of the binding force. As can be seen in FIGS. 13A and 13B, the respective types of IL-6-binding nucleic acid molecules did not bind to the amylase or sIgA and bound to IL-6.

Next, the binding ability of each type of the binding nucleic acid molecules was examined on the basis of the amount of each type of the binding nucleic acid molecules immobilized on a measurement chip and the binding amount of each type of the binding nucleic acid molecules to the target. Specifically, the signal intensity (RU) after the injection of the ligand 2 was measured, and the measured value, which corresponds to a signal indicating the amount of each type of the binding nucleic acid molecules immobilized on the measurement chip, was regarded as an "nucleic acid molecule immobilization measured value (A)". Further, signal intensity measurement was performed concurrently with injection of the analyte and washing with a buffer. With 0 seconds being the start of the injection, the mean value of signal intensities from 115 seconds to 125 seconds was determined. This result, which corresponds to a signal indicating the binding amount between each type of the binding nucleic acid molecules and the target, was regarded as a "target binding measured value (B)". Then, the value (B/A) obtained by dividing the target binding measured value (B) by the nucleic acid molecule immobilization measured value (A) was determined as a relative value (Relative Unit), and the thus-obtained value was regarded as the binding ability. As controls, the binding ability was determined in the same manner, except that α-amylase and sIgA were used as the analytes.

Figure 14:
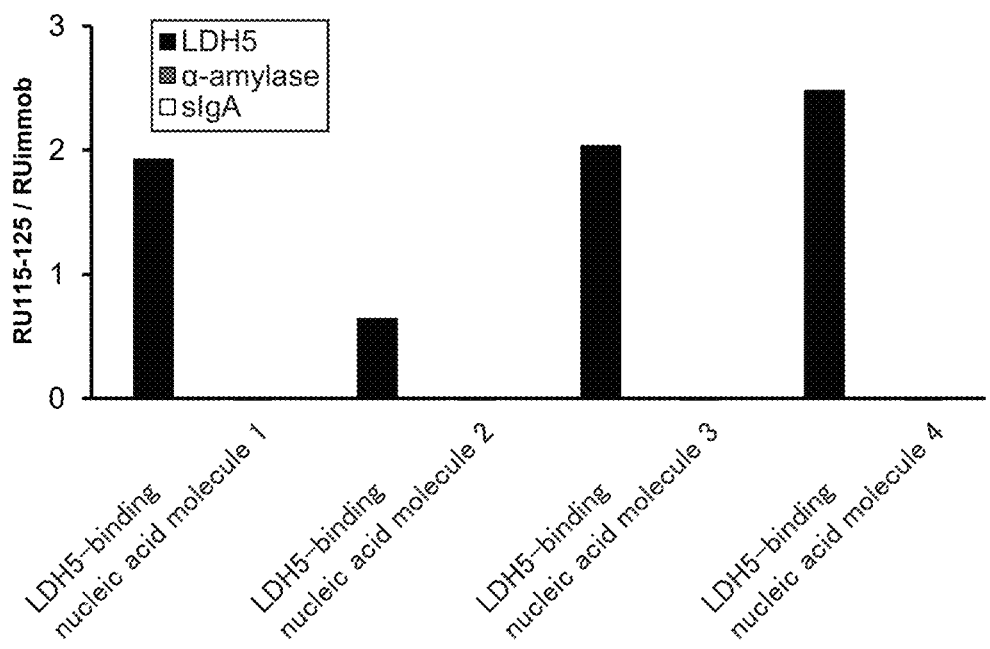
FIG. 14 is a graph showing the relative values of the binding amounts of the respective types of LDH5-binding nucleic acid molecules to LDH5 in Example 5.
Figure 15:
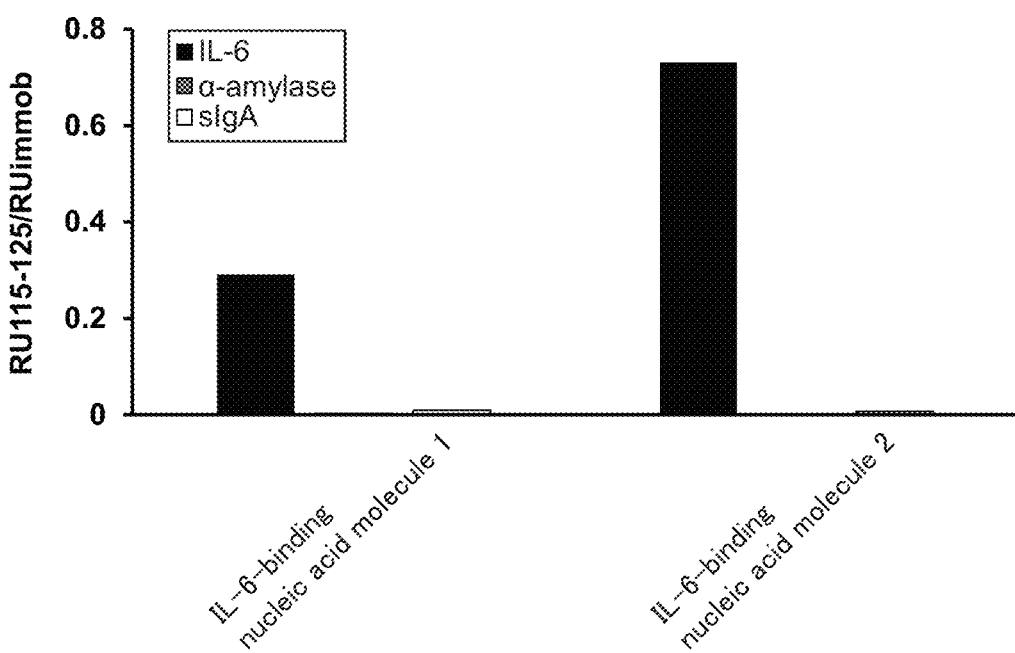
FIG. 15 is a graph showing the relative values of the binding amounts of the respective types of IL-6 binding nucleic acid molecules to IL-6 in Example 5.

The results obtained regarding the respective types of the LDH5-binding nucleic acid molecules are shown in FIG. 14, and the results obtained regarding the respective types of IL-6-binding nucleic acid molecules are shown in FIG. 15.

FIG. 14 is a graph showing the relative values (Relative Units) of the binding amounts of the respective types of the LDH5-binding nucleic acid molecules to LDH5. In FIG. 14, the horizontal axis indicates the type of the LDH5-binding nucleic acid molecules, and the vertical axis indicates the relative value. As can be seen in FIG. 14, no binding was observed in the control in which α-amylase or sIgA was used. In contrast, all the types of the LDH5-binding nucleic acid molecules bound to LDH5.

FIG. 15 is a graph showing the relative values of the binding amounts of the respective types of the IL-6-binding nucleic acid molecules to IL-6. In FIG. 15, the horizontal axis indicates the types of the IL-6-binding nucleic acid molecules, and the vertical axis indicates the relative value. As can be seen in FIG. 15, no binding was observed in the control in which α-amylase or sIgA was used. In contrast, all the types of the IL-6-binding nucleic acid molecules bound to IL-6.

From these results, it was found that a binding nucleic acid molecule that binds to LDH5 and a binding nucleic acid molecule that binds to IL-6 can be obtained using MK4, which is the nucleoside derivative according to the present invention.

(3) Examination of Binding Force

The relative value (RU) of the binding force was measured in the same manner as in the item (2) in Example 5, except that each type of the LDH5-binding nucleic acid molecules having a 20-mer poly(T) added to their 3' ends were used as the ligand 2 and that the concentration of LDH5 as the analyte was set to 1.25, 2.5, 5, 10, or 20 nmol/L or to 6.25, 12.5, 25, 50, or 100 nmol/L. Also, the relative value of the binding force (RU) was measured in the same manner as in the item (2) in Example 5, except that each type of the IL-6-binding nucleic acid molecules having a 20-mer poly(T) added to their 3' ends were used as the ligand 2 and that the concentration of IL-6 as the analyte was set to 6.25, 12.5, 25, 50, or 100 nmol/L or to 12.5, 25, 50, 100, or 200 nmol/L. Then, on the basis of the relative values of the binding force (RU) measured in the above, the dissociation constant between each type of the LDH5-binding nucleic acid molecules and LDH5 and the dissociation constant between each type of the IL-6-binding nucleic acid molecules and IL-6 were calculated. The results obtained are shown in Table 2 below.

TABLE 2

| Nucleic acid molecule name | Dissociation constant (nM) |
| --- | --- |
| LDH5-binding nucleic acid molecule 1 | 1.68 |
| LDH5-binding nucleic acid molecule 2 | 0.49 |
| LDH5-binding nucleic acid molecule 3 | 0.53 |
| LDH5-binding nucleic acid molecule 4 | 0.23 |

TABLE 2-continued

| Nucleic acid molecule name | Dissociation constant (nM) |
| --- | --- |
| LDH5-binding nucleic acid molecule 5 | 2.54 |
| LDH5-binding nucleic acid molecule 6 | 1.38 |

As can be seen in Table 2 above, it was found that these binding nucleic acid molecules all have excellent binding ability to the targets. In particular, the LDH5-binding nucleic acid molecules 2 to 4 exhibited particularly excellent binding ability to the target.

(4) Examination of Binding by Pull-Down Assay

Beads carrying LDH5-binding nucleic acid molecules bound thereto (also referred to as "bound beads L" hereinafter) were prepared by bringing the LDH5-binding nucleic acid molecules 1 with their 5' ends modified with biotin into contact with the above-described streptavidin-modified beads. Next, SDS-PAGE was performed and gel was imaged in the same manner as in the item (5) in Example 2, except that the bound beads L were mixed with a SB buffer containing 90 (v/v) % saliva (saliva sample) or a SB buffer containing LDH5 (target sample). Further, as control 1 and control 2, imaging was performed in the same manner except that, in control 1, the following control nucleic acid molecules 3 with their 5' ends modified with biotin were used and, in control 2, only LDH5 was used.

```
Control nucleic acid molecule 3
                           (SEQ ID NO: 23)
5'-GGAATTGACACCTCGCCGTTTATG-3'
```

Figure 16:
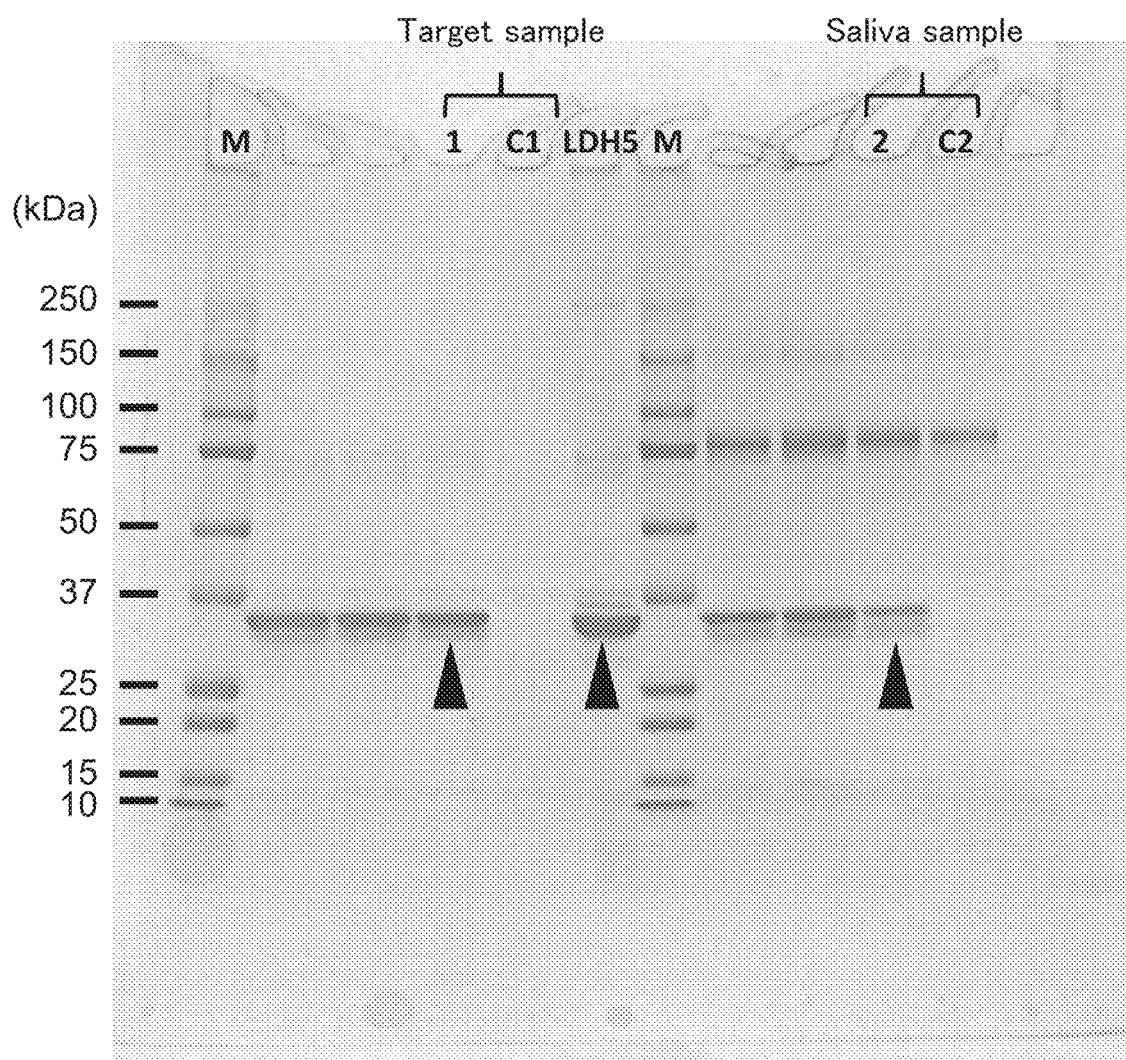
FIG. 16 is a photograph showing the results of the pull-down assay in Example 5.

Next, the results obtained when the bound beads L were used are shown in FIG. 16. FIG. 16 is a photograph showing the results of the pull-down assay using the bound beads L. In FIG. 16, the numerical values on the left side of the photograph indicate molecular weights, and the respective lanes are, from the left, lane M (marker), lane 1 (target sample), lane C1 (control 1), lane LDH5 (control 2), lane M (marker), lane 2 (saliva sample), and lane C2 (control 1). As can be seen in FIG. 16, in the lane showing the result of control 1, no band was observed at the same position (about 35 kDa) as in the lane showing the result of control 2, whereas, in the lanes showing the results obtained when the target sample and the saliva sample were used, bands were observed at the same electrophoretic mobility position as in the lane showing the result of control 2, as indicated with the arrows in FIG. 16. In other words, binding of the LDH5-binding nucleic acid molecules 1 to LDH5 was observed. From these results, it was found that the LDH5-binding nucleic acid molecules bind to LDH5.

Although the present invention is described above with reference to embodiments and examples, the present invention is not limited thereto. Various modifications can be made within the scope of the present invention which can be understood by those skilled in the art.

(Supplementary Notes)

Some or all of the above-described embodiments and examples may be described, but are not limited to, as the following Supplementary Notes.

(Supplementary Note 1)

A nucleoside derivative or a salt thereof, represented by the following chemical formula (1):

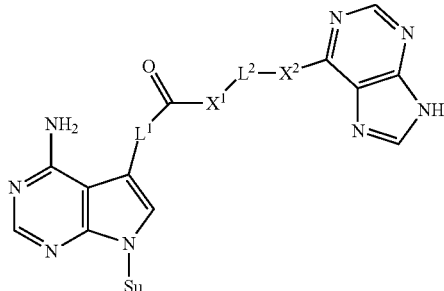

(1)

where in the chemical formula (1),

Su is an atomic group having a sugar skeleton at a nucleoside residue or an atomic group having a sugar phosphate skeleton at a nucleotide residue, and may or may not have a protecting group, $L^1$ and $L^2$ are each independently a straight-chain or branched, saturated or unsaturated hydrocarbon group having 2 to 10 carbon atoms, $X^1$ and $X^2$ are each independently an imino group (—$NR^1$—), an ether group (—O—), or a thioether group (—S—), and the $R^1$ is a hydrogen atom or a straight-chain or branched, saturated or unsaturated hydrocarbon group having 2 to 10 carbon atoms.

(Supplementary Note 2)

The nucleoside derivative or a salt thereof according to Supplementary Note 1, wherein the $X^1$ is an imino group (—$NR^1$—).

(Supplementary Note 3)

The nucleoside derivative or a salt thereof according to Supplementary Note 1 or 2, wherein the $X^2$ is an imino group (—$NR^1$—).

(Supplementary Note 4)

The nucleoside derivative or a salt thereof according to Supplementary Note 2 or 3, wherein the $R^1$ is a hydrogen atom.

(Supplementary Note 5)

The nucleoside derivative or a salt thereof according to any one of Supplementary Notes 1 to 4, wherein the $L^1$ is a vinylene group (—CH=CH—).

(Supplementary Note 6) The nucleoside derivative or a salt thereof according to any one of Supplementary Notes 1 to 5, wherein the $L^2$ is an ethylene group (—$CH_2$—$CH_2$—).

(Supplementary Note 7)

The nucleoside derivative or a salt thereof according to any one of Supplementary Notes 1 to 6, wherein an atomic group having a sugar skeleton at the nucleoside residue or an atomic group having a sugar phosphate skeleton at the nucleotide residue is represented by the following chemical formula (2):

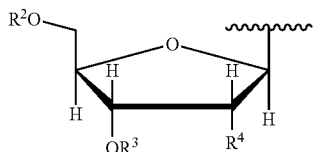

(2)

where in the chemical formula (2), $R^2$ is a hydrogen atom, a protecting group, or a group represented by the following chemical formula (3), $R^3$ is a hydrogen atom, a protecting group, or a phosphoramidite group, $R^4$ is a hydrogen atom, a fluorine atom, a hydroxyl group, an amino group, or a mercapto group,

(3)

where in the chemical formula (3),

Y is an oxygen atom or a sulfur atom,

Z is a hydroxyl group or an imidazole group, and m is an integer of 1 to 10.

(Supplementary Note 8)

The nucleoside derivative or a salt thereof according to any one of Supplementary Notes 1 to 7, wherein the nucleoside derivative represented by the chemical formula (1) is a nucleoside derivative represented by the following chemical formula (4):

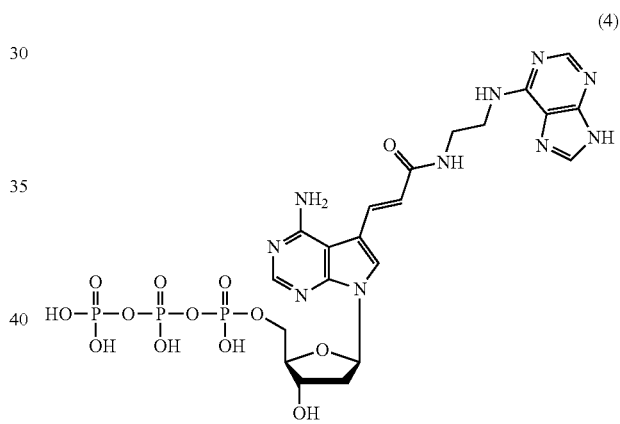

(4)

(Supplementary Note 9)

A polynucleotide synthesis reagent comprising a nucleotide derivative or a salt thereof that comprises the nucleoside derivative or a salt thereof according to any one of Supplementary Notes 1 to 8.

(Supplementary Note 10)

A method for producing a polynucleotide, comprising the step of synthesizing a polynucleotide using a nucleotide derivative or a salt thereof that comprises the nucleoside derivative or a salt thereof according to any one of Supplementary Notes 1 to 8.

(Supplementary Note 11)

A polynucleotide comprising, as a building block, a nucleotide derivative or a salt thereof that comprises the nucleoside derivative or a salt thereof according to any one of Supplementary Notes 1 to 8.

(Supplementary Note 12)

The polynucleotide according to Supplementary Note 11, wherein the polynucleotide is a binding nucleic acid molecule that binds to a target.

(Supplementary Note 13)

The polynucleotide according to Supplementary Note 12, wherein the target is at least one selected from the group consisting of secretory immunoglobulin A, amylase, β-defensin 4A, lysozyme, lactate dehydrogenase (LDH) 5, and interleukin (IL)-6.

(Supplementary Note 14)

A method for producing a binding nucleic acid molecule, comprising the steps of:

causing a candidate polynucleotide and a target to come into contact with each other; and selecting the candidate polynucleotide bound to the target as a binding nucleic acid molecule that binds to the target, wherein the candidate polynucleotide is the polynucleotide according to any one of Supplementary Notes 11 to 13.

(Supplementary Note 15)

The method according to Supplementary Note 14, wherein the target is at least one selected from the group consisting of secretory immunoglobulin A, amylase, β-defensin 4A, lysozyme, lactate dehydrogenase (LDH) 5, and interleukin (IL)-6.

(Supplementary Note 16)

An α-amylase-binding nucleic acid molecule comprising a polynucleotide (a):

(a) a polynucleotide (a1):

(a1) a polynucleotide consisting of any of base sequences of SEQ ID NOs: 1 and 11 to 16.

(Supplementary Note 17)

The α-amylase-binding nucleic acid molecule according to Supplementary Note 16, wherein the α-amylase-binding nucleic acid molecule comprises a modified base, which is a base modified.

(Supplementary Note 18)

The α-amylase-binding nucleic acid molecule according to Supplementary Note 17, wherein the modified base is a modified purine base, which is a purine base modified with a modifying group.

(Supplementary Note 19)

The α-amylase-binding nucleic acid molecule according to Supplementary Note 18, wherein modifying group is an adenine residue.

(Supplementary Note 20)

The α-amylase-binding nucleic acid molecule according to any one of Supplementary Notes 16 to 19, wherein the polynucleotide is DNA.

(Supplementary Note 21)

A method for analyzing α-amylase, comprising the step of:

causing a specimen and a nucleic acid molecule to come into contact with each other to detect α-amylase in a specimen, wherein the nucleic acid molecule is an α-amylase-binding nucleic acid molecule according to any one of Supplementary Notes 16 to 20, and in the detection, the nucleic acid molecule is caused to bind to the α-amylase in the specimen, and the α-amylase in the specimen is detected by detecting the binding.

(Supplementary Note 22)

The method according to Supplementary Note 21, wherein the specimen is at least one selected from the group consisting of saliva, urine, plasma, and serum.

(Supplementary Note 23)

A β-defensin (BDN)4A-binding nucleic acid molecule comprising a polynucleotide (b):

(b) a polynucleotide (b1):

(b1) a polynucleotide consisting of any of base sequences of SEQ ID NOs: 4 to 6.

(Supplementary Note 24)

The BDN4A-binding nucleic acid molecule according to Supplementary Note 23, wherein the BDN4A-binding nucleic acid molecule comprises a modified base, which is a base modified.

(Supplementary Note 25)

The BDN4A-binding nucleic acid molecule according to Supplementary Note 24, wherein the modified base is a modified purine base, which is a purine base modified with a modifying group.

(Supplementary Note 26)

The BDN4A-binding nucleic acid molecule according to Supplementary Note 25, wherein the modifying group is an adenine residue.

(Supplementary Note 27)

The BDN4A-binding nucleic acid molecule according to any one of Supplementary Notes 23 to 26, wherein the polynucleotide is DNA.

(Supplementary Note 28)

A method for analyzing BDN4A, comprising the step of: causing a specimen and a nucleic acid molecule to come into contact with each other to detect β-defensin (BDN)4A in the specimen, wherein the nucleic acid molecule is the BDN4A binding nucleic acid molecule according to any one of Supplementary Notes 23 to 27, and in the detection step, the nucleic acid molecule is caused to bind to the BDN4A in the specimen, and the BDN4A in the specimen is detected by detecting the binding.

(Supplementary Note 29)

The method according to Supplementary Note 28, wherein the specimen is at least one selected from the group consisting of saliva, urine, plasma, and serum.

(Supplementary Note 30)

A lysozyme-binding nucleic acid molecule comprising a polynucleotide (l):

(l) a polynucleotide (l1):

(l1) a polynucleotide consisting of any of base sequences of SEQ ID NOs: 7 to 9.

(Supplementary Note 31)

The lysozyme-binding nucleic acid molecule according to Supplementary Note 30, wherein the lysozyme-binding nucleic acid molecule comprises a modified base, which is a base modified.

(Supplementary Note 32)

The lysozyme-binding nucleic acid molecule according to Supplementary Note 31, wherein the modified base is a modified purine base, which is a purine base modified with a modifying group.

(Supplementary Note 33)

The lysozyme-binding nucleic acid molecule according to Supplementary Note 32, wherein the modifying group is an adenine residue.

(Supplementary Note 34)

The lysozyme-binding nucleic acid molecule according to any one of Supplementary Notes 30 to 33, wherein the polynucleotide is DNA.

(Supplementary Note 35)

A method for analyzing lysozyme, comprising the step of:

causing a specimen and a nucleic acid molecule to come into contact with each other to detect lysozyme in the specimen, wherein the nucleic acid molecule is the lysozyme-binding nucleic acid molecule according to any one of Supplementary Notes 30 to 34, and in the detection, the nucleic acid molecule is caused to bind to the lysozyme in the specimen, and the lysozyme in the specimen is detected by detecting the binding.

(Supplementary Note 36) The method according to Supplementary Note 35, wherein the specimen is at least one selected from the group consisting of saliva, urine, plasma, and serum.

(Supplementary Note 37)

A lactate dehydrogenase (LDH)5-binding nucleic acid molecule comprising a polynucleotide (d):

(d) a polynucleotide (d1):

(d1) a polynucleotide consisting of any of base sequences of SEQ ID NOs: 17 to 20.

(Supplementary Note 38)

The LDH5-binding nucleic acid molecule according to Supplementary Note 37, wherein the LDH5-binding nucleic acid molecule comprises a modified base, which is a base modified.

(Supplementary Note 39)

The LDH5-binding nucleic acid molecule according to Supplementary Note 38, wherein the modified base is a modified thymine, which is a thymine base modified with a modifying group.

(Supplementary Note 40)

The LDH5-binding nucleic acid molecule according to Supplementary Note 39, wherein the modifying group is an adenine residue.

(Supplementary Note 41)

The LDH5-binding nucleic acid molecule according to any one of Supplementary Notes 37 to 40, wherein the polynucleotide is DNA.

(Supplementary Note 42)

A method for analyzing LDH5, comprising the step of:

causing a specimen and a nucleic acid molecule to come into contact with each other to detect lactate dehydrogenase (LDH)5 in the specimen, wherein the nucleic acid molecule is the LDH5-binding nucleic acid molecule according to any one of Supplementary Notes 37 to 41, and in the detection step, the nucleic acid molecule is caused to bind to the LDH5 in the specimen, and the LDH5 in the specimen is detected by detecting the binding.

(Supplementary Note 43)

The method according to Supplementary Note 42, wherein the specimen is at least one selected from the group consisting of saliva, urine, plasma, and serum.

(Supplementary Note 44)

An interleukin (IL)-6 binding nucleic acid molecule comprising a polynucleotide (i):

(i) a polynucleotide (i1):

(i1) a polynucleotide consisting of any of base sequences of SEQ ID NOs: 21 and 22.

(Supplementary Note 45)

The IL-6-binding nucleic acid molecule according to Supplementary Note 44, wherein the IL-6-binding nucleic acid molecule comprises a modified base, which is a base modified.

(Supplementary Note 46)

The IL-6-binding nucleic acid molecule according to Supplementary Note 45, wherein the modified base is a modified thymine, which is a thymine base modified with a modifying group.

(Supplementary Note 47)

The IL-6-binding nucleic acid molecule according to Supplementary Note 46, wherein the modifying group is an adenine residue.

(Supplementary Note 48)

The IL-6-binding nucleic acid molecule according to any one of Supplementary Notes 44 to 47, wherein the polynucleotide is DNA.

(Supplementary Note 49)

A method for analyzing IL-6, comprising the step of:

causing a specimen and a nucleic acid molecule to come into contact with each other to detect interleukin (IL)-6 in the specimen, wherein the nucleic acid molecule is the IL-6-binding nucleic acid molecule according to any one of Supplementary Notes 44 to 48, and in the detection step, the nucleic acid molecule is caused to bind to the IL-6 in the specimen, and the IL-6 in the specimen is detected by detecting the binding.

(Supplementary Note 50)

The method according to Supplementary Note 49, wherein the specimen is at least one selected from the group consisting of saliva, urine, plasma, and serum.

INDUSTRIAL APPLICABILITY

The present invention can provide a novel nucleoside derivative or a salt thereof. Further, the nucleoside derivative of the present invention has two purine ring-like structures. The nucleoside derivative of the present invention thus has, for example, a relatively larger number of atoms capable of interacting within or between molecules than a nucleoside derivative having one purine ring-like structure. The binding nucleic acid molecule including the nucleoside derivative of the present invention therefore has an improved binding ability to a target, for example, compared to a nucleoside derivative having one purine ring-like structure. Thus, with the nucleoside derivative of the present invention, a binding nucleic acid molecule that exhibits excellent binding ability to a target can be produced, for example. Accordingly, the present invention is really useful, for example, in the fields of analysis, medicine, life science, and the like.

[Sequence Listing] TF16066WO2_ST25.txt

The invention claimed is:

1. A nucleoside derivative or a salt thereof, represented by the following chemical formula (1):

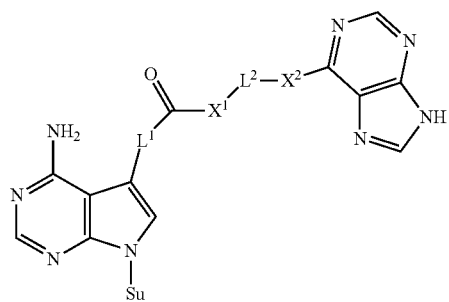

(1)

wherein, in the chemical formula (1),
Su is an atomic group having a sugar skeleton at a nucleoside residue or an atomic group having a sugar phosphate skeleton at a nucleotide residue, and may or may not have a protecting group,
$L^1$ and $L^2$ are each independently a straight-chain or branched, saturated or unsaturated hydrocarbon group having 2 to 10 carbon atoms,
$X^1$ and $X^2$ are each independently an imino group ($-NR^1-$), an ether group ($-O-$), or a thioether group ($-S-$), and
the $R^1$ is a hydrogen atom or a straight-chain or branched, saturated or unsaturated hydrocarbon group having 2 to 10 carbon atoms.

2. The nucleoside derivative or a salt thereof according to claim 1, wherein the $X^1$ is an imino group ($-NR^1-$).

3. The nucleoside derivative or a salt thereof according to claim 1, wherein the $X^2$ is an imino group ($-NR^1-$).

4. The nucleoside derivative or a salt thereof according to claim 2, wherein the $R^1$ is a hydrogen atom.

5. The nucleoside derivative or a salt thereof according to claim 1, wherein the $L^1$ is a vinylene group ($-CH=CH-$).

6. The nucleoside derivative or a salt thereof according to claim 1, wherein the $L^2$ is an ethylene group ($-CH_2-CH_2-$).

7. The nucleoside derivative or a salt thereof according to claim 1, wherein the atomic group having a sugar skeleton at a nucleoside residue or the atomic group having a sugar phosphate skeleton at a nucleotide residue is represented by the following chemical formula (2):

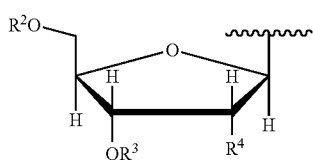

(2)

wherein, in the chemical formula (2), $R^2$ is a hydrogen atom, a protecting group, or a group represented by the following chemical formula (3), $R^3$ is a hydrogen atom, a protecting group, or a phosphoramidite group, and $R^4$ is a hydrogen atom, a fluorine atom, a hydroxyl group, an amino group, or a mercapto group,

(3)

wherein, in the chemical formula (3),

Y is an oxygen atom or a sulfur atom,

Z is a hydroxyl group or an imidazole group, and m is an integer of 1 to 10.

8. The nucleoside derivative or a salt thereof according to claim 1, wherein the nucleoside derivative represented by the chemical formula (1) is a nucleoside derivative represented by the following chemical formula (4):

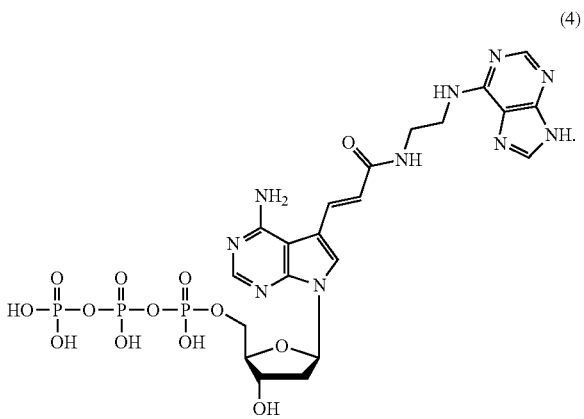

(4)

9. A polynucleotide synthesis reagent comprising a nucleotide derivative or a salt thereof represented by the following chemical formula (1):

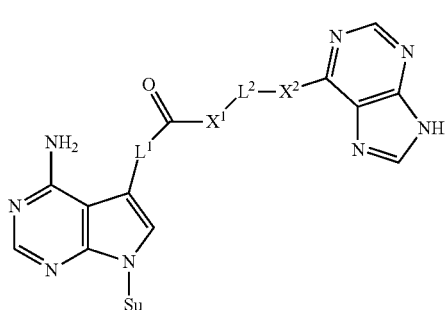
(1)

wherein, in the chemical formula (1),
Su is an atomic group having a sugar phosphate skeleton at a nucleotide residue, and may or may not have a protecting group,
$L^1$ and $L^2$ are each independently a straight-chain or branched, saturated or unsaturated hydrocarbon group having 2 to 10 carbon atoms,
$X^1$ and $X^2$ are each independently an imino group (—$NR^1$—), an ether group (—O—), or a thioether group (—S—), and
the $R^1$ is a hydrogen atom or a straight-chain or branched, saturated or unsaturated hydrocarbon group having 2 to 10 carbon atoms,
wherein the atomic group having a sugar phosphate skeleton at a nucleotide residue is represented by the following chemical formula (2):

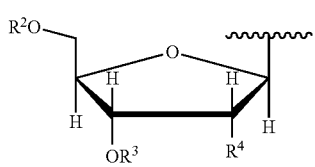
(2)

wherein, in the chemical formula (2),
$R^2$ is a hydrogen atom, a protecting group, or a group represented by the following chemical formula (3),
$R^3$ is a hydrogen atom, a protecting group, or a phosphoramidite group, and
$R^4$ is a hydrogen atom, a fluorine atom, a hydroxyl group, an amino group, or a mercapto group,

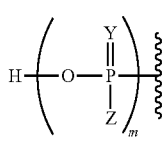
(3)

wherein, in the chemical formula (3),
Y is an oxygen atom or a sulfur atom,
Z is a hydroxyl group or an imidazole group, and
m is an integer of 1 to 10.

10. A method for producing a polynucleotide, comprising the step of synthesizing a polynucleotide using a nucleotide derivative or a salt thereof represented by the following chemical formula (1):

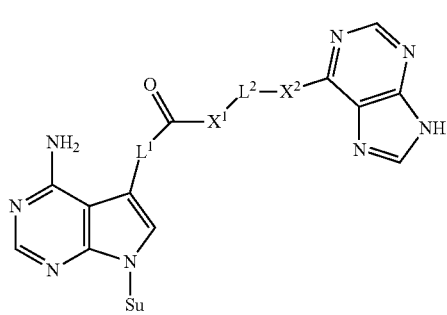
(1)

wherein, in the chemical formula (1),
Su is an atomic group having a sugar phosphate skeleton at a nucleotide residue, and may or may not have a protecting group,
$L^1$ and $L^2$ are each independently a straight-chain or branched, saturated or unsaturated hydrocarbon group having 2 to 10 carbon atoms,
$X^1$ and $X^2$ are each independently an imino group (—$NR^1$—), an ether group (—O—), or a thioether group (—S—), and
the $R^1$ is a hydrogen atom or a straight-chain or branched, saturated or unsaturated hydrocarbon group having 2 to 10 carbon atoms,
wherein the atomic group having a sugar phosphate skeleton at a nucleotide residue is represented by the following chemical formula (2):

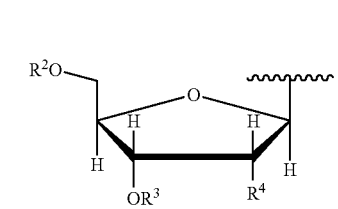
(2)

wherein, in the chemical formula (2),
$R^2$ is a hydrogen atom, a protecting group, or a group represented by the following chemical formula (3),
$R^3$ is a hydrogen atom, a protecting group, or a phosphoramidite group, and
$R^4$ is a hydrogen atom, a fluorine atom, a hydroxyl group, an amino group, or a mercapto group,

(3)

wherein, in the chemical formula (3),
Y is an oxygen atom or a sulfur atom,
Z is a hydroxyl group or an imidazole group, and
m is an integer of 1 to 10.

* * * * *

UNITED STATES PATENT AND TRADEMARK OFFICE
CERTIFICATE OF CORRECTION

PATENT NO. : 10,781,230 B2  
APPLICATION NO. : 16/333333  
DATED : September 22, 2020  
INVENTOR(S) : Hirotaka Minagawa et al.

Page 1 of 1

It is certified that error appears in the above-identified patent and that said Letters Patent is hereby corrected as shown below:

On the Title Page

Page 2, Column 2, item (56), Other Publications, Line 11; Delete "Oorwijn" and insert --Oortwijn-- therefor Page 2, Column 2, item (56), Other Publications, Line 17; Delete "Minigawa" and insert --Minagawa-- therefor Page 2, Column 2, item (56), Other Publications, Line 27; Delete "2'-0,4'-C-" and insert --2'-O,4'-C- -- therefor In the Specification Column 24, Description of Embodiments, Line 21; Delete "(1):" and insert --(b1):-- therefor Column 32, Description of Embodiments, Line 45; Delete "9.48×10" and insert --9.48×10$^{-4}$-- therefor Signed and Sealed this  
Twenty-second Day of December, 2020

Andrei Iancu  
*Director of the United States Patent and Trademark Office*

SEQUENCE LISTING

```
<160> NUMBER OF SEQ ID NOS: 23

<210> SEQ ID NO 1
<211> LENGTH: 78
<212> TYPE: DNA
<213> ORGANISM: Artificial Sequence
<220> FEATURE:
```

<223> OTHER INFORMATION: Synthesized polynucleotide (alpha amylase
      binding nucleic acid molecule 1)

<400> SEQUENCE: 1
ggtttggacg caatctccct aatctagtga cgaaaatgta cgagggggtc atttgaaact    60
acaatgggcg ggcttatc                                                 78

<210> SEQ ID NO 2
<211> LENGTH: 80
<212> TYPE: DNA
<213> ORGANISM: Artificial Sequence
<220> FEATURE:
<223> OTHER INFORMATION: Synthesized polynucleotide (sIgA binding
      nucleic acid molecule)

<400> SEQUENCE: 2
ggtttggacg caatctccct aatcaagcca cggagagtcc gaggtgacca ttaagcagga    60
aactacaatg ggcgggctta                                               80

<210> SEQ ID NO 3
<211> LENGTH: 23
<212> TYPE: DNA
<213> ORGANISM: Artificial Sequence
<220> FEATURE:
<223> OTHER INFORMATION: Synthesized polynucleotide (control nucleic
      acid molecule)

<400> SEQUENCE: 3
ggatacctta acgccgccta ttg                                           23

<210> SEQ ID NO 4
<211> LENGTH: 76
<212> TYPE: DNA
<213> ORGANISM: Artificial Sequence
<220> FEATURE:
<223> OTHER INFORMATION: Synthesized polynucleotide (BDN4A binding
      nucleic acid molecule 1)

<400> SEQUENCE: 4
ggttacacga gccgcacatt tctattttta cggggtatag ttctctgagg aggagttccc    60
aggcgaagtt gttatc                                                   76

<210> SEQ ID NO 5
<211> LENGTH: 69
<212> TYPE: DNA
<213> ORGANISM: Artificial Sequence
<220> FEATURE:
<223> OTHER INFORMATION: Synthesized polynucleotide (BDN4A binding
      nucleic acid molecule 2)

<400> SEQUENCE: 5
cgagccgcac atttctattt ttacggggta tagttctctg aggaggagtt cccaggcgaa    60
gttgttatc                                                           69

<210> SEQ ID NO 6
<211> LENGTH: 76
<212> TYPE: DNA
<213> ORGANISM: Artificial Sequence
<220> FEATURE:
<223> OTHER INFORMATION: Synthesized polynucleotide (BDN4A binding
      nucleic acid molecule 3)

<400> SEQUENCE: 6
ggttacacga gccgcacatt tcaccgtgat agttctctga ggaggacttc tagagttccc    60

```
aggcgaagtt gttatc                                                    76

<210> SEQ ID NO 7
<211> LENGTH: 76
<212> TYPE: DNA
<213> ORGANISM: Artificial Sequence
<220> FEATURE:
<223> OTHER INFORMATION: Synthesized polynucleotide (Lysozyme binding
      nucleic acid molecule 1)

<400> SEQUENCE: 7
ggttacacga gccgcacatt tctaacggga acttcaaccc atacagtctt ttgagttccc    60
aggcgaagtt gttatc                                                    76

<210> SEQ ID NO 8
<211> LENGTH: 53
<212> TYPE: DNA
<213> ORGANISM: Artificial Sequence
<220> FEATURE:
<223> OTHER INFORMATION: Synthesized polynucleotide (Lysozyme binding
      nucleic acid molecule 2)

<400> SEQUENCE: 8
cgagccgcac atttctaacg ggaacttcaa cccatacagt cttttgagtt ccc           53

<210> SEQ ID NO 9
<211> LENGTH: 76
<212> TYPE: DNA
<213> ORGANISM: Artificial Sequence
<220> FEATURE:
<223> OTHER INFORMATION: Synthesized polynucleotide (Lysozyme binding
      nucleic acid molecule 3)

<400> SEQUENCE: 9
ggttacacga gccgcacatt tctttactcc ggaacccata cagtcttttc cggagttccc    60
aggcgaagtt gttatc                                                    76

<210> SEQ ID NO 10
<211> LENGTH: 23
<212> TYPE: DNA
<213> ORGANISM: Artificial Sequence
<220> FEATURE:
<223> OTHER INFORMATION: Synthesized polynucleotide (control nucleic
      acid molecule 2)

<400> SEQUENCE: 10
ggtaaccgcc ctgtcttgat aac                                            23

<210> SEQ ID NO 11
<211> LENGTH: 61
<212> TYPE: DNA
<213> ORGANISM: Artificial Sequence
<220> FEATURE:
<223> OTHER INFORMATION: Synthesized polynucleotide (alpha amylase
      binding nucleic acid molecule 2)

<400> SEQUENCE: 11
ggtttggacg caatctccct aatctagtga cgaaaatgta cgaggggtc atttgaaact     60 a                                                                    61

<210> SEQ ID NO 12
<211> LENGTH: 52
<212> TYPE: DNA
<213> ORGANISM: Artificial Sequence
```

```
<220> FEATURE:
<223> OTHER INFORMATION: Synthesized polynucleotide (alpha amylase
      binding nucleic acid molecule 3)

<400> SEQUENCE: 12
gcaatctccc taatctagtg acgaaaatgt acgagggggt catttgaaac ta           52

<210> SEQ ID NO 13
<211> LENGTH: 78
<212> TYPE: DNA
<213> ORGANISM: Artificial Sequence
<220> FEATURE:
<223> OTHER INFORMATION: Synthesized polynucleotide (alpha amylase
      binding nucleic acid molecule 4)

<400> SEQUENCE: 13
ggtttggacg caatctccct aatcagacta ttatttcaag tacgtggggg tcttgaaact   60
acaatgggcg ggcttatc                                                 78

<210> SEQ ID NO 14
<211> LENGTH: 78
<212> TYPE: DNA
<213> ORGANISM: Artificial Sequence
<220> FEATURE:
<223> OTHER INFORMATION: Synthesized polynucleotide (alpha amylase
      binding nucleic acid molecule 5)

<400> SEQUENCE: 14
ggtttggacg caatctccct aatctaaagt ttctaaacga tgtggcggca ttcagaaact   60
acaatgggcg ggcttatc                                                 78

<210> SEQ ID NO 15
<211> LENGTH: 60
<212> TYPE: DNA
<213> ORGANISM: Artificial Sequence
<220> FEATURE:
<223> OTHER INFORMATION: Synthesized polynucleotide (alpha amylase
      binding nucleic acid molecule 6)

<400> SEQUENCE: 15
ggtttggacg caatctccct aatctaaagt ttctaaacga tgtggcggca ttcagaaact   60

<210> SEQ ID NO 16
<211> LENGTH: 51
<212> TYPE: DNA
<213> ORGANISM: Artificial Sequence
<220> FEATURE:
<223> OTHER INFORMATION: Synthesized polynucleotide (alpha amylase
      binding nucleic acid molecule 7)

<400> SEQUENCE: 16
gcaatctccc taatctaaag tttctaaacg atgtggcggc attcagaaac t            51

<210> SEQ ID NO 17
<211> LENGTH: 78
<212> TYPE: DNA
<213> ORGANISM: Artificial Sequence
<220> FEATURE:
<223> OTHER INFORMATION: Synthesized polynucleotide (LDH5 binding
      nucleic acid molecule 1)

<400> SEQUENCE: 17
ggaattgaca cctcgccgtt tatgctgctg gctcgtgaga cggatatcag gtctcctaag   60
gctggctggc tactatac                                                 78
```

<210> SEQ ID NO 18
<211> LENGTH: 78
<212> TYPE: DNA
<213> ORGANISM: Artificial Sequence
<220> FEATURE:
<223> OTHER INFORMATION: Synthesized polynucleotide (LDH5 binding
      nucleic acid molecule 2)

<400> SEQUENCE: 18
ggaattgaca cctcgccgtt tatgagaggg agatcatctc tctggcggac acaacctaag      60
gctggctggc tactatac                                                   78

<210> SEQ ID NO 19
<211> LENGTH: 57
<212> TYPE: DNA
<213> ORGANISM: Artificial Sequence
<220> FEATURE:
<223> OTHER INFORMATION: Synthesized polynucleotide (LDH5 binding
      nucleic acid molecule 3)

<400> SEQUENCE: 19
acctcgccgt ttatgctgct ggctcgtgag acggatatca ggtctcctaa ggctggc        57

<210> SEQ ID NO 20
<211> LENGTH: 44
<212> TYPE: DNA
<213> ORGANISM: Artificial Sequence
<220> FEATURE:
<223> OTHER INFORMATION: Synthesized polynucleotide (LDH5 binding
      nucleic acid molecule 4)

<400> SEQUENCE: 20
tgctgctggc tcgtgagacg gatatcaggt ctcctaaggc tggc                      44

<210> SEQ ID NO 21
<211> LENGTH: 78
<212> TYPE: DNA
<213> ORGANISM: Artificial Sequence
<220> FEATURE:
<223> OTHER INFORMATION: Synthesized polynucleotide (IL-6 binding
      nucleic acid molecule 1)

<400> SEQUENCE: 21
ggaattgaca cctcgccgtt tatgagttca atggtattgt atcgactctt ctcgcctaag      60
gctggctggc tactatac                                                   78

<210> SEQ ID NO 22
<211> LENGTH: 44
<212> TYPE: DNA
<213> ORGANISM: Artificial Sequence
<220> FEATURE:
<223> OTHER INFORMATION: Synthesized polynucleotide (IL-6 binding
      nucleic acid molecule 2)

<400> SEQUENCE: 22
acctcgccgt ttatgagttc aatggtattg tatcgactct tctc                      44

<210> SEQ ID NO 23
<211> LENGTH: 24
<212> TYPE: DNA
<213> ORGANISM: Artificial Sequence
<220> FEATURE:
<223> OTHER INFORMATION: Synthesized polynucleotide (control nucleic
      acid molecule 3)

```
<400> SEQUENCE: 23
ggaattgaca cctcgccgtt tatg                                          24
```